US009408854B2

(12) United States Patent
Bianchi et al.

(10) Patent No.: US 9,408,854 B2
(45) Date of Patent: Aug. 9, 2016

(54) METHODS AND SYSTEMS FOR PHARMACOGENOMIC TREATMENT OF CARDIOVASCULAR CONDITIONS

(75) Inventors: Giuseppe Bianchi, Milan (IT); Patrizia Ferrari, Varese (IT); Fabio Macciardi, Milan (IT)

(73) Assignee: ROSTAQUO S.P.A., Pomezia (IT)

( * ) Notice: Subject to any disclaimer, the term of this patent is extended or adjusted under 35 U.S.C. 154(b) by 0 days.

(21) Appl. No.: 13/502,518

(22) PCT Filed: Oct. 18, 2010

(86) PCT No.: PCT/EP2010/065589
§ 371 (c)(1),
(2), (4) Date: Sep. 1, 2012

(87) PCT Pub. No.: WO2011/048033
PCT Pub. Date: Apr. 28, 2011

(65) Prior Publication Data
US 2013/0018024 A1 Jan. 17, 2013

Related U.S. Application Data

(60) Provisional application No. 61/253,020, filed on Oct. 19, 2009.

(30) Foreign Application Priority Data

Nov. 25, 2009 (EP) .................................. 09177111

(51) Int. Cl.
| C12Q 1/68 | (2006.01) |
| A61K 31/58 | (2006.01) |
| C07J 17/00 | (2006.01) |
| A61K 31/56 | (2006.01) |

(52) U.S. Cl.
CPC .............. *A61K 31/56* (2013.01); *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 5,591,734 | A | 1/1997 | Bianchi et al. | |
| 5,632,276 | A | 5/1997 | Eidelberg et al. | |
| 5,981,174 | A | 11/1999 | Wolf et al. | |
| 6,114,128 | A | 9/2000 | Håkansson et al. | |
| 6,399,310 | B1 | 6/2002 | Murphy, Jr. et al. | |
| 6,610,489 | B2 | 8/2003 | Wolffe et al. | |
| 2002/0037849 | A1* | 3/2002 | Fruebis et al. | 514/12 |
| 2002/0132234 | A1* | 9/2002 | Moskowitz | 435/6 |
| 2003/0092620 | A1* | 5/2003 | Lucas et al. | 514/12 |
| 2004/0166491 | A1* | 8/2004 | Henderson | 435/6 |
| 2005/0065079 | A1* | 3/2005 | Scalia et al. | 514/12 |
| 2006/0058507 | A1* | 3/2006 | Briggs et al. | 530/350 |
| 2006/0177838 | A1 | 8/2006 | Ligget et al. | |
| 2008/0096982 | A1 | 4/2008 | Liggett et al. | |
| 2008/0248476 | A1 | 10/2008 | Cargill et al. | |
| 2008/0300228 | A1* | 12/2008 | Cerri et al. | 514/172 |

FOREIGN PATENT DOCUMENTS

| WO | 03/018745 | 3/2003 |
| WO | 2006/031955 | 6/2006 |
| WO | 2007/060206 | 5/2007 |
| WO | 2010/018855 | 9/2010 |

OTHER PUBLICATIONS

NCBI website dbSNP database ss85330593 Submitted date Dec. 4, 2007.*
Ferrandi. Journal of Cardiovascular Pharmacology. 2002. 40: 881-889.*
Wall. Nature Reviews—Genetics. 2002. 4: 587-59.*
Pal. The Prostate. 2009. 69:1548-1556.*
Zill. Molecular Psychiatry. 2004. 9: 1030-1036.*
Furstenwerth. Critical Care Medicine. 2013. 41(7): e140.*
Takahashi (Hypertension Research. 2011. 34: 1147-1160.*
Cluster Report for rs2345088 (retrieved on Nov. 21, 2013 from: < http://www.ncbi.nlm.nih.gov/projects/SNP/snp_ref.cgi?rs=2345088>).*
Cluster Report for rs16877182 (retrieved on Nov. 21, 2013 from: < http://www.ncbi.nlm.nih.gov/projects/SNP/snp_ref.cgi?rs=16877182>).*
Cluster Report for rs1689522 (retrieved on Nov. 21, 2013 from: < http://www.ncbi.nlm.nih.gov/projects/SNP/snp_ref.cgi?rs=16893522>).*
Cluster Report for rs2461911 (retrieved on Nov. 21, 2013 from: < http://www.ncbi.nlm.nih.gov/projects/SNP/snp_ref.cgi?rs=2461911>).*
Cluster Report for rs5013093 (retrieved on Nov. 21, 2013 from: < http://www.ncbi.nlm.nih.gov/projects/SNP/snp_ref.cgi?rs=5013093>).*
Cluster Report for rs12513375 (retrieved on Nov. 21, 2013 from: < http://www.ncbi.nlm.nih.gov/projects/SNP/snp_ref.cgi?rs=12513375>).*
Winnicka. Acta Poloniae Pharmaceutica—Drug Research. 2005. 62(1): 75-79.*
Clinical Trial NCT00415038. Retrieved on May 13, 2015 from the internet: https://clinicaltrials.gov/ct2/show/record/NCT00415038.*
PCT International Search Report for PCT/EP2010/065589 in the name of Rostaquo S.p.A. et al. Mail Date: May 24, 2011.
PCT Written Opinion for PCT/EP2010/065589 in the name of Rostaquo S.p.A. et al. Mail Date: Feb. 9, 2012.
PCT International Preliminary Report on Patentability for PCT/EP2010/065589 in the name of Rostaquo S.p.A. et al. Mail Date: Mar. 14, 2012.
European Search Report for 09177111.3-1216 in the name of Rostaquo S.p.A. et al. completed on Jul. 16, 2010.
Ferrari, P. et al. "Rostafuroxin: an ouabain antagonist that corrects renal and vascular Na+—K+—ATPase alterations in ouabain and adducin-dependent hypertension", *Am J Physiol Regulatory Integrative Comp Physiol*, 290:529-535, Mar. 1, 2006.

(Continued)

*Primary Examiner* — Joseph G Dauner
(74) *Attorney, Agent, or Firm* — Steinfl & Bruno, LLP

(57) ABSTRACT

Methods and systems are provided herein that are based on the effects of genetic variations on the biological activities associated to rostafuroxin in an individual. In particular, compositions, methods and systems are herein described that are based on an indentified influence on an individual response to rostafuroxin of one or more polymorphisms in an intergenic or intragenic region of a gene selected from the group consisting of KCNS3, THSD7A, FAM46A, LOC389970, HLA-G, and TTC29, and/or a genetic variation in linkage disequilibrium therewith.

25 Claims, 10 Drawing Sheets

(56) References Cited

OTHER PUBLICATIONS

Staessen, J.A. et al., "Ouabain and Adducin for Specific Intervention on Sodium in HyperTension (OASIS-HT): design of a pharmacogenomic dose-finding study", *Pharmacogenomics*, vol. 6. No. 7, Jan. 1, 2005, pp. 755-775.
Staessen, J.A. et al., "Adducin and hypertension", 2005, *Pharmacogenomics*, vol. 6 No. 7, pp. 665-669.
Bianchi, G. et al, Two point mutations within the adducin genes are involved in blood pressure variation. Proc Natl Acad Sci USA 91: 3999-4003, 1994.
Casari, G. et al, Association of the adducin locus with essential hypertension. Hypertension 25: 320-326, 1995.
Bianchi, G. et al, Genetic variations of tubular sodium reabsorption leading to "primary" hypertension: from gene polymorphism to clinical symptoms, Am J Physiol Regul Integr Comp Physiol 289: R1536-R1549, 2005.
Manunta, P. et al, Relationships among endogenous ouabain, alpha-adducin polymorphisms and renal sodium handling in primary hypertension, J. Hypertens. 26 (5) (2008) 914-920.
Manunta, P. et al, Endogenous ouabain in cardiovascular function and disease, J. Hypertens. 27 (2009) 9-18.
Castellano, M. et al, E. Alpha-adducin gene polymorphism and cardiovascular phenotypes in a general population. J Hypertens 15: 1707-1710, 1997.
Beeks, E. et al, alpha-Adducin.Gly460Trp polymorphism and renal hemodynamics in essential hypertension. Hypertension 44: 419-423,2004.
Grant, F.D. et al, Low-renin hypertension, altered sodium homeostasis, and an aplha-adducin polymorphism. Hypertension 39:191-196 2002.
Psaty, B.M. et al, Diuretic therapy, the alpha-adducin gene variant, and the risk of myocardial infarction or stroke in persons with treated hypertension. JAMA 287: 1680-1689, 2002.
Sugimoto, K. et al, Alpha-adducin Gly460Trp polymorphism is associated with low renin hypertension in younger subjects in the Ohasama study. J Hypertens 20: 1779-1784, 2002.
Alam, S. et al, The 460Trp polymorphism of the human alpha-adducin gene is not associated with isolated systolic hypertension in elderly Australian Caucasians. J.Hum Hypertens 14: 199-203, 2000.
Allayee, H. et al, Genome scan for blood pressure in Dutch dyslipidemic families reveals linkage to a locus on chromosome 4p. Hypertension 38:773-778, 2001.
Bray M.S. et al, Association and linkage analysis of the alpha-adducin gene and blood pressure. Am J Hypertens 13: 699-703, 2000.
Busch, C.P. et al, the ADD1 G460W polymorphism is not associated with variation in blood pressure in Canadian Oji-Cree. J Hum Genet 44: 225-229, 1999.
Chu, S.L. et al, Linkage analysis of twelve candidate gene loci regulating water and sodium metabolism and membrane ion transport in essential hypertension. Hypertens Res 25: 635-639, 2002.
Ciechanowicz, A. et al, Lack of association between Gly460Trp polymorphism of alpha-adducin gene and salt sensitivity of blood pressure in Polish hypertensives. Kidney Blood Press Res 24: 201-206, 2001.
Clark, C.J. et al, Alpha-adducin and angiotensin I-converting enzyme polymorphisms in essential hypertension. Hypertension 36: 990-994, 2000.
He, X. et al, Linkage analysis of five candidate genes and essential hypertension in 106 Chinese nuclear families. J Hum Hypertens 17: 69-72, 2003.
He, X. et al, Alpha-Adducin gene and essential hypertension in China. Clin Exp Hypertens 23: 579-589, 2001.
Ishikawa, K. et al, No association between alpha-adducin 460 polymorphism and essential hypertension in a Japanese population. Am J Hypertens 11: 502-506 1998.
Kamitani, A. et al, Human alpha-adducin gene, blood pressure, and sodium metabolism. Hypertension 32: 138-143, 1998.
Kato, N. et al, Lack of association between the alpha-adducin locus and essential hypertension in the Japanese population. Hypertension 31:730-733, 1998.
Larson, N. et al, Lack of association of 3 functional gene variants with hypertension in African Americans. Hypertension 35: 1297-1300, 2000.
Morrison, A.C. et al, Atherosclerosis Risk in Communities Study. G-protein beta3 subunit and alpha-adducin polymorphisms and risk of subclinical and clinical stroke. Stroke 32: 822-829, 2001.
Niu, T. et al, Linkage analysis of candidate genes and gene-gene interactions in chinese hypertensive sib pairs. Hypertension 33: 1332-1337, 1999.
Niu, W. Q. et al, Lack of association between alpha-adducin G460W polymorphism and hypertension:evidence from a case-control study and a meta-analysis. J Hum Hypertension 2010; 24(7): 467-474.
Persu, A. et al, Influence of Ace (I/D) and G460W polymorphism of alpha-adducin in autosomal dominant polycystic kidney disease. Nephrol Dial Transplant 18: 2032-2038, 2003.
Province, M.A. et al, Association between the alpha-adducin gene and hypertension in the HyperGEN study. Am J Hypertens 13: 710-718 2000.
Ramu, P. et al, Gly 460Trp polymorphism and the Add1 gene and essential hypertension in an Indian population: a meta-analysis on hypertension risk. Indian J Human Genti 2010; 16:8-15.
Ranade, K. et al, Lack of evidence for an association between alpha-adducin and blood pressure regulation in Asian populations. Am J Hypertens 13: 704-709, 2000.
Turner, S.T. et al, Effects of endothelial nitric oxide synthase, _-adducin, and other candidate gene polymorphisms on blood pressure response to hydrochlorothiazide. Am J Hypertens 16: 834-839 2003.
Schork, N.J. et al, Lack of association between a biallelic polymorphism in the adducin gene and blood pressure in whites and African Americans. Am J Hypertens 13: 693-698, 2000.
Wang, W.Y. et al, The Gly460Trp variant of alpha-adducin is not associated with hypertension in white Anglo-Australians. Am J Hypertens 12: 632-636, 1999.
Gomez-Sanchez, E.P. et al, Is the circulating ouabain-like compound ouabain ? Am J Hypertension 1994; 7: 647-650.
Doris, P.A. et al, Ouabain production by cultured adrenal cells. Endocrinology 1996; 137:533-539.
Lewis, L.K. et al, Ouabain is not detectable in human plasma. Hypertension 1994; 24: 549-555.
Kelly, R.A. et al, Is ouabain the endogenous digitalis? Circulation 1992; 86: 694-697.
Nicholls, M.G. et al, Ouabain: a new steroid hormone? Lancet 1995; 346: 1381-1382.
Doris, P.A. et al, Endogenous sodium pump inhibiyotrs and blood pressure regulation: an update on recent progress. Proc Soc Exp Biol Med 1998; 218: 156-157.
Nicholls, G.M. et al, Ouabain, a circulating hormone secreted by adrenals is pivotak in cardiovascular disease. Fact or fantasy? J Hypertension 2009; 27: 3-8.
Bernini G. et al Endogenous digitalis-like factor and ouabain immunoreactyivity in adrenalectomized patients and normal subjects after acute prolonged salt loading. Am J Hypertension 1998; 11: 1-7.
Notification of the First Office Action for CN 201080047339.7 in the name of Rostaquo S.p.A. et al. mailed on Mar. 14, 2013 (English + Chinese).
Official Action for JP2012-534642 in the name of Rostaquo S.p.A mailed on Oct. 23, 2012 (English + Japanese).
Doris, P.A. et al. Is ouabain an authentic endogenous mammalian substance derived from the adrenals? Hypertension 1994; 23: 632-638.
Ferrandi, M., et al., Ouabain-dependent Signaling in Caveolae as a Novel Therapeutic Target for Hypertension, Cell. and Mol. Biol. 2006, 52: 15-18.
Manunta, P., et al. Adducin polymorphisms and the treatment of hypertension, Pharmacogenomics 2007, 8: 465-472.
Watanabe, Y., et al., Accumulation of common polymorphisms is associated with development of hypertension: a 12-year follow-up from Ohasama study, Hypertension Research 2010, 33: 129-134.
EPO official communication on Aug. 8, 2012 for EP20100807525, 3 pages.
XP008163978, Database EMBL [Online] Sep. 26, 1999, "*Homo sapiens* BAC clone CTD-3073A19 from 7, complete sequence",

(56) References Cited

OTHER PUBLICATIONS retrieved from EBI accession No. EM-SSTD:AC010908 Database accession No. AC010908, 41 pages.
Purcell S, Neale B, Todd-Brown K, Thomas L, Ferreira MA, Bender D., "PLINK: A Tool Set for Whole-Genome Association and Population-Based Linkage Analyses", Am. J. Hum Gen, 2007; vol. 81, pp. 559-575.
"2003 European Society of Hypertension-European Society of Cardiology guidelines for the management of arterial hypertension. Guidelines Committee", Journal of Hypertension. 21(6), pp. 1011-1053, Jun. 2003.
Bianchi, G. et al., Pharmacogenomics of primary hypertension—the lessons from the past to look toward the future, *Pharmacogenomics*, 2003, vol. 4, No. 3, pp. 279-296.
Blaufox, M.D. et al., Effect of dietary change on the return of hypertension after withdrawal of prolonged antihypertensive therapy (DISH), *J. Hypertens*. 1984, 2 (suppl. 3), pp. 179-181.
Chevillard, C. et al, Cardiovascular actions and tissue-converting enzyme inhibitory effects of chronic enalapril and trandolapril treatment of spontaneously hypertensive rats, *J. Cardiovasc. Pharamcol*. 1989, vol. 14, pp. 297-301.
Devlin, B. et al., Genomic Control in the Extreme, *Nature Genetics* 2004, vol. 36, No. 11, pp. 1129-1130.
Dukacz, S.A.W. et al., The persistent effect of long-term enalapril on pressure natriuresis in spontaneously hypertensive rats, *Am. J. Physiol. Renal Physiol*. 1997, 273 o 42:F104-F112.
Fagerberg, B. et al., Withdrawal of antihypertensive drug treatment: time-course for redevelopment of hypertension and effects upon left ventricular mass. *J. Hypertens* 1992, vol. 10, pp. 587-593.
Farquharson, C.A.J. et al. Gradual reactivation over time of vascular tissue angiotensin I to angiotensin II conversion during chronic lisinopril therapy in chronic heart failure, *J. Am. Coll. Cardiol*. 2002, vol. 39, No. 5, pp. 767-775.
Ferrari, P. et al., PST2238: A New Antihypertensive Compound that Antagonizes the Long-Term Pressor Effect of Ouabain, *J. of Pharmacol. Exp. Ther*. 1998, vol. 285, pp. 83-94.
Ferrari, P. et al., PST 2238: a new antihypertensive compound that modulates Na, K-ATPase in genetic hypertension, *J. Pharmacol. Exp. Ther*., 1999, vol. 288, No. 3, pp. 1074-1083.
Ferrari, P. et al., PST 2238: a new antihypertensive compound that modulates Na+,K+-ATPase and antagonizes the pressor effect of OLF, *Cardiovasc Drug Rev*. 1999, vol. 17, No. 1, pp. 39-57.
Fletcher, A.E. et al., The effect of withdrawing antihypertensive therapy: a review, *J. Hypertens*, 1988, vol. 6, pp. 431-436.
Guerrero, El. et al., Cardiovascular effects of nebivolol in spontaneously hypertensive rats persist after treatment withdrawal, *J. Hypertens* 2006, vol. 24, pp. 151-158.
Guidance for Industry: Pharmacogenomics data submission, *FDA report*, Mar. 2005, http://www.fda.gov/cder/guidance/index.htm.
Ho, Gyf, et al., Plasma renin predicts success of antihypertensive drug withdrawal, *American Journal Hypertens* 1994, vol. 7, pp. 679-684.
Levinson, P.D. et al, Persistence of normal blood pressure after withdrawal of drug treatment in mild hypertension, *Arch Int. Med.* 1982, vol. 142, pp. 2265-2268.
microRNA.org—Targets and Expression (retrieved on Oct. 3, 2012). Retrieved from the internet: <URL: http://www.microrna.org/microrna/home.do>.
Nelson, M.R. et al., Short-term predictors of maintenance of normotension after withdrawal of antihypertensive drugs in the second Australian national blood pressure study (ANBP2). *American Journal Hypertens* 2003, vol. 16, pp. 39-45.
O'Brien, E. et al., European Society of Hypertension recommendations for conventional, ambulatory and home blood pressure measurement, European Society of Hypertension Working Group on Blood Pressure Monitoring, *Journal of Hypertension*, May 2003, vol. 21, No. 5, pp. 821-848.
Page IH, Dustan HP, Persistence of normal blood pressure after discontinuting treatment in hypertensive patients, *Circulation* 1962, vol. 25, pp. 433-436.
Paull, J.R.A. et al., Persistent cardiovascular effects of chronic renin-angiotensin system inhibition following withdrawal in adult spontaneously hypertensive rats, *J. Hypertens* 2001, vol. 19, pp. 1393-1402.
Phase I HapMap, The International HapMap Consortium, *A Haplotype Map of the Human Genome* 2005, 2005, vol. 437, pp. 1299-1320.
Phase II HapMap, The international HapMap Consortium, A second generation human haplotype map of over 3.1 million SNPs, *Nature* 2007, vol. 449, pp. 851-861.
Pheasant, M. et al., Raising the estimate of functional human sequences, *Genome Res*. Sep. 2007, vol. 17, No. 9, pp. 1245-1253.
Phillips, P.C., Epistasis the essential role of gene interactions in the structure and evolution of genetic systems, *Nat. Rev. Genet.* 2008, vol. 9, pp. 855-867.
Potkin, S. et al., Genome-wide Strategies for Discovering genetic Influences on Cognition and Cognitive Disorders: Methodological Consideration, Submitted to *Cognitive Psychiatry Cogn. Neuropsychiatry*, 2009, vol. 14(4-5), pp. 391-418.
Purcell, S. et al., PLINK: A Tool Set for Whole-Genome Association Analysis, Center for Human Gentic Research, 2007, powerpoint, 40 pages.
Quadri, L. et al., 17β-(3-Furyl)-5β-androstane-3β,14β, 17α-triol (PST 2238). A Very Potent Antihypertensive Agent with a Novel Mechanism of Action, *Journal of Medicinal Chemistry*, May 23, 1997, vol. 40, No. 11, pp. 1561-1564.
Ressom, H.W. et al., Classification algorithms for phenotype prediction in genomics and proteomics, *Front Biosci*. 2008, vol. 1, No. 13, pp. 691-708.
Steemers, F.J. et al., Illumine, Inc. *Pharmacogenomics*, 2005, vol. 6, pp. 777-782.
Swart, S. et al., Plasma rennin in long-term diuretic treatment of hypertension: effect of discontinuation and restarting therapy, *Clin. Sci.* 1982, vol. 63, pp. 121-125.
Takata, Y. et al., Comparison of withdrawing antihypertensive therapy between diuretics and angiotensin converting enzyme inhibitors in essential hypertensives, *American Heart Journal* 1992, vol. 124, pp. 1574-1580.
The database of polymorphic miRNA-target interactions from Patrocles, (retrieved on Oct. 3, 2012). Retrieved from the internet: <URL:http://www.patrocles.org>.
The Wellcome Trust Case Control Consortium, Genome-wide association study of 14,000 cases of seven common diseases and 3,000 shared controls, *Nature* 2007, vol. 447, pp. 661-678.
Unger, T. et al., Persistent tissue converting enzyme inhibition following chronic treatment with Hoe498 and MK421 in spontaneously hypertensive rats, *J. Cardiovasc Pharmacol*. 1985, vol. 7, pp. 36-41.
Veterans Administration Cooperative Study Group on Antihypertensive Agents, Return of elevated blood pressure after withdrawl of antihypertensive drugs, *Circulation* 1975, vol. 51, pp. 1107-1113.
Wellcome Trust Sanger Institute (retrieved on Oct. 3, 2012). Retrieved from the internet: <URL: http://www.sanger.ac.uk/>.
Wigginton, J.E. et al., A note on exact tests of Hardy-Weinberg equilibrium, *Am. J. Hum Genet*. 2005, vol. 76, pp. 887-893.
Zanchetti, A. et al., The dilemma of placebo controlled studies: scientific evidence, guidelines, ethics and regulatory recommendations, *J. Hypertens* 2009, vol. 27, pp. 1-2.
Final Office Action for Japanese Patent Application No. 2012-534642 in the name of Rostaquo S.p.A mailed on Sep. 17, 2013 (English translation only).
Staessen et al., Main results of the Ouabain and Adducin for Specific Intervention on Sodium in Hypertension Trial (OASIS-HT): a randomized placebo-controlled phase-2 dose-finding study of rostafuroxin, Trials 2011, 12: 1-14.
English translation of Official Action for Eurasian application 201270574 filed on Oct. 18, 2010 in the name of Rostaquo S.P.A.
Fedorova et al., Endogenous Cardiotonic Steroids: *Clinical Perspectives., Arterial Hypertension*, 2008, 14(3), pp. 220, 223, 227, 228.

\* cited by examiner

1) ANOVA analysis of rs2461911 for placebo group:

| rs2461911 | Mean | Std. Dev. | Freq. |
|---|---|---|---|
| 1 | 2.2166667 | 10.168268 | 6 |
| 2 | -6.7055556 | 11.987897 | 36 |
| 3 | -9.4923076 | 10.596815 | 52 |
| Total | -7.6776596 | 11.390603 | 94 |

Analysis of Variance

| Source | SS | df | MS | F | Prob > F |
|---|---|---|---|---|---|
| Between groups | 792.638933 | 2 | 396.319467 | 3.20 | 0.0454 |
| Within groups | 11273.7243 | 91 | 123.88708 | | |
| Total | 12066.3632 | 93 | 129.745841 | | |

2) ANOVA analysis of rs2461911 for therapy group:

| rs2461911 | Mean | Std. Dev. | Freq. |
|---|---|---|---|
| 1 | -20.6 | 12.67024 | 5 |
| 2 | -7.9238095 | 12.361344 | 42 |
| 3 | -2.7211539 | 10.96131 | 52 |
| Total | -5.8313131 | 12.294097 | 99 |

Analysis of Variance

| Source | SS | df | MS | F | Prob > F |
|---|---|---|---|---|---|
| Between groups | 1777.46998 | 2 | 888.734988 | 6.55 | 0.0022 |
| Within groups | 13034.7227 | 96 | 135.778362 | | |
| Total | 14812.1927 | 98 | 151.144824 | | |

FIG. 6

| Response to treatments | Profile 4 | Profile 8 | Profile 9 |
|---|---|---|---|
| | rs16893522<br>rs5013093<br>rs2345088<br>rs2461911<br>rs16877182<br>rs12513375 | Profile 4<br>MDR2- HSD18<br>LSS2- MDR2<br>LSS2- ADD1<br>HSD19-rs430948<br>MDR2- rs213112<br>ADD2- rs105029<br>LSS2-WNK | Profile 4<br>MDR2- HSD18<br>LSS2- MDR2<br>HSD19- rs473903<br>HSD19- rs430948<br>ADD2- rs105029<br>LSS2-WNK |
| pvalue | 0.000 | 0.000 | 0.000 |
| OddsRatio | 14.64 | 32.62 | 69.75 |
| sensitivity (se) % | 54.5 | 82 | 82 |
| PPV % | 78.3 | 93 | 96 |
| Correctly % | 79.8 | 83 | 85 |
| # true R | 18/33 | 29/33 | 31/33 |
| # true NR | 61/66 | 54/66 | 54/66 |
| DSBP5-0 Therapy (mmHg) mean ± SE (n) | -18.74 ± 1.8 | -15.2 ± 1.5 | -15.2 ± 1.5 |
| Treated with low doses | -23.12 ± 3.2 (10) | -17.9 ± 2.05 (22) | -18.0 ± 2.0 (22) |
| Treated with high doses | -15.2 ± 3.0 (13) | -12.6 ± 2.4 (19) | -12.3 ± 2.2 (21) |
| DSBP5-0 Placebo (mmHg) mean | -1.14 | -2.57 | -2.64 |
| Losartan | -11.37 | -11.63 | -11.43 |
| HCTZ | -12.34 | -11.36 | -11.95 |
| Patients with profile treated / placebo | 23 / 28 | 41 / 43 | 43 / 44 |
| Patients with profile | 51 | 84 | 87 |
| Patients with profile (%) (196 patients) | 26% | 42.8% | 44.4% |

FIG. 8

| N | Gene Symbol | Chr | Gene name |
|---|---|---|---|
| 1 | ACE1 | 17 | angiotensin I converting enzyme (peptidyl-dipeptidase A) 1 |
| 2 | ACE2 | X | angiotensin I converting enzyme (peptidyl-dipeptidase A) 2 |
| 3 | ACTA1 | 1 | actin, alpha 1, skeletal muscle |
| 4 | ACTA2 | 10 | actin, alpha 2, smooth muscle, aorta |
| 5 | ACTN1 | 14 | actinin, alpha 1 |
| 6 | ADRA1A | 8 | adrenergic, alpha-1A-, receptor |
| 7 | ADRA2B | 2 | adrenergic, alpha-2B-, receptor |
| 8 | ADRB1 | 10 | adrenergic, beta-1-, receptor |
| 9 | ADRB2 | 5 | adrenergic, beta-2-, receptor |
| 10 | ADRB3 | 8 | adrenergic, beta-3-, receptor |
| 11 | AGT | 1 | angiotensinogen |
| 12 | AGTR1 | 3 | angiotensin II receptor, type 1 |
| 13 | AGTR2 | X | angiotensin II receptor, type 2 |
| 14 | AQP2 | 12 | aquaporin 2 |
| 15 | ATP1A1 | 1 | ATPase, Na+/K+ transporting, alpha 1 polypeptide |
| 16 | ATP1A2 | 1 | ATPase, Na+/K+ transporting, alpha 2 (+) polypeptide |
| 17 | ATP1A3 | 19 | ATPase, Na+/K+ transporting, alpha 3 (+) polypeptide |
| 18 | ATP1A4 | 1 | ATPase, Na+/K+ transporting, alpha 4 (+) polypeptide |
| 19 | ATP1B1 | 1 | ATPase, Na+/K+ transporting, beta 1 polypeptide |
| 20 | ATP1B2 | 17 | ATPase, Na+/K+ transporting, beta 2 polypeptide |
| 21 | ATP1B3 | 3 | ATPase, Na+/K+ transporting, beta 3 polypeptide |
| 22 | ATP1B4 | X | ATPase, Na+/K+ transporting, beta 4 polypeptide |
| 23 | BSND | 1 | Bartter syndrome, infantile, with sensorineural deafness |
| 24 | CLCNKA | 1 | chloride channel Ka |
| 25 | CLCNKB | 1 | chloride channel Kb |
| 26 | CLTA | 12 | clathrin, light chain (Lca) |
| 27 | CLTB | 4 | clathrin, light chain (Lcb) |
| 28 | CLTC | 17 | clathrin, heavy chain (Hc) |
| 29 | CLTCL1 | 22 | clathrin, heavy polypeptide-like 1 |
| 30 | CYP11B2 | 8 | cytochrome P450, family 11, subfamily B, polypeptide 2 |
| 31 | DRD1 | 5 | dopamine receptor D1 |
| 32 | DRD3 | 3 | dopamine receptor D3 |
| 33 | DRD4 | 11 | dopamine receptor D4 |
| 34 | DRD5 | 4 | dopamine receptor D5 |
| 35 | FXYD1 | 19 | FXYD domain containing ion transport regulator 1 |
| 36 | FXYD2 | 11 | FXYD domain containing ion transport regulator 2 |
| 37 | FXYD3 | 19 | FXYD domain containing ion transport regulator 3 |
| 38 | FXYD4 | 10 | FXYD domain containing ion transport regulator 4 |
| 39 | FXYD5 | 19 | FXYD domain containing ion transport regulator 5 |
| 40 | FXYD6 | 11 | FXYD domain containing ion transport regulator 6 |
| 41 | FXYD7 | 19 | FXYD domain containing ion transport regulator 7 |
| 42 | FXYD8 | X | FXYD domain containing ion transport regulator 8 |
| 43 | FYN | 6 | FYN oncogene related to SRC, FGR, YES [ |
| 44 | GNB3 | 12 | guanine nucleotide binding protein (G protein), beta polypeptide 3 |
| 45 | KCNJ1 | 11 | potassium inwardly-rectifying channel, subfamily J, member 1 (ROMK) |
| 46 | LYN | 8 | v-yes-1 Yamaguchi sarcoma viral related oncogene homolog |
| 47 | NCL | 2 | nucleolin |
| 48 | NEDD4 | 15 | neural precursor cell expressed, developmentally down-regulated 4 |
| 49 | NEDD4L | 18 | neural precursor cell expressed, developmentally down-regulated 4-like |
| 50 | NKAIN1 | 1 | Na+/K+ transporting ATPase interacting 1 |
| 51 | NKAIN2 | 6 | Na+/K+ transporting ATPase interacting 2 |
| 52 | NKAIN3 | 8 | Na+/K+ transporting ATPase interacting 3 |
| 53 | NKAIN4 | 20 | Na+/K+ transporting ATPase interacting 4 |
| 54 | NOS3 | 7 | nitric oxide synthase 3 (endothelial cell) |
| 55 | NPHS1 | 19 | nephrosis 1, congenital, Finnish type (nephrin) |
| 56 | NPHS2 | 1 | nephrosis 2, idiopathic, steroid-resistant (podocin) |
| 57 | PKD1 | 16 | polycystic kidney disease 1 (autosomal dominant) |
| 58 | PKD2 | 4 | polycystic kidney disease 2 (autosomal dominant) |
| 59 | REN | 1 | renin |
| 60 | RFX1 | 19 | regulatory factor X, 1 |
| 61 | RPH3A | 12 | rabphilin 3A homolog (mouse) |
| 62 | RPH3AL | 17 | rabphilin 3A-like (without C2 domains) |
| 63 | SCNN1A | 12 | sodium channel, nonvoltage-gated 1 alpha |
| 64 | SCNN1B | 16 | sodium channel, nonvoltage-gated 1, beta |
| 65 | SCNN1D | 1 | sodium channel, nonvoltage-gated 1, delta |
| 66 | SGK1 | 6 | serum/glucocorticoid regulated kinase 1 |
| 67 | SLC12A1 | 15 | solute carrier family 12 (sodium/potassium/chloride transporters), member 1 |
| 68 | SLC12A3 | 16 | solute carrier family 12 (sodium/chloride transporters), member 3 |
| 69 | SLC8A1 | 2 | solute carrier family 8 (sodium/calcium exchanger), member 1 |
| 70 | SYNPO | 5 | synaptopodin |
| 71 | SRC | 20 | v-src sarcoma (Schmidt-Ruppin A-2) viral oncogene homolog (avian) |
| 72 | TJP1 | 15 | tight junction protein 1 (zona occludens 1) |
| 73 | UMOD | 16 | uromodulin |
| 74 | WNK1 | 12 | WNK lysine deficient protein kinase 1 |
| 75 | WNK4 | 17 | WNK lysine deficient protein kinase 4 |

FIG. 9

Efficacy and safety data for new Antihypertensive Therapies: comparison between Traditional and Innovative Pharmacogenomic Approaches

| Parameter | Traditional | Pharmacogenomic (Rostafuroxin data) |
|---|---|---|
| Antihypertensive Efficacy ($\Delta$ Systolic BP mmHg, minus placebo) | -6 / -12 | -14 / -23 |
| Superiority among Drug Classes ($\Delta$ SBP, mmHg, in never treated patients) | 0 / -3 | -5 / -11 |
| Reduction of CV complications | 20-30% | not jet assessed, but expected to be superior * |
| Safety ratio (in preclinical models) | 1:20 – 1:40 | > 1: 10.000 | n.b. The comparison between the traditional and new approach, considers similar treatment duration and basal BP levels of the patients.

* the improved prevention of CV complications is expected due to the better BP control and the selective targeting of the genetic alterations (gene profile) responsible for the CV complications.

FIG. 10

METHODS AND SYSTEMS FOR PHARMACOGENOMIC TREATMENT OF CARDIOVASCULAR CONDITIONS

CROSS REFERENCE TO RELATED APPLICATIONS

This application is the U.S. national stage of International Application PCT/EP2010/065589 filed on Oct. 18, 2010, which, in turn, claims priority to U.S. provisional Application Ser. 61/253,020 entitled "Methods and Systems for Pharmacogenomic Treatment of Cardiovascular Conditions" filed on Oct. 19, 2009 and to EP application S/N 09177111.3 entitled "Methods and Systems for Pharmacogenomic Treatment of Cardiovascular Conditions" filed on Nov. 25, 2009, the disclosure of each of which is herein incorporated by reference in its entirety.

FIELD

The present disclosure relates to a class of compounds formed by 17β-(3-furyl)-5β-androstane-3β,14β,17α-triol, and derivatives thereof, herein collectively indicated as rostafuroxin.

BACKGROUND

Rostafuroxin is a compound known to have a biological activity in individuals. In particular, rostafuroxin has been shown to be active on the cardiovascular system of individuals and is under development for the treatment of cardiovascular disorders, such as arterial hypertension and related organ complications, including but not limited to cardiac failure, coronary heart disease (CHD) stroke and renal failure.

More particularly, rostafuroxin has been shown to be a compound that normalizes blood pressure and alterations in the Na—K pump and Src caused by, but not only, either ouabain or genetic variations in genes coding for the cytoskeletal adducin such as ADD1, ADD2, ADD3.

Additionally, rostafuroxin has been shown to be capable of normalizing the alterations of the podocyte proteins causing excessive proteinuria, glomerulosclerosis and renal failure and antagonizing the biological processes (neoitima formation and negative remodeling) causing arterial stenosis after arteriotomy and angioplasty.

SUMMARY

Provided herein are methods and systems that, allow, in several embodiments, therapeutic and/or analytical uses of rostafuroxin based on the influence of genetic variations on an individual's responses to rostafuroxin.

In particular, compositions, methods and systems are herein described that are based on an indentified influence on an individual response to rostafuroxin of one or more polymorphisms in an intergenic or intragenic region of a gene selected from the group consisting of KCNS3, THSD7A, FAM46A, LOC389970, HLA-G, and TTC29, and/or a genetic variation in linkage disequilibrium therewith. Said regions were not previously known to be correlated in any way to a cardiovascular condition, genetic predisposition or drug response in humans.

More particularly, compositions, methods and systems herein described are based on the identified influence on an individual response to rostafuroxin of one or more polymorphisms selected from the groups consisting of rs2345088, rs16877182, rs16893522, rs2461911, rs5013093, and rs12513375 (herein also called core SNPs), and/or a genetic variation in linkage disequilibrium therewith.

According to a first aspect, rostafuroxin for use in treatment or prevention of a cardiovascular condition in an individual is described, wherein the individual has been selected to be a carrier of at least one polymorphism selected from the groups consisting of rs2345088, rs16877182, rs16893522, rs2461911, rs5013093, and rs12513375, and/or a genetic variation in linkage disequilibrium therewith. In an embodiment, a method for treating or preventing a cardiovascular condition in an individual is described. The method comprises administering or prescribing rostafuroxin to said individual, wherein said individual has been determined to be a carrier of at least one polymorphism selected from the group consisting of rs2345088, rs16877182, rs16893522, rs2461911, rs5013093, and rs12513375, and/or a genetic variation in linkage disequilibrium therewith.

According to a second aspect, rostafuroxin for use as a medicament in a dosage of in a dosage of from 0.005 mg/day to 5 mg/day is described. In particular, the use of rostafuroxin in a dosage of from 0.005 mg/day to 5 mg/day is described for treating an individual wherein the individual has been selected to have a genotype comprising at least one of rs2345088, rs16877182, rs16893522, rs2461911, rs5013093, and rs12513375 and/or a genetic variation in linkage disequilibrium therewith. In particular, in an embodiment a method for treating an individual with rostafuroxin is described. The method comprises: administering or prescribing rostafuroxin to the individual in a dosage of from 0.05 mg/day to 5 mg/day, and in particular 0.05 mg/day to 0.5 mg/day, wherein the individual has been determined to have a genotype comprising at least one of rs2345088, rs16877182, rs16893522, rs2461911, rs5013093, and rs12513375, and/or a genetic variation in linkage disequilibrium therewith.

According to a third aspect, a method and system for evaluating a therapy with rostafuroxin for an individual are disclosed. The method comprises detecting in the individual sequence information for at least one polymorphism selected from the group consisting of rs2345088, rs16877182, rs16893522, rs2461911, rs5013093, and rs12513375, and/or a genetic variation in linkage disequilibrium therewith; and determining the therapy with rostafuroxin in the individual based on the detected sequence information. In particular, the sequence information can be detected from an isolated DNA sample of the individual or in other isolated samples of the individual suitable to provide sequence information. The system comprises a probe for at least one polymorphism selected from the group consisting of rs2345088, rs16877182, rs16893522, rs2461911, rs5013093, and rs12513375, and/or a genetic variation in linkage disequilibrium therewith; and a pharmaceutical composition comprising rostafuroxin in a dosage of from 0.005 mg to 5 mg/kg and in particular 0.005 mg/day to 0.5 mg/day, and a pharmaceutically acceptable vehicle.

According to a fourth aspect, a method and system for predicting a response to rostafuroxin in an individual are disclosed. The method comprises: detecting a genotype in the individual for an intergenic or intragenic region of a gene selected from the group consisting of KCNS3, THSD7A, FAM46A, LOC389970, HLA-G, and TTC29, and comparing the detected genotype with previously identified genotypes associated with a known response to rostafuroxin, the previously identified genotypes comprising at least one polymorphism selected from the group consisting of rs2345088, rs16877182, rs16893522, rs2461911, rs5013093, and rs12513375. The system comprises a probe for at least one polymorphism selected from the group consisting of rs2345088, rs16877182, rs16893522, rs2461911, rs5013093, and rs12513375 and a look-up table associating results of probes hybridization and previously identified genotypes. In particular, detecting the genotype can be performed from an isolated DNA sample of the individual or in other isolated samples of the individual suitable to provide information on the genotype. In the method and system, if the genotype identified in the individual is the same genotype associated with the rostafuroxin response, the response of the individual to rostafuroxin is predicted to be the known response.

According to a fifth aspect, a method and system for detecting a single nucleotide polymorphism (SNP) in an intergenic or intragenic region of a gene selected from the group consisting of KCNS3, THSD7A, FAM46A, LOC389970, HLA-G, and TTC29 are disclosed. In particular, detecting the genotype can be performed from an isolated DNA sample of the individual or in other isolated samples of the individual suitable to provide information on the genotype. The system comprises an isolated polynucleotide which specifically hybridizes to a nucleic acid molecule containing a single nucleotide polymorphism (SNP) in any one of the nucleotide sequences SEQ ID NO: 1, SEQ ID NO: 3, SEQ ID NO: 5, SEQ ID NO: 7, SEQ ID NO: 9 and SEQ ID NO: 11, a buffer, and an enzyme. The method comprises contacting genomic fragments comprising intergenic or intragenic regions of a gene selected from the group consisting of KCNS3, THSD7A, FAM46A, LOC389970, HLA-G, and TTC29 with a single base specific probe for at least one of the nucleotide sequences from SEQ ID NO:1, SEQ ID NO: 3, SEQ ID NO: 5, SEQ ID NO: 7, SEQ ID NO: 9 and SEQ ID NO:11 or a portion thereof. In particular, the contacting can be performed on isolated genomic fragment of the individual or in other isolated samples of the individual suitable to provide information on genomic fragments.

According to an sixth aspect, an isolated nucleic acid molecule comprising at least about 100 contiguous nucleotides wherein one of the nucleotides is a single nucleotide polymorphism (SNP) selected from any one of the nucleotide sequences in SEQ ID NO:2, SEQ ID NO: 4, SEQ ID NO: 6, SEQ ID NO: 8, SEQ ID NO: 10, and SEQ ID NO: 12, or a complement thereof.

According to a seventh aspect, a method and system for identifying an agent useful in therapeutically or prophylactically treating a cardiovascular condition are disclosed.

The method comprises providing a candidate agent; administering the candidate agent to an individual carrying at least one polymorphism selected from the group consisting of rs2345088, rs16877182, rs16893522, rs2461911, rs5013093, and rs12513375, and/or a genetic variation in linkage disequilibrium therewith; and detecting the individual response to said candidate agent.

The methods and systems herein described allow in several embodiments increasing the rate of success of the therapy for a cardiovascular condition, in particular for hypertension, from the present 30-40% to about 80%.

The methods and systems herein described in several embodiments allow increasing a rate of success of the therapy for a cardiovascular condition, in particular for hypertension, in never treated individuals.

The methods and systems herein described can be used in several embodiments to reduce the rate of adverse events and side effects as compared with the available therapies by selecting the responder individuals and reducing the effective dosages and as consequence of the possible unwanted side effects.

The methods and systems herein described can be applied in connection with any application, such as medical, diagnostic, cosmetic and pharmacological applications associated with any activity of rostafuroxin in an individual.

The details of one or more embodiments of the disclosure are set forth in the accompanying drawings and the description below. Other features, objects, and advantages will be apparent from the description and drawings, and from the claims.

BRIEF DESCRIPTION OF THE FIGURES

The accompanying drawings, which are incorporated into and constitute a part of this specification, illustrate one or more embodiments of the present disclosure and, together with the detailed description and examples, serve to explain the principles and implementations of the disclosure.

FIG. 2 shows a diagram illustration the distribution of blood pressure changes (DSBP5_0) after 5 weeks of treatment with rostafuroxin shown in FIG. 1B subdivided in tertiles.

FIG. 3 shows the top two axis of variation of Principal Component Analysis (PCA1 and PCA2) of Eigensoft for 193 patients to illustrate the genetic relatedness among individuals. Each point represents an individual. In the plot, a mild heterogeneous clusterization of individuals distributed around zero is detectable.

FIG. 5 shows diagrams each reporting the interaction between different genotypes of rs8899 and rs4678 with respect to blood pressure changes (DSBP5_0) in individuals treated with rostafuroxin and placebo as indicated.

FIG. 6 shows an exemplary univariate analysis performed to select genotypes affecting response to rostafuroxin according to some embodiments herein disclosed.

FIG. 8 shows a summary of exemplary data related to genetic profiles according to some embodiments herein described.

FIG. 9 shows a summary of selected genes related to the vascular, renal and nervous modulation of blood pressure according to some embodiments herein described.

FIG. 10 shows data concerning the efficacy and safety of traditional and pharmacogenomic approaches.

DETAILED DESCRIPTION

Figure 1:
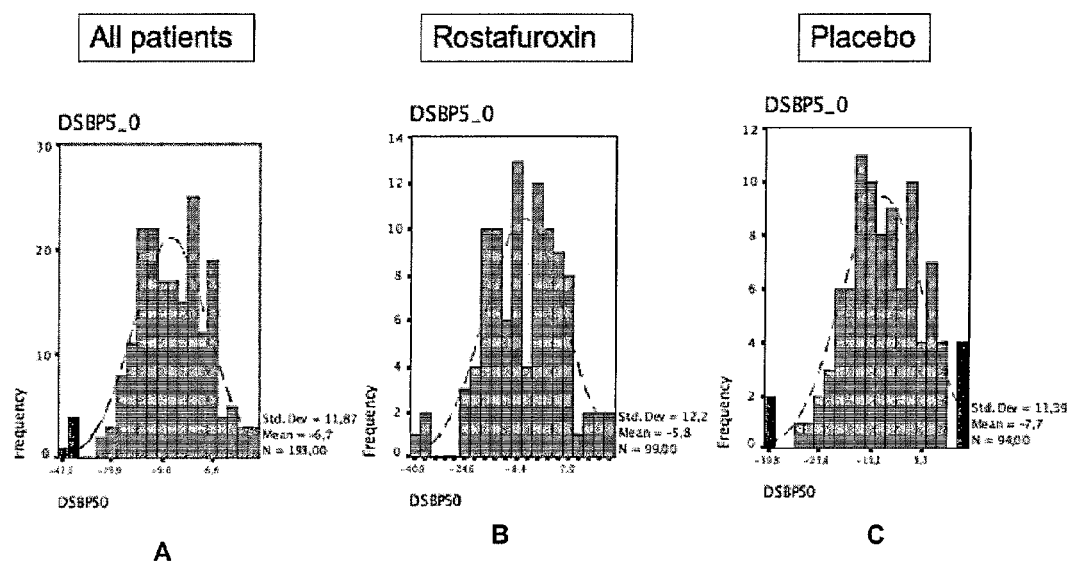
FIG. 1 shows a Gaussian distribution detected in connection with a genetic descriptive analysis performed on individuals treated with rostafuroxin and placebo. In particular, Panel A shows a diagram illustrating the distribution of blood pressure changes (DSBP5_0) in individuals after 5 weeks of treatment with rostafuroxin and placebo or both (all patients). Panel B shows a diagram illustrating the distribution of blood pressure changes (DSBP5_0) in individuals after 5 weeks of treatment with rostafuroxin (rostafuroxin). Panel C shows a diagram illustrating the distribution of blood pressure changes (DSBP5_0) in individuals after 5 weeks of treatment with placebo (Placebo).

Methods and systems are provided herein that are based on the effects of genetic variations on the biological activity associated to rostafuroxin in an individual.

In particular, methods and systems herein provided are based on polymorphisms in an intergenic or intragenic region of a gene selected from the group consisting of KCNS3, THSD7A, FAM46A, LOC389970, HLA-G, and TTC29, and/or a genetic variation in linkage disequilibrium therewith.

More particularly, compositions, methods and systems herein described are based on the identified influence on an individual response to rostafuroxin of one or more polymorphisms selected from the groups consisting of rs2345088, rs16877182, rs16893522, rs2461911, rs5013093, and rs12513375, and/or a genetic variation in linkage disequilibrium therewith.

The wording "genetic variation" or "polymorphism" as used herein indicates genetic diversity in a population of individuals and in particular is an altered state of a region of DNA or chromosome. Exemplary polymorphisms comprise VNTR (variable number of tandem repeats, also known as minisatellite and microsatellite), base pairs substitutions, base pairs insertion, base pairs deletion, changes in karyotype (aneuploidy, polyploidy) and chromosome rearrangements (deletion, translocation, inversion).

The term "rostafuroxin" as used herein indicates any one of the compounds of a class formed by 17β-(3-furyl)-5β-androstane-3β,14β,17α-triol, and derivatives thereof. More particularly, the rostafuroxin compounds comprise compounds of formula I.

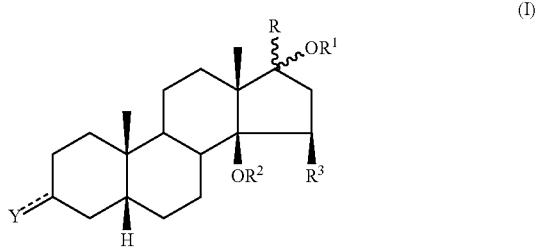

(I)

wherein: the symbol ⌇ means that the substituents in position 17 can have an α or β configuration; the symbol --- represents a single or a double bond; Y is oxygen or guanidinoimino, when --- in position 3 is a double bond; Y is hydroxy, $OR^4$ or $SR^4$, when --- in position 3 is a single bond and can have an α or β configuration;

R is an unsubstituted or substituted 3-furyl or 4-pyridazinyl group;

$R^1$ is hydrogen; methyl; ethyl or n-propyl substituted by OH or $NR^5R^6$;

$R^2$ is hydrogen or together to $R^3$ is a bond of an oxirane ring;

$R^3$ is hydrogen or together to $R^2$ is a bond of an oxirane ring;

$R^4$ is hydrogen; methyl; C2-C6 alkyl or C3-C6 alkenyl or C2-C6 acyl, these alkyl, alkenyl and acyl groups being unsubstituted or substituted by a quaternary ammonium group or one or more $OR^7$, $NR^8R^9$, formyl, amidino, guanidinoimino or by $NR^8R^9$ and hydroxy;

$R^5$, $R^6$ are independently hydrogen; methyl; C2-C6 alkyl unsubstituted or substituted by one $NR^{10}R^{11}$, or $NR^{10}R^{11}$ and hydroxy, or $R^5$ and $R^6$ taken together with the nitrogen atom form an unsubstituted or substituted saturated or unsaturated penta- or hexa-monoheterocyclic ring, optionally containing another heteroatom chosen from oxygen or sulfur or nitrogen;

$R^7$ is hydrogen, methyl or C2-C4 alkyl, this alkyl being unsubstituted or substituted by one or more $NR^{10}R^{11}$ or by $NR^{10}R^{11}$ and hydroxy;

$R^8$, $R^9$ are independently hydrogen; methyl; C2-C6 alkyl or C3-C6 alkenyl, these alkyl and alkenyl groups being unsubstituted or substituted by one or more $NR^{10}R^{11}$, or $NR^{10}R^{11}$ and hydroxy, or $R^8$ and $R^9$ taken together with the nitrogen atom form an unsubstituted or substituted saturated or unsaturated penta- or hexa-monoheterocyclic ring, optionally containing another heteroatom chosen from oxygen or sulfur or nitrogen, or $R^8$ is hydrogen and $R^9$ is amidino;

$R^{10}$, $R^{11}$ are independently hydrogen, C1-C6 alkyl, or $R^{10}$ and $R^{11}$, taken together with the nitrogen atom form a saturated or unsaturated penta- or hexa-monoheterocyclic ring.

In particular, the term rostafuroxin as used herein includes all the possible stereoisomers, in particular Z and E isomers, optical isomers and their mixtures as well as metabolites and the metabolic precursors of the compounds of formula (I). The term "derivative" as used herein indicates a chemically modified compound of formula (I) which retains at least one of the biological activities associated with the compound of Formula (I). Chemical modifications can include, for example, replacement of hydrogen by an alkyl, acyl, hydroxyl, or amino group and additional modifications identifiable by a skilled person.

Reference is also made to U.S. Pat. No. 5,591,734, Bianchi al., 2003, and Quadri et al 1997 [Ref. 4, 5] and the related supporting information, (each incorporated herein by reference in its entirety) which describe the synthesis and biological activity of rostafuroxin compounds.

Additional biological activities associated to rostafuroxin are described in Ferrari P. et al., 1998 [Ref. 6], also incorporated herein by reference in its entirety.

The wording "biological activity" as used herein with reference to rostafuroxin indicates the quality or state of any effects of rostafuroxin, or relating to rostafuroxin on a living matter. Biological activities of rostafuroxin include but are not limited to selective inhibition of the ouabain hypertensive effect, normalization of alterations in the Na—K pump and Src caused by ouabain, and normalization in forms of hypertension sustained by the concomitant increase of endogenous ouabain levels and alterations in the Na—K pump and Src. In particular, biological activities of rostafuroxin comprise a selective antagonism of the hypertensive effect associated to the genetic variations of genes coding for adducin or other enzymes involved in synthesis and transport of endogenous ouabain, normalization of alterations in the Na—K pump and Src caused by adducin genetic variations [Ref. 1, 2, 3], and normalization in forms of hypertension sustained by the concomitant effects of adducin genetic variations and alterations in the Na—K pump and Src. Biological activities of rostafuroxin also include but are not limited to the normalization of the alterations of the podocyte proteins causing excessive proteinuria, glomerulosclerosis and renal failure and antagonism of the biological processes causing arterial stenosis after arteriotomy and angioplasty and additional activities identifiable by a skilled person upon reading of the present disclosure.

As described in the present disclosure, the biological activities associated with rostafuroxin are affected by genetic variations in individuals so that in several embodiments the treatment with rostafuroxin results in an enhanced biological activity compared to the biological activity elicited in individuals not presenting the genetic variations.

Additionally, since rostafuroxin activity is dosage-dependent, methods and systems herein described allow in several embodiments effective administration of rostafuroxin to the individuals carrying the genetic variations with corresponding decrease of possible side effects.

The detectable biological activities associated with rostafuroxin in an individual define the response of the individual to rostafuroxin. The biological activities can be detected with methods and techniques identifiable by a skilled person, which include but are not limited to detection of biomarkers associated with the biological activity, and detection of a vital signs and other clinical information associated to the biological activity in the individual with particular reference to the blood pressure of the individual.

In several embodiments of the present disclosure administration of rostafuroxin to an individual carrying a genetic variation according to the present disclosure results in an improved response to rostafuroxin in the individual.

In particular an "improved response" in the sense of the present description indicates the enhanced activities of rostafuroxin as detected in the individual, which in several embodiments comprise at least one of prevention of hypertension, reduction of blood pressure, normalization of blood pressure, and prevention of the cardiovascular, renal, vascular, ocular and nervous damages or complications associated to hypertension. In particular, an improved response can be defined, in several embodiments, by an average office systolic blood pressure decrease from about 23 mmHg to about 12 mmHg compared to blood pressure measured in the individual prior to starting the treatment.

In several embodiments an improved response can be defined by an average decrease of the office systolic blood pressure and/or nightly blood pressure of the individuals of at least about 15 and about 9 mmHg, respectively compared to blood pressure measured in the individual prior to starting the treatment. Also in several embodiments an improved response can be defined by an average decrease in the office systolic blood pressure and/or nightly blood pressure at least one of the office systolic blood pressure decrease that is significantly greater (e.g. 40% or more higher) than a corresponding average decrease detected in the individual following administration of other antihypertensive such as Hydrochlorothiazide (HCTZ) or Losartan.

The term "average decrease" or "average drop" as used herein with reference to blood pressure indicates a decrease that is a measure of the middle or expected value of a set of blood pressure measurements performed on an individual in a predetermined amount of time determined according to medical guidelines in view of the blood pressure to be detected (e.g. nightly or office blood pressure). The specific timing of the measurements and the descriptive statistics that can be used as a measurement of the central tendency of the blood pressure measurements to calculate the average decrease are identifiable by a skilled person upon reading of the present disclosure.

The term "office blood pressure" as used herein indicates the blood pressure level measured by the physician in his ambulatory by suitable equipment such as a sphygmomanometer, an electronic BP recorder or additional equipment identifiable by a skilled person.

The term "nightly blood pressure" as used here indicates the blood pressure levels recorded nightly typically from 12 p.m. to 6 a.m. by suitable equipment, such as an electronic blood pressure recorder in particular according to Holter's method) or additional equipment identifiable by a skilled person.

The term "hydrochlorothiazide" as used herein indicates a first line diuretic drug of the thiazide class that acts by inhibiting the kidneys' ability to retain water and has formula 6-chloro-1,1-dioxo-3,4-dihydro-2H-1,2,4-benzothiadiazine-7-sulfonamide.

The term "losartan" as used herein indicates an angiotensin II receptor antagonist drug used mainly to treat high blood pressure having formula (2-butyl-4-chloro-1-{[2'-(1H-tetrazol-5-yl)biphenyl-4-yl]methyl}-1H-imidazol-5-yl)methanol.

According to the present disclosure the response of an individual to rostafuroxin is affected by certain genetic variations and in particular by single nucleotide polymorphisms that are detectable in the individual's genotype. The term "single nucleotide polymorphism" or "SNP" as used herein indicates a genetic variation formed by single base pair substitution also called a point mutation. According to the present disclosure, SNPs or point mutations can be located in an intragenic region of a gene (e.g. in intronic or exonic regions of the gene) or intergenic regions flanking a gene, and that are typically composed of genomic regions with regulatory functions or with unknown function.

The term "individuals" as used herein indicates a single biological organism such as higher animals and in particular vertebrates such as mammals and more particularly human beings.

The term "genotype" as used herein indicates the combination of alleles located on homologous chromosomes for each of the genetic variations considered. In particular, in the present disclosure genotype 1 (g1) for a specific gene or position indicates the association to the homozygous less frequent genotype for that specific gene or position, genotype (g2) for a specific gene or position indicates the association to the heterozygous genotype for that specific gene or position, and genotype 3 (g3) for a specific gene or position indicates association to the homozygous more frequent genotype for that specific gene or position.

In several embodiments, the genetic variations affecting rostafuroxin activities in an individual comprise at least one SNP selected from the group consisting of rs2345088, rs16877182, rs16893522, rs2461911, rs5013093, and rs12513375 15 (herein also indicated as "core SNPs") and/or a genetic variation in linkage disequilibrium therewith. The core SNPs as well as other SNPs are herein often indicated using the dbSNP rsiD identifiers established by the National Center for Biotechnology Information (NCBI) and available for example at the NCBI SNPs project website ncbi.nlm.nih.gov/projects/SNP/at the date of filing of the present application. The wording 'linkage disequilibrium" as used herein indicates the nonrandom association of alleles at two or more loci, not necessarily on the same chromosome, and relates to a situation in which some combinations of alleles or genetic markers occur more or less frequently in a population than would be expected from a random formation of haplotypes from alleles based on their frequencies. Non-random associations between polymorphisms at different loci are measured by the degree of linkage disequilibrium (LD). Genetic variations in linkage disequilibrium indicated in the present disclosure have degree of linkage disequilibrium r2 ranging from 0.9-1 and can be identified by a skilled person using GenBank sources upon reading of the present disclosure.

In some embodiments, the effects of genetic variations on an individual's response to rostafuroxin are considered in methods to perform or evaluate a rostafuroxin therapy herein described. The terms "therapy", "therapeutic" therapeutically" and related as used herein indicate an item of or relating to the treatment or prevention of a condition in an individual, and in particular when referred to rostafuroxin, indicate an item of or relating to the treatment or prevention of a condition associated to any biological activity associated to rostafuroxin in the individual.

The term "condition" as used herein indicates as usually the physical status of the body of an individual (as a whole or of one or more of its parts) that does not conform to a physical status of the individual (as a whole or of one or more of its parts) that is associated with a state of complete physical, mental and possibly social well-being. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The wording "associated to" as used herein with reference to two items indicates a relation between the two items such that the occurrence of a first item is accompanied by the occurrence of the second item, which includes but is not limited to a cause-effect relation and sign/symptoms-disease relation.

Conditions associated to a biological activity which is associated to rostafuroxin in an individual include but are not limited to cardiovascular conditions (e.g. hypertension, including primary hypertension, cardiac hypertrophy, increased vascular resistances and arterial restenosis) renal failure, glomerulosclerosis, proteinuria, polycistic renal disease, retinal damage, cerebrovascular disorders, Meniere syndrome, cognitive disorders, bipolar disorders and cardiovascular complications associated to primary hypertension such as cardiac failure, stroke, ischemia, retinal damage an additional conditions identifiable by the skilled person.

The wording "primary hypertension" indicates a clinical condition affecting 25-30% of the adult population in industrialized societies and through its cardiac, cerebral and renal complications is responsible for a large proportion of health burdens and costs, and includes grade I, II, III, IV of hypertension based on the level of blood pressure and the presence of the associated vascular, retinal complications identifiable by a skilled person.

The term "treatment" as used herein indicates any activity that is part of a medical care for, or that deals with, a condition medically or surgically. The term "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

In particular, in some embodiments, information concerning SNPs in an individual's genotype is used as a method for treating or preventing a cardiovascular condition in the individual. In those embodiments rostafuroxin is administered or prescribed to the individual who has been determined to be a carrier of at least one polymorphism selected from the group consisting of the core SNPs rs2345088, rs16877182, rs16893522, rs2461911, rs5013093, and rs12513375 or of a genetic variation in linkage disequilibrium therewith.

In particular, in several embodiments, individuals carrying one or more of the core SNPs exhibit an improved response to rostafuroxin in the individual that can be calculated on the basis to the quantitative phenotype formed by the average decrease in blood pressure in an individual measured following therapy with respect to treatment with placebo (DSBP5_0) of at least 15 mmHg as illustrated extensively in the Examples section.

Based on a quantitative phenotype DSBP5_0 in several embodiments, individuals carrying one or more of the core SNPs exhibit an improved response defined by a magnitude of the average blood pressure drop (significantly compared to values before treatment) obtained with rostafuroxin that is about 40% or more and in particular about 40% to 50% or more, than the average blood pressure drop obtained with other antihypertensive agents such as HCTZ or Losartan in never treated patients.

In several embodiments, individuals carrying one or more of the core SNPs exhibit an improved response to rostafuroxin in the individual that can be calculated on the basis to the quantitative phenotype formed by the average decrease in nightly blood pressure in an individual measured following therapy with respect to treatment with placebo (DSBP5_0) of at least 9 mmHg as illustrated extensively in the Examples section.

Additionally, since the DSBP5_0 is the quantitative phenotype of the statistical and experimental analysis reported in the Examples section, the improved response to rostafuroxin defined by average drop in blood pressure is considered representative of any improved response defined by any biological activities associated to rostafuroxin that are detectable using biomarkers or clinical information other than blood pressure measurement. Therefore improved responses defined by biological activities of rostafuroxin detectable using biomarkers or clinical information other than blood pressure measurement are comprised within the scope of the present disclosure and identifiable by a skilled person.

In some embodiments of the methods and systems herein described an improved response to rostafuroxin is achieved by administering or prescribing rostafuroxin to an individual carrying one or more of the following core SNPs: nucleotide C or T in position 18079898 of chromosome 6 (rs2345088), nucleotide C or T in position 11753617 of chromosome 7 (rs16877182), nucleotide G or A in position 82560511 of chromosome 6 (rs16893522), nucleotide G or A in position 57078480 of chromosome 10 (rs2461911), nucleotide C or T in position 29928565 in chromosome 6 (rs5013093), and nucleotide T or G in position 148244380 of chromosome 4 (rs12513375).

In some embodiments of the methods and systems herein described rostafuroxin is administered or prescribed to an individual who is a carrier of at least one of the following genotypes alone or in combination with each other: genotype TT or genotype 1 for rs2345088, genotype C/T or genotype 2 for rs16877182, genotype AA or genotype 1 for rs16893522, genotype AA or genotype 1 for rs2461911, genotype TT or genotype 1 for rs5013093, and genotype TT or genotype 1 for rs12513375.

In particular, the presence of at least one relevant genotype for any of the above listed SNPs, alone or in combination one with the other is associated to a DSBNP5_0 average systolic blood pressure decrease in the individuals ranging from 23 to 12 mmHg according to the doses or the combination of genotypes (profiles see Examples section).

In several embodiments, one or more of the core SNPs and/or genetic variations in linkage disequilibrium therewith can be associated with one or more additional genetic variations also affecting the response to rostafuroxin in an individual genetic variations also affecting the response to rostafuroxin in an individual and that are exemplified by the SNPs identified as CAND 1, CAND 2 and GWS described in details in the Examples section. In particular the additional genetic variations affecting the response to rostafuroxin in the individuals comprise groups of genes directly or indirectly involved in Adducin expression and Endogenous Ouabain (EO) synthesis and transport Those genes include but are not limited to CAND 1 genes such as ADD1, ADD2, ADD3, LSS, CYP11A1, HSD3B1-2 SLCO4C1, MDR1 and related polymorphisms.

In several embodiments of the methods and systems herein described an improved response to rostafuroxin is detected in connection with administering or prescribing rostafuroxin to an individual carrying at least one of the following additional relevant CAND 1 SNPs alone or in combination with the core SNPs: rs4961, rs4984, rs3731566, rs914247, and rs1045642 and/or of a genetic variation in linkage disequilibrium therewith.

In particular, in some embodiments of the methods and systems herein described an improved response to rostafuroxin is detected in connection with administering or prescribing rostafuroxin to an individual who is a carrier of at least one of the following CAND 1 genotypes alone or in combination with a genotype for core SNPs: GT for rs4961, CT for rs4984, AG for rs3731566, GA for rs914247, and TC for rs1045642. In particular, an improved response to rostafuroxin is detected in connection with administering or prescribing rostafuroxin to an individual who is a carrier of CAND 1 genotype AA for rs914247.

In several embodiments of the methods and systems herein described an improved response to rostafuroxin is detected in connection with administering or prescribing rostafuroxin to an individual carrying at least one of the following additional relevant CAND 2 SNPs alone or in combination with the core SNPs: rs242093, rs1996396, rs10503806, rs13251780, rs17430706, rs10102024, rs526302, rs544104, rs3102087, rs5183, rs3772627, rs2276736, rs2131127, rs3741559, rs2217342, rs10927888, rs6604909, rs945403, rs7117314, rs10790212, rs11216598, rs910682, rs13218316, rs4309483, rs13280307, rs4739037, rs17596774, rs2728108, rs17786456, rs7696304, rs2725222, rs17199565, rs2758152, rs1057293, rs16960712, rs759359, rs404214, rs1005213, rs17025453, rs2110923, rs1428571, rs435404, rs12908787, rs11647727, rs880054, and rs11064584 and/or of a genetic variation in linkage disequilibrium therewith.

In several embodiments of the methods and systems herein described an improved response to rostafuroxin is detected in connection with administering or prescribing rostafuroxin to an individual carrying at least one of the following additional relevant GWS SNPs alone or in combination with the core SNPs: rs12996186, rs9893372, rs7216331, rs7521668, rs188334, rs4998662, rs16893522, rs6457110, rs3893464, rs2517718, rs1362126, rs5013093, rs2345088, rs6718282, rs721207, rs2555500, rs2461911, rs8179654, rs1901139, rs2427832, rs9361863, rs1998394, ga001619, rs2275531, rs748140, rs4710592, rs2743951, rs10159569, rs3087816, rs10493940, rs16877182, rs2326912, rs1110446, rs12513375, rs17414954 or of a genetic variation in linkage disequilibrium therewith.

In some embodiments of the methods and systems herein described an improved response to rostafuroxin is detected in connection with administering or prescribing rostafuroxin to an individual carrying at least one of the following additional relevant SNPs alone or in combination with the core SNPs: Rs4961, Rs4984, Rs10923835, Rs947130, Rs914247, Rs1045642, Rs880054, Rs10502933, Rs2131127, Rs4309483, and Rs4739037 or of a genetic variation in linkage disequilibrium therewith.

More particularly, in some embodiments of the methods and systems herein described an improved response to rostafuroxin is achieved by administering or prescribing rostafuroxin to an individual carrying at least one of the following additional relevant SNPs alone or in combination with the core SNPs: nucleotide G or T for Rs4961, nucleotide G or A for Rs4984, nucleotide A or T for Rs10923835, nucleotide C or T for Rs947130, nucleotide A or G for Rs914247, nucleotide C or T for Rs1045642, nucleotide C or T for Rs880054, nucleotide C or T for Rs10502933, nucleotide C or T for Rs2131127, nucleotide C or A for Rs4309483, and nucleotide G or A for Rs4739037.

More particularly, in some embodiments of the methods and systems herein described rostafuroxin is administered or prescribed to an individual who is a carrier of at least one of the following genotypes alone or in combination with a genotype for core SNPs: genotype GT or genotype TT for. Rs4961, genotype CC for Rs4984, genotype AT or genotype TT for Rs10923835, genotype GG for Rs947130, genotype AA for Rs914247, genotype TT for Rs1045642, genotype AG or genotype GG for Rs880054, genotype CT for Rs10502933, genotype CC for Rs2131127, genotype AA for Rs4309483, and genotype GA for Rs4739037.

In particular, in several embodiments of the method for treating an individual with rostafuroxin is described. The method comprises: administering or prescribing rostafuroxin to the individual in a dosage of from 0.005 mg/day to 5 mg/day, preferably 0.01 mg/day to 1.5 mg/day, most preferably 0.05 mg/day to 0.5 mg/day. Dosage treatment can be performed on a single dose schedule or a multiple dose schedule, according to the physician judgment.

In particular, in several embodiments lower doses (such as 0.05 mg/day; 0.15 mg/day; 0.5 mg/day) can be more efficient in reducing systolic blood pressure than the high doses (1.5 mg/day; 5.0 mg/day) in the subset of individuals carrying the genetic variations herein described, with an average decrease in systolic blood pressure of approximately 18 mmHg as compared with −12 mmHg induced by high doses.

In particular, in several embodiments hypertensive individuals carrying previously identified genotypes comprising at least one polymorphism selected from the core SNPs dosage of rostafuroxin comprised from 0.05 to 0.5 mg/day produces a blood pressure drop ranging from −12 to −34 mmHg and dosages comprised from 1.5 mg/day to 5 mg/day produces a blood pressure drop ranging from −0.6 to −23 mmHg.

Accordingly, in several embodiments, individuals carrying all core SNPs low dosages provide a greater response (−23 mmHg average) with respect to high dosages (−15 mmHg average).

In several embodiments, following treatment with rostafuroxin individuals carrying genetic variations herein described exhibit a decrease in blood pressure of at least 10% compared to the detected blood pressure before rostafuroxin treatment.

In several embodiments, following treatment with rostafuroxin individuals carrying genetic variations herein described exhibit an average decrease in the office blood pressure and/or nightly blood pressure of the individual of at least about 15 and about 9 mmHg, respectively.

In several embodiments, individuals carrying genetic variations herein described exhibit a normalization of the blood pressure below 140 mmHg for the systolic blood pressure and below 90 mmHg for the diastolic blood pressure.

In several embodiments, following treatment with rostafuroxin individuals carrying genetic variations herein described exhibit an average blood pressure decrease that is about 40% higher than an average blood pressure decrease obtained with HCTZ or Losartan (see Example 2).

In methods and systems herein described rostafuroxin can be comprised compositions to be administered individually to a patient and/or that can be administered in combination with other agents, drugs or hormones. In particular, in some embodiments the medicament can also contain a pharmaceutically acceptable carrier, selected from the carriers suitable for administration of a therapeutic agent. A thorough discussion of pharmaceutically acceptable carriers is available in Remington's Pharmaceutical Sciences (Mack Pub. Co., N.J. 1991) herein incorporated by reference in its entirety.

Pharmaceutically acceptable carriers in therapeutic compositions can additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the individual.

The medicament comprising rostafuroxin can be administered in methods herein described by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, rectal means or locally on the diseased tissue after surgical operation. The compound of the invention may also be applied (coated) on the stent even incorporated into a controlled-release matrix.

In several embodiments, the expected therapeutic effects in term of treatment and prevention that follows administration of rostafuroxin in individuals carrying at least one of the core SNPs and/or genetic variation in linkage disequilibrium therewith can include but are not limited to: prevention or reduction of cardiac hypertrophy and insufficiency, cardiac ischemia, increased vascular reactivity, vascular stiffness, increased vascular thickness, renal hypertrophy, renal failure, glomerulosclerosis, proteinuria, cerebrovascular damage, stroke, cognitive disorders, retinal damage. Such effects are expected since all the above mentioned disorders are directly or indirectly consequent to the pathological increase of blood pressure (grade III and IV of hypertension) which is normalized by rostafuroxin in individuals carrying the core SNPs alone or in combination with each others, with CAND1 SNPs, CAND2 SNPs, selected GWS SNPs and/or genetic variations in linkage disequilibrium therewith. In addition, due to the ability of rostafuroxin to antagonize some mechanisms of hypertension such as increased renal sodium reabsorption and activation of the Src signal transduction pathway, organ damages other than those directly caused by high blood pressure can be prevented by the treatment. For instance, individuals carrying the ADD1 Trp460 genetic variant, for the same level of blood pressure, display a higher incidence of cardiovascular complications than carrier of the Gly460 ADD1 variant. Also hypertensive individuals with high levels of plasma ouabain display higher rate of cardiovascular complications than individuals with low ouabain plasma level but similar blood pressure levels. Even though the precise mechanisms of the increased blood pressure drop after rostafuroxin in individuals carrying at least one of the selected core SNPs are not known, they must be related to the mechanisms triggered by the molecular targets hit by rostafuroxin. As consequence, benefits beyond those related to the blood pressure drop induced by rostafuroxin are expected in individuals carrying at least one of the core SNPs genotypes.

In some embodiments, in the individuals carrying at least one of the core SNPs, dosages of rostafuroxin ranging from 0.05 to 0.15 mg/day (low doses) are expected to induce a greater blood pressure drop than higher doses such as those ranging from 1.5 to 5 mg/day (high doses). In particular, the low doses are expected to produce an average blood pressure drop of about 23 mmHg while the high doses are expected to produce an average blood pressure drop of about 15 mmHg. In addition, In the individuals carrying at least one of the core SNPs these dosages of rostafuroxin are expected to prevent the development of cardiovascular complications associated but not only to hypertension such as cardiac hypertrophy, cardiac failure, increased vascular resistances, renal failure, glomerulosclerosis, proteinuria, policistic renal disease, retinal damage, cerebrovascular disorders, Meniere syndrome, cognitive disorders, bipolar disorders.

In some embodiments, rostafuroxin treatment to an individual carrying at least one of the core SNPs can be performed in a dosage of 5 µg per day ranging from 5 µg to 50000 µg, preferably 10 µg to 15000 µg, most preferably 50 µg to 500 µg.

According to the dosages, low doses ranging from 0.05 to 0.50 mg/day (low doses) result in a higher (+50%) response in term of blood pressure drop as compared to high doses ranging from 1.5 to 5 mg/day (high doses). In addition, low doses produce a relevantly higher drop of night blood pressure as compared to high doses.

In some embodiments, administration of rostafuroxin to an individual carrying at least one of the core SNPs in combination with each other and/or with other relevant SNPs such as those included in the CAND1, 2 and GWSA SNPs (see profile 8 and 9, example 2), rostafuroxin is expected to induce an average blood pressure decrease ranging from about 8 to about 22.5 mmHg.

In some embodiments, administration of rostafuroxin to an individual carrying at least one of the core SNPs in combination with each other and in association with other relevant SNPs such as those included in the CAND1, CAND 2 and GWS SNPs (see profiles 8 and 9, Example 2), rostafuroxin is expected to induce a average blood pressure drop of the office (systolic, daily) blood pressure 23 mmHg and of the nightly blood pressure of about 9 mmHg.

In some embodiments, administration of rostafuroxin to an individual carrying at least one of the core SNPs alone or in combination with each other or additional relevant SNPs, results in an improved response to rostafuroxin if compared with the response of the individual to other hypertensive drugs such as Losartan or Hydrochlothiazide. In particular, administration of rostafuroxin to individuals carrying at least one of the core SNPs alone or in combination with each other (or additional relevant SNPs) is expected to produce a blood pressure drop at least 40% higher than those produced by Losartan or HCTZ, respectively (see Example 2) in never treated patients.

In some embodiments a method for evaluating therapy herein described comprises obtaining sequence information regarding at least one polymorphism selected from the group consisting of the core SNPs: rs16877182, rs5013093, rs2461911, rs12513375, rs16893522, rs2345088, wherein the information is predictive of rostafuroxin efficacy in the individual.

In some embodiments, sequence information can be obtained also for additional relevant genetic variations affecting the response to rostafuroxin such as SNPs of CAND1 genes, CAND2 genes and/or GWS genes, which include but are not limited to rs4961 (ADD1), rs4984 (ADD2), rs3731566 (ADD3), rs914247 (LSS2), rs1045642 (MDR2), rs10502933, rs2131127, rs4309483, rs4739037 and additional SNPs. Identifiable by a skilled person upon reading of the present disclosure (additional SNPs from profiles 8-9: rs10923835 (HSD18), rs947130 (HSD19), rs880054 (WNK1).

In some embodiments, sequence information comprise at least one of the sequences SEQ ID NO: 1, SEQ ID NO: 3, SEQ ID NO: 5, SEQ ID NO: 7, SEQ ID NO: 9 and SEQ ID NO: 11 and an improved response to rostafuroxin can be predicted with corresponding detected sequence information such as SEQ ID NO: 2, SEQ ID NO: 4, SEQ ID NO: 6, SEQ ID NO: 8, SEQ ID NO: 10 and SEQ ID NO: 12 respectively.

More particularly, in embodiments where sequence information comprise at least one of the sequences SEQ ID NO: 1, SEQ ID NO: 3, SEQ ID NO: 5, SEQ ID NO: 7, SEQ ID NO: 9 and SEQ ID NO: 11 and an improved response to rostafuroxin can be predicted with corresponding detected allelic sequence information comprising SEQ ID NOs: 13 and 14 for SEQ ID NO: 1, SEQ ID NOs: 15 and 16 for SEQ ID NO: 3, SEQ ID NOs: 17 and 18 for SEQ ID NO: 5, SEQ ID NOs: 19 and 20 for SEQ ID NO: 7, SEQ ID NOs: 21 and 22 for SEQ ID NO: 9, and SEQ ID NOs: 23 and 24 for SEQ ID NO: 11.

In several embodiments, the method comprises obtaining sequence information for at least one polymorphism selected from the group consisting of rs4961, rs4984, rs10923835, rs947130, rs914247, rs1045642, rs880054, rs10502933, rs2131127, rs4309483, and rs4739037. In particular, in several embodiments, additional relevant sequence information further comprise SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 and SEQ ID NO: 45, and an improved response to rostafuroxin can be predicted with corresponding detected sequence information such as SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 and SEQ ID NO: 46, respectively.

More particularly, in embodiments where sequence information comprise at least one of the sequences SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 and SEQ ID NO: 45, an improved response to rostafuroxin can be predicted with corresponding detected allelic sequence information comprising SEQ ID NOs: 47 and 48 for SEQ ID NO: 25, SEQ ID NOs: 49 and 50 for SEQ ID NO: 27, SEQ ID NOs: 51 and 52 for SEQ ID NO: 29, SEQ ID NOs: 53 and 54 for SEQ ID NO: 31, SEQ ID NOs: 55 and 56 for SEQ ID NO: 33, SEQ ID NOs: 57 and 58 for SEQ ID NO: 35, SEQ ID NOs: 59 and 60 for SEQ ID NO: 37, SEQ ID NOs: 61 and 62 for SEQ ID NO: 39, SEQ ID NOs: 63 and 64 for SEQ ID NO: 41, SEQ ID NOs: 65 and 66 for SEQ ID NO: 43, and SEQ ID NOs: 67 and 68 for SEQ ID NO: 45.

In particular, sequence information can be obtained using genotype analysis: GenChip from ILLUMINA or additional methods and systems identifiable by a skilled person. In some embodiments, the method for evaluating rostafuroxin therapy herein disclosed can be performed by a system that comprises probes for the core SNPs sequence information or a portion thereof such as the primers from SEQ ID NO: 35 to SEQ ID NO: 58 listed in Example 8 below.

In some embodiments, the method to evaluate treatment with rostafuroxin comprises the selection of the hypertensive patients who should be either men or women, with age of at least 18 years, of various ethnicity including Caucasian but also African, Asian or Afro-American, preferentially with, but not limited to, grade I or II of primary hypertension, untreated or on treatment with only one drug or one combination tablet containing no more than two antihypertensive agents, without severe or malignant hypertension or secondary hypertension (which includes a history of renal arterial disease), without associated conditions and no more than two additional cardiovascular risk factors, without surgery or diseases of the gastrointestinal system which might influence the absorption or hepatic clearance of rostafuroxin, not on treatment with any other investigational drug from at least 6 months before rostafuroxin administration. Patients can be treated according to the 2003 guidelines of the European Society of Hypertension and the European Society of Cardiology [Ref. 7].

Blood pressure can be monitored under ambulatory conditions according to the recommendations of the European Society of Hypertension for conventional and ambulatory blood-pressure measurement [Ref.8]. Measurement of blood pressure can be performed by employing oscillometric recorders or any other validated ambulatory recorder or sphygmomanometer. Blood pressure should be monitored at the arm after the patient has rested for at least 5 min in the sitting position. Genotype of the patients can be measured on a blood sample taken at the brachial vein. The DNA will be extracted from the blood according to standard procedure [Ref.9] or with the use of custom kit (for example Promega genomic DNA purification Cat A2360 or Qiagen PAXgene Blood DNA Kit), stored and genotyped for the SNP of interest using a selected nuclease detection assay (e.g. ABI assay on demand for allelic discrimination). In some embodiments sequence information can be derived using methods identifiable by a skilled person.

Individuals carrying at least one of the core SNPs, and in particular the selected genotype herein described, alone or in association with each other, and/or additional relevant SNPs belonging to CAND 1, CAND2 and GWS SNPs, and in particular the selected genotype herein described, and/or having related sequence information are treated with rostafuroxin by administering the substance in a defined pharmaceutical composition, once a day, by oral route, in a dosage ranging from 0.05 to 5 mg/day, preferably in the morning between 7.00 and 9.00 a.m. The treatment can last from at least 5 weeks to the entire patient's life.

In some embodiments, the effects of genetic variations on rostafuroxin activity form the basis for a method for predicting a response to rostafuroxin in an individual. The method comprises: detecting a genotype in the individual for an intergenic or intragenic region of a gene selected from the group consisting of KCNS3, THSD7A, FAM46A, LOC389970, HLA-G, and TTC29, and comparing the detected genotype with previously identified genotypes associated with a known response to rostafuroxin, the previously identified genotypes comprising at least one polymorphism selected from the group consisting of rs2345088, rs16877182, rs16893522, rs2461911, rs5013093, and rs12513375.

The term "detect" or "detection" and "detectable" as used herein indicates the determination of the existence, presence or fact of a compound, a sequence or genotype, in a limited portion of space, including but not limited to a tissue sample, a reaction mixture, a molecular complex and a substrate. A detection is "quantitative" when it refers, relates to, or involves the measurement of quantity or amount of the compound (also referred as quantitation), which includes but is not limited to any analysis designed to determine the amounts or proportions of the compound. A detection is "qualitative" when it refers, relates to, or involves identification of a quality or kind of the compound in terms of relative abundance to another target or signal, which is not quantified.

Detecting a genotype can be performed according to several techniques identifiable by a skilled person. In general the methods for single SNP analysis are PCR-RFLP analysis, DNA sequencing, Taqman assay, kinetic PCR. One of this method, the Taqman Assay (assay on demand and custom MGB probe and primer design from ABI) was used in the present report to genotype CAND1 SNPs (Example 3) and ADD1, ADD2, HSD18, HSD19, LSS2, MDR2, WNK genes (Example 4).

The assay for multiple SNP analysis utilizes several commercial platform and available or custom Gene-Chip with variable number of genes (hundreds to millions) for each chip. In the present disclosure the HumanHap 1M Duo chip genotyping Beads Chip and the Illumina Infinium II Technology was used to genotype the SNPs in Example 4 (rs10502933, rs2131127, rs4309483, rs4739037) and Examples 5 and 6.

In the method, if the genotype detected in the individual is the same genotype associated with the rostafuroxin response, the response of the individual to rostafuroxin predicted to be the known response. The term "response" as used herein, with reference to rostafuroxin, indicates any fact any action or change of condition in the individual that are associated to the administration of rostafuroxin to the individual. Exemplary response to rostafuroxin in an individual comprises blood pressure drop clinically relevant. In particular, a blood pressure drop significantly higher than that caused by placebo and specifically at least equal to 10% of the blood pressure value before treatment or able to bring the blood pressure values equal or lower than 140 mmHg for systolic or 90 mmHg for diastolic blood pressure. In some embodiments, the method can further comprise detecting, e.g. in the isolated DNA of the individual a genotype in the individual for an intergenic or intragenic region of a gene selected from the group consisting of ADD1, ADD2, ADD3, CYP11A1, HSD3B1, LSS, ABCB1/MDR1, SLCO4C; and comparing the detected genotype with previously identified genotypes associated with a known Rostafuroxin response, the previously identified genotypes comprising at least one polymorphism selected from the group consisting of rs4961, rs4984, rs3731566, rs914247, rs1045642 and/or of a genetic variation in linkage disequilibrium therewith. In some embodiments, the method can further comprise detecting a genotype in the individual for an intergenic or intragenic region of a gene selected from the group consisting of ACTN1, ADRA1A, AGTR1, AQP2, ATP1A3, CLCNKA, CLCNKB, FXYD2, FXYD6, FYN, NEDD4L, NKAIN3, PKD1, PKD2, SCNN1B, SGK1, SLC12A1, SLC8A1, TJP1, UMOD, and WNK1; and comparing the detected genotype with previously identified genotypes associated with a known Rostafuroxin response, the previously identified genotypes comprising at least one polymorphism selected from the group consisting of rs242093, rs1996396, rs10503806, rs13251780, rs17430706, rs10102024, rs526302, rs544104, rs3102087, rs5183, rs3772627, rs2276736, rs2131127, rs3741559, rs2217342, rs10927888, rs6604909, rs945403, rs7117314, rs10790212, rs11216598, rs910682, rs13218316, rs4309483, rs13280307, rs4739037, rs17596774, rs2728108, rs17786456, rs7696304, rs2725222, rs17199565, rs2758152, rs1057293, rs16960712, rs759359, rs404214, rs1005213, rs17025453, rs2110923, rs1428571, rs435404, rs12908787, rs11647727, rs880054, and rs11064584 and/or of a genetic variation in linkage disequilibrium therewith. In some embodiments, the method can further comprise detecting a genotype in the individual for an intergenic or intragenic region of a gene selected from the group consisting of ARL5A, ATP2A3, COX10, DPH5, FAIM3, FAM46A, HCG9, HLA-A, HLA-F, HLA-G, KCNS3, LOC131691, LOC389174, LOC389970, LOC642727, LOC644192, LOC649458, LOC728360, LOC728316, PIGR, RCADH5, RP3-377H14.5, SH3PXD2A, SLC30A7, THSD7A, TMEM200A, TRIM31, TTC29, and VCAM1; and comparing the detected genotype with previously identified genotypes associated with a known Rostafuroxin response, the previously identified genotypes comprising at least one polymorphism selected from the group consisting of rs12996186, rs9893372, rs7216331, rs7521668, rs188334, rs4998662, rs16893522, rs6457110, rs3893464, rs2517718, rs1362126, rs5013093, rs2345088, rs6718282, rs721207, rs2555500, rs2461911, rs8179654, rs1901139, rs2427832, rs9361863, rs1998394, ga001619, rs2275531, rs748140, rs4710592, rs2743951, rs10159569, rs3087816, rs10493940, rs16877182, rs2326912, rs1110446, rs12513375, and rs17414954 and/or of a genetic variation in linkage disequilibrium therewith.

In some embodiments, the method for predicting a response to rostafuroxin herein disclosed can be performed by a system that comprises a first component for genotyping that is applied only once for the classification of patients in responders and not responders, and a composition comprising rostafuroxin and a pharmaceutical acceptable carrier at the doses ranging from 50-500γ daily.

In some embodiments, a system for predicting a response of an individual to rostafuroxin can comprise a probe for at least one polymorphism selected from the group consisting of rs2345088, rs16877182, rs16893522, rs2461911, rs5013093, and rs12513375 and a look-up table associating results of probes hybridization and previously identified genotypes.

In some of those embodiments, the probe comprises at least one isolated polynucleotide selected from the group consisting of SEQ ID NO: 2, SEQ ID NO: 4, SEQ ID NO: 6, SEQ ID NO: 8, SEQ ID NO: 10 and SEQ ID NO: 12 or a fragment thereof, the fragment capable of specifically hybridizing a sequence complementary to SEQ ID NO: 2, SEQ ID NO: 4, SEQ ID NO: 6, SEQ ID NO: 8, SEQ ID NO: 10 or SEQ ID NO: 12.

In of those embodiments, the system can further comprise a probe for at least one polymorphism selected from the group consisting of rs4961, rs4984, rs10923835, rs947130, rs914247, rs1045642, rs880054, rs10502933, rs2131127, rs4309483, and rs4739037.

In particular, the probe can comprise at least one isolated polynucleotide selected from the group consisting of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 and SEQ ID NO: 46 or a fragment thereof, the fragment capable of specifically hybridizing a sequence complementary to SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 or SEQ ID NO: 46. In some embodiments, the probes can have a sequence selected from the group consisting of SEQ ID NO: 35 to SEQ ID NO: 58.

In several embodiments the system can comprise tubes for blood samples collection, buffers for genomic DNA extraction, DNA amplification (e.g. primers, buffer, and/or dNTP enzymes) and additional components identifiable by a skilled person.

In several embodiments, several procedures can be used for single SNP analysis comprising: a) Real-time PCR SNP genotyping with allele specific MGB probes using Pre-Designed SNP assay or custom SNP Genotyping Assay from ABI and a real-time PCR system for data analysis; b) Allele specific PCR SNP with universal energy transfer primers (Amplifluor technology) and real time PCR system for data analysis; c) PCR-RFLP analysis and agarose-gel detection; d) kinetic PCR; and e) direct sequencing. Additional procedures that are suitable to perform single SNP analysis are identifiable by a skilled person and will not be discussed in further details.

In several embodiments the systems can comprise custom services of gene-chip (micro-array) from ILLUMINA, AFFIMETRIX or ABI or other specialized companies, can be used. For our purpose the number of SNPs to include in a single gene-chip could be relative low (20-30). The main components to assemble a specific gene-chip are based on five major processes: DNA purification, PCR amplification of purified DNA with specific primer mix; fragmentation and labeling of the amplified products; hybridization of the amplified products to the microarray and staining of the bound products, scanning and analysis of the microarray.

In some embodiments, the effects of genetic variations on rostafuroxin activity form the basis for a method for identifying an individual with improved response to rostafuroxin. The method comprises detecting a single nucleotide polymorphism (SNP) in any one of the nucleotide sequences of SEQ ID NO 1, SEQ ID NO 3, SEQ ID NO 5, SEQ ID NO 7, SEQ ID NO 9, and SEQ ID NO 11 in intergenic or intragenic regions of the individuals, wherein the presence of the core SNPs is correlated with an improved response to rostafuroxin in said individual. In several embodiments additional relevant SNPs herein described can also be detected in the method for identifying an individual with improved response to rostafuroxin.

In some embodiments, the effects of genetic variations on rostafuroxin activity form the basis for a method for improving a therapeutic response to rostafuroxin in an individual with a cardiovascular condition. The method comprises administering rostafuroxin to said individual, wherein said individual has been determined to be a carrier of at least one of the core SNPs and/or of a genetic variation in linkage disequilibrium therewith.

In some embodiments, the effects of genetic variations on rostafuroxin activity form the basis for a method for treating an individual with rostafuroxin. The method comprises: obtaining information indicating the presence of the core SNPs and optionally on the additional SNPs affecting rostafuroxin response in an individual and administering rostafuroxin for the individual having a genotype associated with the improved response in a dosage ranging from 0.005 mg to 50 mg, preferably 0.01 mg to 15 mg, most preferably 0.05 mg to 5 mg.

In some embodiments, the effects of genetic variations on rostafuroxin activity form the basis for a method for treating an individual with a cardiovascular condition. The method comprises: administering or prescribing to the patient an effective amount of rostafuroxin, wherein the patient is a carrier of at least one core SNPs and/or of a genetic variation in linkage disequilibrium therewith.

In some embodiments, the cardiovascular condition is hypertension and the method for treating an individual can be performed by
a) obtaining a nucleic acid sample from an individual suffering from hypertension;
b) determining the presence in said nucleic acid sample of one or more of the polymorphisms selected from the groups consisting of: the core SNPs herein described;
c) administering a pharmaceutically active amount of rostafuroxin to the patients that have shown to possess at least one polymorphism selected from the groups consisting of the core SNPs herein described.

In methods for treating individuals herein disclosed, rostafuroxin is typically administered in the form of a pharmaceutical composition. Such compositions can be prepared in a manner well known in the pharmaceutical art and comprise at least one active compound and a vehicle. The term "vehicle" as used herein indicates any of various media acting usually as solvents, carriers, binders, diluents or excipients for a rostafuroxin compound comprised in the composition as an active ingredient. A person skilled in the art is aware of a whole variety of such solvents carrier, diluent or excipient compounds suitable to formulate a pharmaceutical composition.

rostafuroxin together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

In some embodiments rostafuroxin is administered in a "pharmaceutically effective amount". The amount of the compound actually administered will typically be determined by a physician, in the light of the relevant circumstances, including the condition to be treated, the chosen route of administration, drug combination, the age, body weight, and response of the individual patient, the severity of the patient's symptoms, and the like. Generally, an effective dose is from 0.005 mg to 50 mg, preferably 0.01 mg to 15 mg, most preferably 0.05 mg to 5 mg as single administration per day.

Compositions may be administered individually to a patient or may be administered in combination with other agents, drugs or hormones. The effective dosages of the composition to be administered to a patient range from 0.05 mg to 5 mg/day.

Depending on the intended route of delivery, rostafuroxin is preferably formulated as parenteral, topical or oral compositions, more preferably as oral formulation. The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, pre-measured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form.

Dosage treatment may be a single dose schedule or a multiple dose schedule. Liquid forms suitable for oral administration may include a suitable aqueous or non-aqueous vehicle with buffers, suspending and dispensing agents, colorants, flavors and the like.

Solid forms may include, for example, any of the following ingredients, or compounds of a similar nature: a binder such as microcrystalline cellulose, acacia, gum tragacanth, gelatine or polyvinyl-pyrrolidone; an excipient such as starch or lactose, a disintegrating agent such as alginic acid, Primogel, or potato or corn starch; a lubricant such as magnesium stearate, talc, polyethylene glycol or silica; a glidant such as colloidal silicon dioxide; a sweetening agent such as sucrose or saccharin; or a flavoring agent such as pepper-mint, methyl salicylate, or orange flavoring. The tablets may be coated according to methods well known from people skilled in the art of pharmaceutical practice.

Parenteral compositions are typically based upon injectable sterile saline or phosphate-buffered saline or other injectable carriers known in the art. As mentioned above, the compounds of formula I in such compositions are typically a minor component, frequently ranging between 0.05 to 10% by weight with the remainder being the injectable carrier and the like.

Rostafuroxin can also be administered in sustained release forms or from sustained release drug delivery systems. A description of representative sustained release materials can also be found in the incorporated materials in Remington's Pharmaceutical Sciences.

The above-described components for orally administered or parenteral compositions are merely representative. Further materials as well as processing techniques and the like are set out in Part 5 of Remington's Pharmaceutical Sciences, 20th Edition, 2000, Marck Publishing Company, Easton, Pa., which is incorporated herein by reference in its entirety.

In some embodiments, an isolated nucleic acid molecule comprising at least 100 contiguous nucleotides, is disclosed wherein one of the nucleotides is a single nucleotide polymorphism (SNP) selected in any one of the nucleotide sequences SEQ ID NO 1, SEQ ID NO 3, SEQ ID NO5, SEQ ID NO7, SEQ ID NO9 and SEQ ID NO 11, or a complement thereof.

In some embodiments, the effects of genetic variations on rostafuroxin activity form the basis for a method for identifying an agent useful in therapeutically or prophylactically treating a cardiovascular condition is disclosed.

The method comprises providing a candidate agent; administering the candidate agent to an individual carrying at least one polymorphism selected from the group consisting of rs2345088, rs16877182, rs16893522, rs2461911, rs5013093, rs12513375 or a polymorphism in linkage disequilibrium therewith and detecting the individual response to said candidate agent.

In several embodiments, the candidate agent is administered to an individual carrying also one or more of the CAND 1, CAND2 and GWS SNPs herein indicated.

In several embodiments, the method can be performed by selecting hypertensive patients and performing measurements and detection according to procedures used to evaluate treatment with rostafuroxin in individuals. In some of those embodiments, evaluating rostafuroxin treatment in an individual can be performed by obtaining sequence information regarding at least one polymorphism selected from the group consisting of rs2345088, rs16877182, rs16893522, rs2461911, rs5013093, and rs12513375 wherein the information is predictive of rostafuroxin efficacy in the individual.

In some of those embodiments, the sequence information comprises at least one of the sequences SEQ ID NO: 1, SEQ ID NO: 3, SEQ ID NO: 5, SEQ ID NO: 7, SEQ ID NO: 9 and SEQ ID NO: 11, and an improved response to rostafuroxin can be predicted with at least one corresponding detected sequence information selected from the group consisting of SEQ ID NO: 2, SEQ ID NO: 4, SEQ ID NO: 6, SEQ ID NO: 8, SEQ ID NO: 10 and SEQ ID NO: 12.

In some of those embodiments, an improved response to rostafuroxin can be predicted with at least one corresponding detected allelic sequence information selected from the group consisting of SEQ ID NOs: 13 and 14 for SEQ ID NO: 1, SEQ ID NOs: 15 and 16 for SEQ ID NO: 3, SEQ ID NOs: 17 and 18 for SEQ ID NO: 5, SEQ ID NOs: 19 and 20 for SEQ ID NO: 7, SEQ ID NOs: 21 and 22 for SEQ ID NO: 9, and SEQ ID NOs: 23 and 24 for SEQ ID NO: 11.

In some of those embodiments, the evaluating method can further comprise obtaining sequence information for at least one polymorphism selected from the group consisting of rs4961, rs4984, rs10923835, rs947130, rs914247, rs1045642, rs880054, rs10502933, rs2131127, rs4309483, and rs4739037. In particular, the sequence information can comprise at least one of the sequences SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 and SEQ ID NO: 45. For those sequence information an improved response to Rostafuroxin can be predicted with at least one corresponding detected sequence information selected from the group consisting of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 and SEQ ID NO: 46.

In some of those embodiments an improved response to Rostafuroxin can be predicted with at least one corresponding detected allelic sequence information selected from the group consisting of SEQ ID NOs: 47 and 48 for SEQ ID NO: 25, SEQ ID NOs: 49 and 50 for SEQ ID NO: 27, SEQ ID NOs: 51 and 52 for SEQ ID NO: 29, SEQ ID NOs: 53 and 54 for SEQ ID NO: 31, SEQ ID NOs: 55 and 56 for SEQ ID NO: 33, SEQ ID NOs: 57 and 58 for SEQ ID NO: 35, SEQ ID NOs: 59 and 60 for SEQ ID NO: 37, SEQ ID NOs: 61 and 62 for SEQ ID NO: 39, SEQ ID NOs: 63 and 64 for SEQ ID NO: 41, SEQ ID NOs: 65 and 66 for SEQ ID NO: 43, and SEQ ID NOs: 67 and 68 for SEQ ID NO: 45.

In some embodiments, the method for identifying an agent useful in therapeutically or prophylactically treating a cardiovascular condition herein disclosed can be performed by a system that comprises components suitable to detect and identify the relevant genetic variations as described herein.

In some embodiments, a system for detecting a single nucleotide polymorphism (SNP) in an intergenic or intragenic region of a gene selected from the group consisting of KCNS3, THSD7A, FAM46A, LOC389970, HLA-G, and TTC29, is disclosed. The system comprises an isolated polynucleotide which specifically hybridizes to a nucleic acid molecule containing a single nucleotide polymorphism (SNP) in any one of the nucleotide sequences SEQ ID NO: 1, SEQ ID NO: 3, SEQ ID NO: 5, SEQ ID NO: 7, SEQ ID NO: 9, SEQ ID NO: 11, and at least one of a buffer for the nucleic acid molecule (such as a hybridization and/or polymerization buffer), and an enzyme to be used in combination with the nucleic acid sequence for the detection of the SNP. In particular, the enzyme can be a polymerase capable of catalyzing a polymerase chain reaction for one or more of the intergenic and/or intragenic region that are investigated.

The term hybridization as used herein indicates the process of establishing a non-covalent, sequence-specific interaction between two or more complementary strands of nucleic acids into a single hybrid, which in the case of two strands is referred to as a duplex. A specific hybridization is a hybridization resulting in a specific sequence-sequence interaction. The wording "specific" "specifically" or specificity" as used herein with reference to the binding of a molecule to another refers to the recognition, contact and formation of a stable complex between the molecule and the another, together with substantially less to no recognition, contact and formation of a stable complex between each of the molecule and the another with other molecules. The term "specific" as used herein with reference to a sequence of a polynucleotide refers to the unique association of the sequence with a single polynucleotide which is the complementary sequence.

The term "polymerase chain reaction" as used herein indicates any suitable technique to amplify a single or few copies of a piece of a nucleic acid across several orders of magnitude, generating thousands to millions of copies of a particular DNA sequence. The method relies on thermal cycling, consisting of cycles of repeated heating and cooling of the reaction for nucleic acid melting and enzymatic replication of the nucleic acid.

In some embodiments, the system can also comprise an isolated polynucleotide that specifically hybridizes to a nucleic acid molecule containing a single nucleotide polymorphism (SNP) in any one of the nucleotide sequences SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 and SEQ ID NO: 45.

The systems herein disclosed can be provided in the form of kits of parts. In a kit of parts, the probes, pharmaceutical compositions and other components and a substrate are comprised in the kit independently. In particular, the probes can be included in one or more compositions, and each probe can be comprised in a composition together with a suitable vehicle carrier or auxiliary agent.

In some embodiments, buffers enzyme and suitable container can be further provided as an additional component of the kit. Additional components can include labels (a molecule capable of detection, such as radioactive isotopes, fluorophores, chemioluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like, microfluidic chip, reference standards, and additional components identifiable by a skilled person upon reading of the present disclosure. In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

In the following section the present disclosure shall be illustrated by means of some examples which are not construed to be viewed as limiting the scope of the disclosure.

EXAMPLES

A pharmacogenomic study was performed to ascertain the effect of genetic variations on an individual response to rostafuroxin. The sample for the pharmacogenomic study consisted of 342 individuals that were genotyped with the Human1M array from Illumina using Human1M Duo CHIP genotyping Bead Chip according to procedure described in [Ref. 10, 11, 12]. Among the individuals, 169 were administered the placebo treatment and 173 the active drug (rostafuroxin) in the first period (5 weeks) with demographics as in [Ref 13]. In particular, patients were randomized to one of the following oral doses of rostafuroxin: 0.05, 0.15, 0.5, 1.5, or 5 mg/day for 5 weeks. Each dose had to be compared to a placebo in a crossover design. Since previous studies demonstrated that one month of washout may be insufficient [Ref. 14-30] 193 patients that did not receive a previous treatment (NPT) were analyzed separately from the 149 previously treated.

For the above sample of individuals a genetic association analysis, was performed to associate the phenotype of the tested individuals with the SNPs detected in the individuals. The selected phenotype of interest was the blood pressure response. The SNPs selected for detection were the 1111170 SNPs on autosomal chromosomes of the individual.

The genetic analysis was performed according to a quantitative genetic association design where the phenotype of interest is a quantitative variable (QT), and the variables (factors) affecting the distribution of the phenotype of interest are SNPs, therapy (placebo, rostafuroxin) and the SNP*therapy interaction.

In particular, the quantitative phenotype selected for the statistical analyses was the difference in mmHg between the office Systolic Blood Pressure (SBP) at the end of first treatment period (SBP_5) and the office Systolic Blood Pressure at baseline after one month of run-in (SBP_0) and is herein also identified as DSBP5_0. The selected QT phenotype and other factors affecting distribution of the phenotype of interest were then analyzed according to the following quantitative trait interaction test $$Phenotype=SNP+therapy+SNP*therapy$$

as illustrated in further details below.

To perform the genetic association a descriptive statistical analysis and an inferential statistical analysis were carried out.

The descriptive statistical analysis was performed to first summarize and describe the main parameters of the data and perform quality controls.

Table 1 summarizes the statistical procedures, parameters and thresholds selected by Applicants in performing the analysis as well as the results obtained in outcome therefrom.

TABLE 1

Descriptive Statistical Analysis

| Procedure | Analysis/thresholds | Results |
|---|---|---|
| Call Rate | Number of SNPs called per sample | Mean call rate of 0.996651 for the 193 NPT subjects on 1M SNPs |
| Individual Missingness | Number of individuals with missing rate per SNP Inclusion threshold ≤10% Number of SNPs with missing rate per individual Inclusion threshold ≤10% | Individuals missing: 0 of 193 individuals were removed for low genotyping (MIND > 0.1) Locus (SNP) missingness: 6071 SNPs failed missingness test having a genotyping rate <0.9 and were not included in the analysis |
| Minor Allele Frequency | Lowest allele frequency at a specific locus observed in a particular population - MAF threshold of 0.05 | MAF < 0.05 for 258148 SNPs - excluded from the analysis |
| Hardy Weinberg equilibrium (HWE) test | HWE tested for each SNP in the whole population using the exact test, described and implemented by Wigginton et al. [Ref 31] | 2510 SNPs markers failed HWE test (p <= 0.001) SNPs not removed in view of sample composition (only cases) - departure from HWE could be indicative that association phenotype-SNPs is real causal. |
| Stratification | Principal Component Analysis (PCA) to reduce 1M SNPs dimensions allowing clustering the individuals using top axis of variation | Mild heterogeneous clusterization of individuals distributed around zero is visible (see FIG. 3) |
| | Genomic inflation factor, λ calculated as described in Devlin et al. [Ref 32] | Genomic inflation factor, λ reported is 1.005 indicating the absence of inflation due to the stratification, if compared with the lambda (1.757) of example of stratified population (population composed by Europeans, Africans and other or more than one racial category) |

Figure 2:
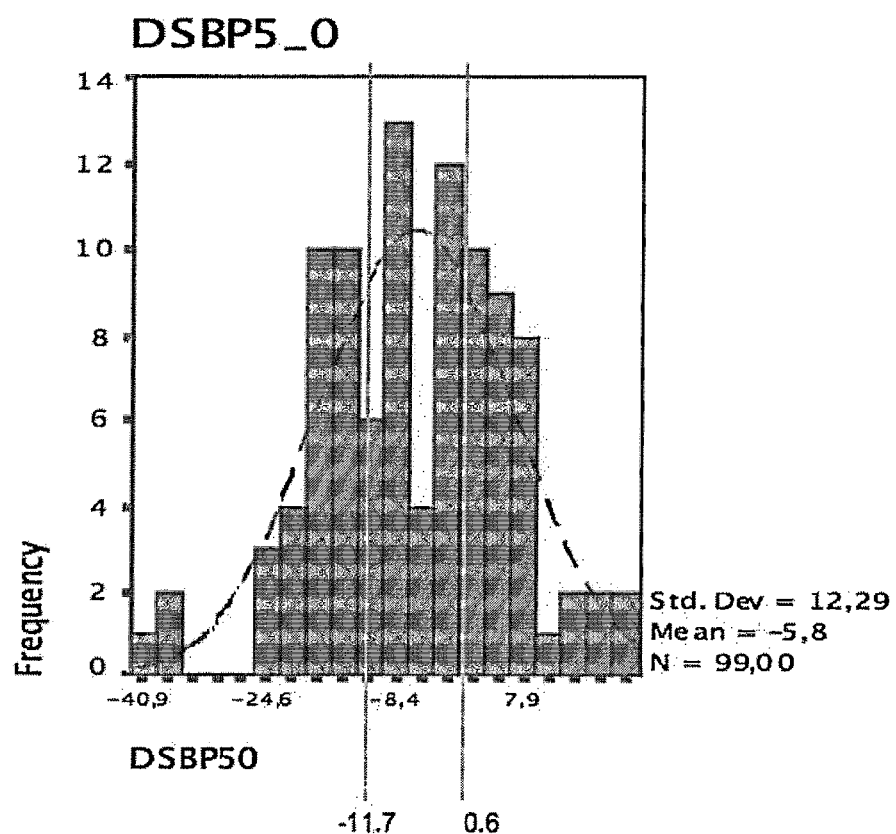
FIG. 2 shows a Gaussian distribution detected in connection with a genetic descriptive analysis performed on individuals treated with rostafuroxin. In particular
Figure 3:
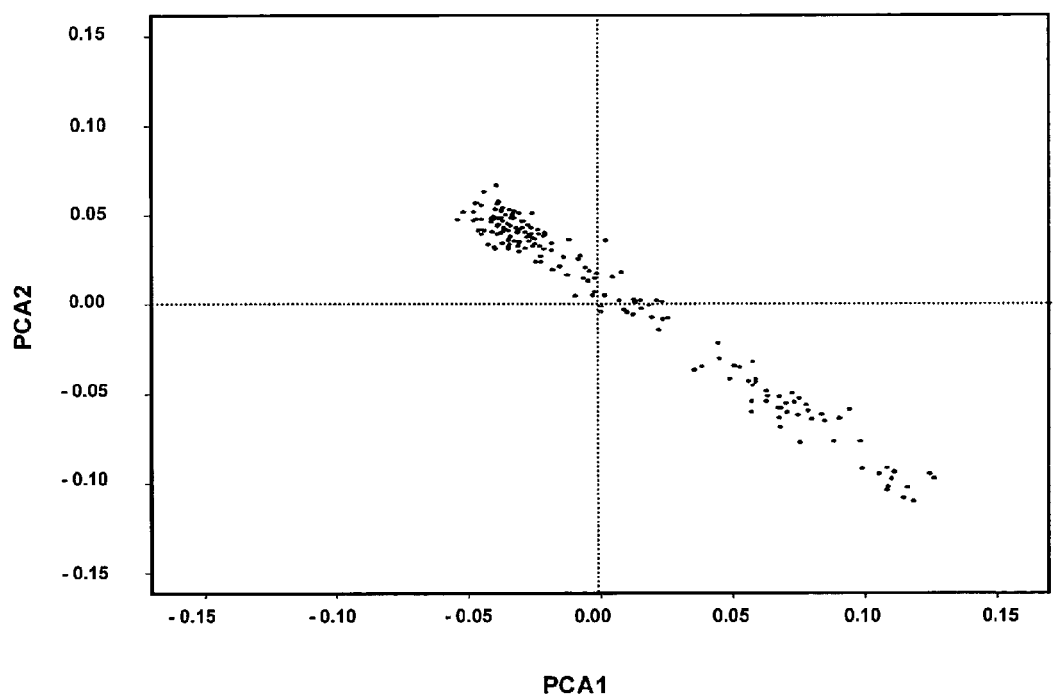
FIG. 3 shows results statistical analysis performed in connection with a genetic descriptive analysis performed on individuals treated with rostafuroxin. In particular.

The results of the genetic descriptive analysis performed are also illustrated in Table 2 and FIGS. 1, 2 and 3 in further detail.

TABLE 2

Results of Descriptive Statistical Analysis

| Patient Group | Basal SBP ± SD | Mean fall in blood pressure mmHg | Std. Err. | [95% Conf. Interval] |
|---|---|---|---|---|
| Total (193 IDs) | 150.3 +/− 7.5 | −6.73057 | .8542748 | −8.415539-5.045601 |
| Placebo (94 IDs) | 150.0 +/− 7.5 | −7.67766 | 1.174851 | −10.01068-5.344638 |
| Therapy (99 IDs) | 150.6 +/− 7.5 | −5.831313 | 1.235603 | −8.283328-3.379299 |

In particular, in Table 2 the descriptive statistics of DSBP5_0 for the entire sample and for the patients treated with placebo and rostafuroxin are listed. The rather modest basal level of SBP can be explained in view of the recruitment of patients with "mild" hypertension (SBP range 140-179 mmHg), required by the inclusion of a placebo arm. A graphic illustration of the results summarized in Table 2 is illustrated in FIG. 1 that shows the DSBP5_0 distribution in Total, Therapy and Placebo.

For the NPT group, the total genotyping rate in remaining individuals was 99.67%; 6071 SNP failed the missingness test (call rate <90%) and 258148 SNPs had MAF <0.05. After frequency and genotyping pruning 848340 SNPs remained following filtering using MAF threshold of 0.05 (data not shown).

In view of the above, Applicants selected a cut off value for the QT DSBP5_0 of ≤11.7 mmHg, relative to the lowest terzile of the distribution of DSBP5_0 (−11.7 mmHg, that is, 33 out of 99 patients) to generate a binomial phenotype variable, the response—non response to the rostafuroxin. The DSBP5_0 threshold selection was performed to provide a parameter that is indicative of both statistical and clinical relevance of the results.

A graphic representation of the results of the descriptive statistical analysis showing the selected QT threshold is illustrated in FIG. 2.

FIG. 3 illustrates the genetic relatedness among the tested individuals detected using the top axis of variation showing a mild heterogeneous clusterization of individuals distributed around zero. The assessment (and correction) of population stratification is relevant to avoid the false positive and false negative significant associations due to the presence of systematic ancestry differences.

An inferential statistical analysis was then performed using the QT calculated to detect SNPs that are significantly associated to a different response to the treatment (placebo or active drug).

TABLE 3

Inferential Statistical Analysis

| Procedure | Analysis | Selected Threshold |
|---|---|---|
| Univariate | single point analysis of SNPS considered one by one assessment performed on the quantitative trait interaction test (G * E, Gene * Environment) as implemented in gPLINK [Ref 33] Relevant parameter P value of the SNP*therapy association | P value SNP * therapy association <10$^{-4}$ |

TABLE 3-continued

Inferential Statistical Analysis

| Procedure | Analysis | Selected Threshold |
|---|---|---|
| Interaction | Interactions across tested genes analyzed to test dependence of QT phenotype variations on | Identification only of SNPs (and their relative genotypes) that have the greatest delta DSBP5_0 between therapy |

TABLE 3-continued

Inferential Statistical Analysis

| Procedure | Analysis | Selected Threshold |
|---|---|---|
| | joint effect of SNPs Assessment performed using a single linear regression model, as implemented in StataSE 9.2, Parameter: delta DSBP5_0 between therapy and placebo | and placebo choosing as cutoff a delta SBP5_0 > 15 mmHg |

Table 3 summarizes the statistical procedures, thresholds and analysis selected by Applicants in view of the results of the descriptive statistical procedure.

In particular, with reference to the univariate analysis a single point analysis where the SNPs are considered one by one was performed. The quantitative trait interaction test (G*E, Gene*Environment) performed evaluates the association as Phenotype=SNP+therapy+SNP*therapy where the emphasis of the analysis was on the SNP*therapy component, i.e. in the interaction rather than in the main effects, since the main effect "therapy" corresponds to testing the clinical trials per se, without considering the genetic component. The main effect "SNP" looks for SNPs affecting variation in blood pressure without considering the modification induced by the therapy. Only the interaction effect (G*T) evaluates which SNPs (G=gene) affect SBP in subjects receiving either the active drug or the placebo (T=Therapy).

Figure 4:
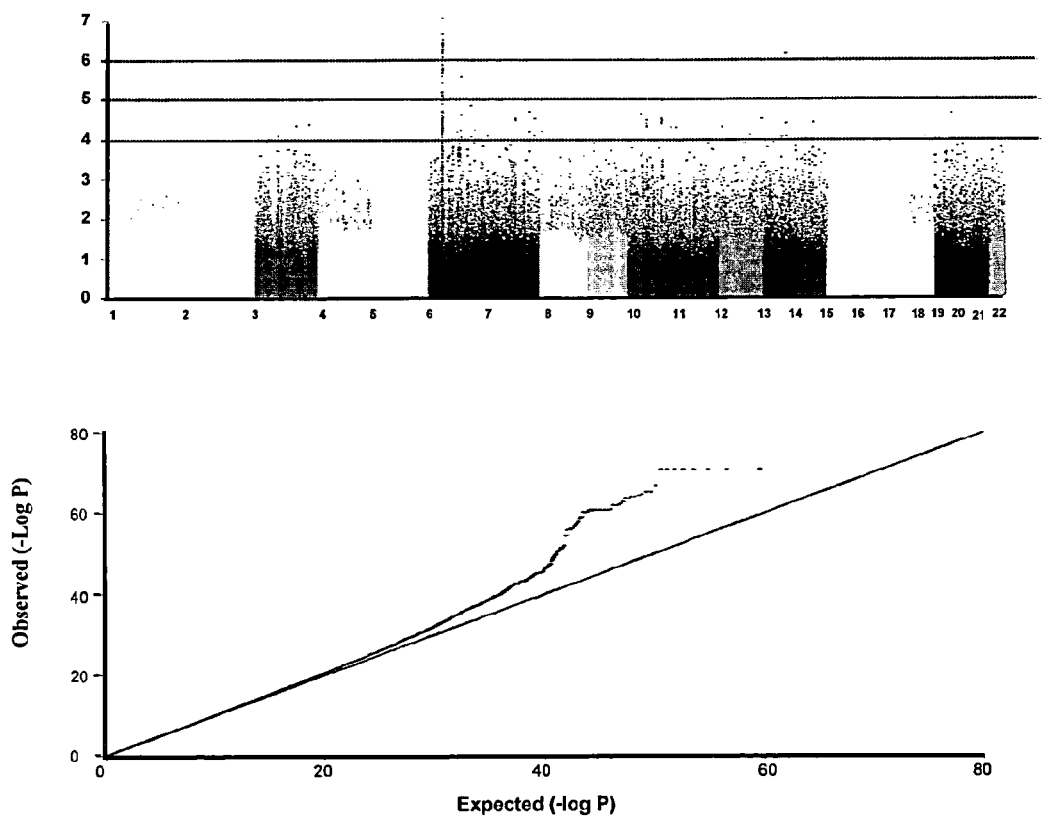
FIG. 4 shows a diagram illustrating the results of GXE association results for placebo and therapy of SNPs according to some embodiments herein disclosed. In Panel A, the Y axis of the plot represents the pvalue of significance (-log Pvalue) while the X axis the position in the genome. Each point represents a SNP and in particular the red dots represent SNPs with a significant pvalue ($p<10^4$). Panel B shows comparison of distributions of observed versus expected pvalues generated by GXT association Test (Q-Q plot). The inflation in the tail of the distribution represents true positive associations.

A threshold of $p<10^4$ was selected to screen the most significant associations that could form a list of top SNPs. In particular, Applicants purposefully selected a "conservative" p value (against False Negative) to screen out the less significant results [Ref. 34, 35]. Additionally, all potential positive associations have been meaningfully verified with at least two statistical programs (plink and stata). Results of univariate analysis performed according to the above approach are illustrated in FIG. 4 (see also Example 6 below).

With reference to the inferential interactions analysis, the interactions across various genes were tested to see if the observed variations of the QT phenotype DSBP5_0 depend on the joint effect of more SNPs considered together.

In particular, a single linear regression model, as implemented in StataSE 9.2, was then used to test for the interaction effect (SNP1*SNP2*ther) between a first set of SNPs (SNP1) and a second set of SNPs (SNP2) in addition to the marginal effects of SNP1 and SNP2, within rostafuroxin/placebo.

The SNPs sets were established taking into account the genes where the SNPs were detected, and the possible involvement of the genes in mechanisms identified as responsible of the phenotype of choice (variation of blood pressure).

Those SNPs were further selected to identify the genotypes with the largest response to rostafuroxin compared to placebo by performing a Statistical ANOVA analysis using STATA software in placebo and rostafuroxin with DSBP5_0 as dependent variable and the candidate significant SNPs as independent variables. In particular, to select the genotypes of the interactions between two SNPs with the largest response to rostafuroxin compared to placebo, the Applicants performed an ANOVA statistics in placebo and rostafuroxin with DSBP5_0 as dependent variable and the interactions between SNPs as independent variables. The Applicants report an example of this procedure in FIG. 5: interaction between rs8899 and rs4678. The Applicants selected the interaction between the genotype AA of rs8899 and the genotype BB of rs4678 because it presents the greatest remarkable decrement in the therapy group and not in the placebo group.

Figure 5:
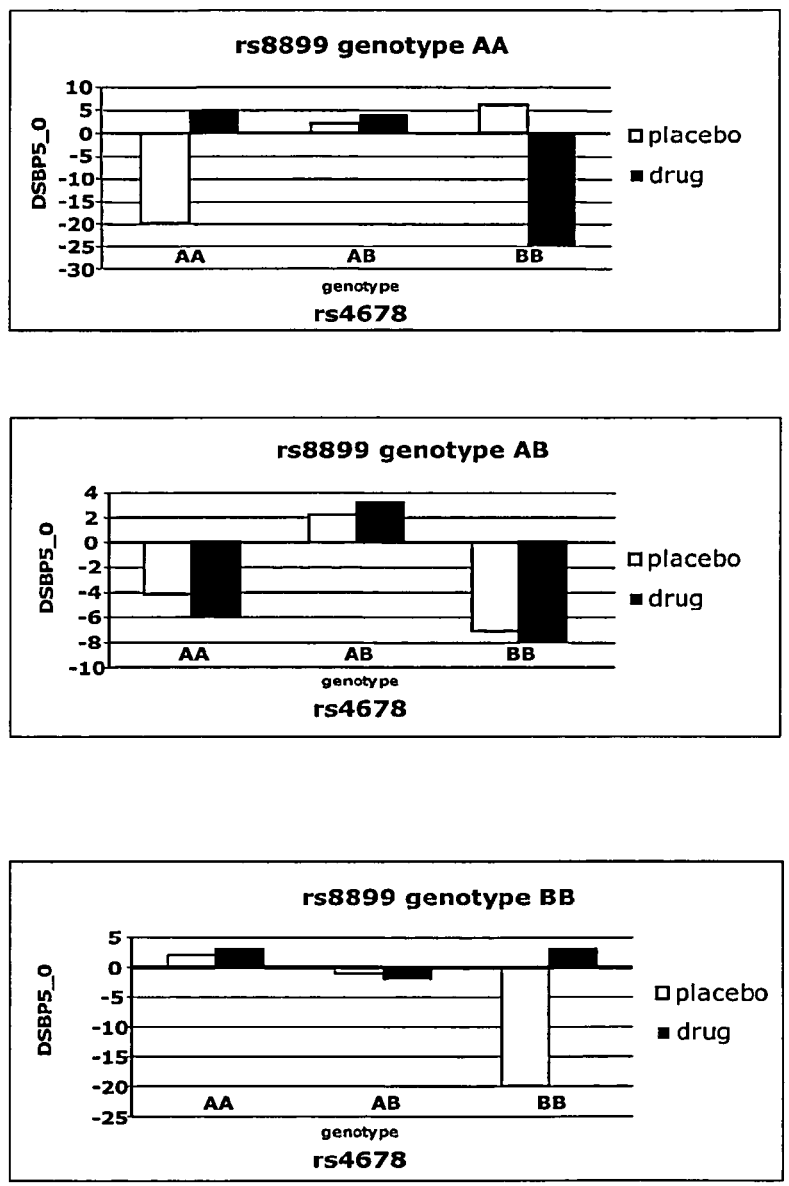
FIG. 5 shows diagrams illustrating steps for selection of genotypes of interactions of SNPs for rostafuroxin according to some embodiments of the present disclosure. In particular.
Figure 7:
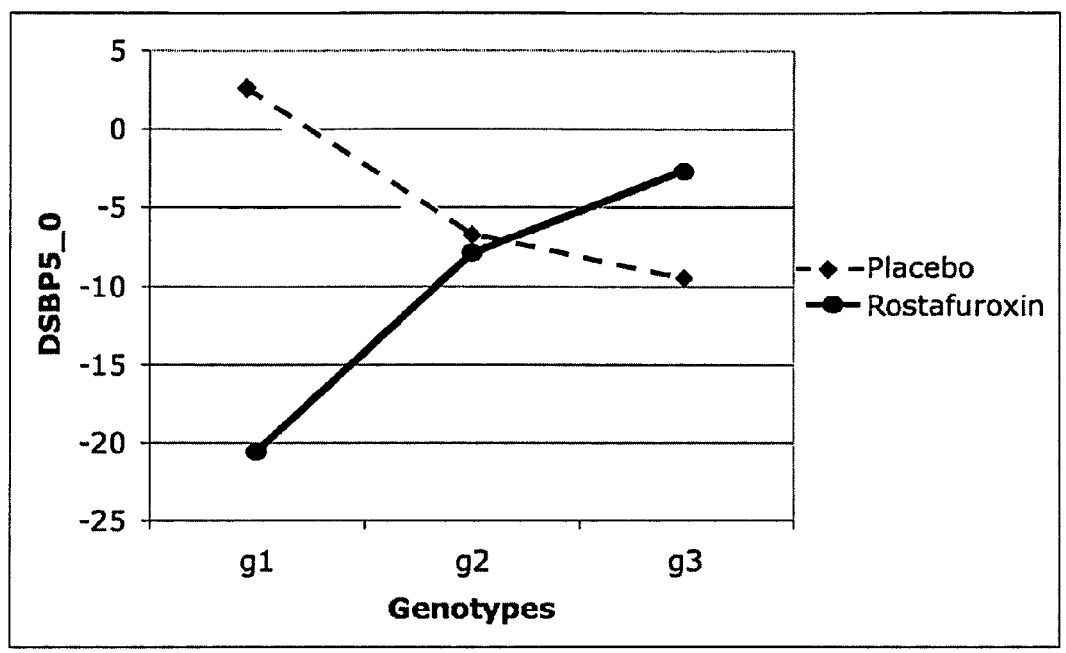
FIG. 7 shows a diagram illustrating an exemplary interaction between different genotypes of one hypothetical SNP and the blood pressure changes (DSBP5_0) with rostafuroxin and placebo.

In outcome of this investigation, the Applicants selected the genotypes of interactions of SNPs having a remarkable decrement of the QT phenotype DSBP5_0 in the rostafuroxin and not in the placebo group, such as the example of rs8899 and rs4678 in FIG. 5.

All the genetic analyses were performed using the program package gPLINK [Ref. 33]. Principal Component Analysis (PCA) using the Eigensoft package (version 2.0 for Linux platform, Department of Genetics, Harvard Medical School, Boston, USA). Genomic inflation factor λ was calculated using Genomic Control (GC) of eigensoft package. To complete the statistical genetic analyses and for all those analyses beyond the pure statistical genetics approach, the program StataSE 9.2 was used. A skilled person will be able to identify all the additional details statistical analyses upon reading of the present disclosure.

Following the descriptive and inferential statistical analysis denotypinq profiles were also created for the purpose of discriminating Responders (R) from Non-Responders (NR) to the active treatment using the smallest possible set of significant SNPs. In this case, a "genetic profile" is a linear combination of genotypes at single SNPs or at their interactions.

To create the profiles different genotypes for each SNPs were considered as variable and in particular the homozygous less frequent genotype was identified as genotype 1 (g1), the heterozygous genotype was identified as genotype 2 (g2) and the homozygous more frequent genotype was identified as (g3).

Accordingly, genetic profiles were built that could have for example a g1 of an SNP1 (component 1), a g2 of an SNP2 (component 2) and the interaction of the g1 of SNP3 with the g2 of SNP4 (component 3) as factors. A profile can have any number of components.

Any given profile was coded equal to 1 if at least one component, presents the significantly associated genotype (e.g., the g1 of SNP 1 in the example before), otherwise the profile is coded as 0. Then, all subjects are classified as 0 or 1, depending on their fit to the profile allowing a profile to characterize a defined subset of patients.

The predictive ability of different profiles to classify subjects into R or NR, i.e. finding the genotypic profiles that discriminate R from NR for rostafuroxin, was then tested using a logistic regression performed to procedures such as the ones described in [Ref. 36, 37].

The parameter selected by Applicants to evaluate the genetic profiles was the Odds Ratio (OR) which is one of the parameters considered informative of performance of pharmacogenomic tests according to FDA guidelines [Ref. 38]. In particular, according to FDA guidelines, OR is a clinically relevant parameter for evaluating the degree of discrimination according to the different genetic profiles between patient responders to the drug instead of placebo.

The OR value indicates the ratio of the odds in test positive patients (responders) to the odds in test negative patients (not responders) according to the defined genetic profile. The Odds ratio combines the Positive (PPV) and the Negative (NPV) Predictive Values as follows: PPV×NPV/[(100−PNV)×(100−NPV)]. The Predictive values (either positive or negative) represent the proportion of patients with a positive or negative test result that have the clinical condition of interest (i.e. response to the drug with a defined genetic profile). In other word, OR is the probability of being a responders (PPV)

or non responders (NPV) to the test. An Odds ratio of 1 indicates that the test is non-informative, thus the higher the Odds ratio the higher is the predictive power of the test.

Based on the results of the above study, Applicants identified several SNPs and related genotypic profiles that significantly affect the selected quantitative phenotype for detecting the effect of rostafuroxin.

In particular, some core SNPs located in genes previously not associated with pathways affecting blood pressure surprisingly showed a remarkable ability to enhance the effects of rostafuroxin as illustrated in the following examples.

Example 1

Core SNPs Affect Individual's Response to Rostafuroxin

In outcome of the above outlined study a group of SNPs was identified as significantly affecting the individuals' response to rostafuroxin that is herein also identified as core SNPs. The main features of the core SNPs herein described are illustrated in the Table 4.

The SNPs detected in outcome of genotyping were first subjected to univariate analysis and then to further analysis to select the SNPs genotypes with the largest response to rostafuroxin as illustrated above.

In particular, to select the genotypes with the largest response to rostafuroxin compared to placebo, the Applicants performed an ANOVA statistics (oneway) in placebo and rostafuroxin with DSBP5_0 as dependent variable and the significant SNPs as independent variables.

The analysis performed is exemplified in FIG. 6 where an analysis for SNP rs2461911 is shown that concerns a significant phenotype variance in the SNP genotypes g1, g2 and g3 greater in therapy group (p=0.002) than in placebo (p=0.045).

Variation of the DSBP5_0 values for the three genotypes of SNP rs2461911 g1, g2 and g3 is also illustrated in FIG. 7, which shows the plot of the DSBP5_0 values for the three genotypes of SNP rs2461911 comparing rostafuroxin and placebo groups. From the illustration of FIG. 7, it is clear that in genotype 1 there is a clear reduction of blood pressure with rostafuroxin while with placebo the blood pressure is modestly increased. Conversely in genotype 3 the blood pressure fall seems to be greater with placebo. What it is important is the direction of changes in blood pressure response with placebo and rostafuroxin according to these genotypes that clearly follow and opposite trend. This can be analyzed and we can establish the statistical significance of the model and of the interactions between rostafuroxin and placebo for that particular SNP. An appropriate statistical analysis provides the significance of the interaction (which is accepted only if the significance of the model is <0.05). The p values for interaction are given in table 4 as P-GXE.

TABLE 4

| Core SNPs | | | | | | |
|---|---|---|---|---|---|---|
| SNP ID | rs16877182 | rs5013093 | rs2461911 | rs12513375 | rs16893522 | rs2345088 |
| Chr | 7 | 6 | 10 | 4 | 6 | 2 |
| Major Allele | C | C | G | T | G | C |
| Minor Allele | T | T | A | G | A | T |
| P_GXE | 2.89E−05 | 3.41E−05 | 4.43E−05 | 6.91E−05 | 8.54E−05 | 9.63E−05 |
| position | 11753617 | 29928565 | 57078480 | 148244380 | 82560511 | 18079898 |
| GENE | THSD7A | Unknown | Unknown | Unknown | Unknown | unknown |
| Location | Intron | Intergenic | Intergenic | Intergenic | Intergenic | intergenic |
| nearest flanking gene(NFG) | N/A | HLA-G | LOC389970 | TTC29 | FAM46A | KCNS3 |
| distance between SNP and NFG | N/A | 21 kb-Flanking_3' | 18 kb Flanking_3' | 150 kb-flanking 5' | 41 kb-Flanking_5' | 102 kb Flanking_3' |
| protein name | Thrombospondin type-1 domain-containing protein 7A precursor. | HLA class I histocompatibility antigen. alpha chain G precursor | Pseudogene | TPR repeat protein 29 | family with sequence similarity 46, member A | Potassium voltage-gated channel subfamily S member 3 |

The core SNPs rs2345088, rs16877182, rs16893522, rs2461911, rs5013093, and rs12513375 are newly identified single nucleotide polymorphisms, with exact chromosomal location in human genome but, at present, with unknown function, that have been identified in a Genome-Wide Scanning and association analysis (GWAS) as the smallest set of significant SNPs associated to blood pressure response to rostafuroxin in outcome of the statistical analysis outlined above.

In particular these SNPs were identified following genotyping of the whole genome of the tested individuals performed according to Whole Genome Genotyping (WGG) based on the Sentrix BeadChip platform [Ref. 10]. More particularly, the WGG was performed using Human1M Duo CHIP—Infinium II Assay to interrogate over 1 million SNPs along the whole genome of the patients, through unrestricted locus selection according to procedure described identifiable by a skilled person and described, for example, in [Ref. 10, 11, 12] in further detail.

A similar approach was applied to analyze and select the other core SNPs so that in outcome of this investigation, the Applicants selected the genotypes of SNPs having a remarkable decrement of the QT phenotype DSBP5_0 in the rostafuroxin and not in the placebo group, such as the example rs2461911 in FIG. 7.

A summary of the data related to DSBP5_0 in individuals presenting the core SNPs and treated with rostafuroxin (Therapy) versus the individuals presenting the core SNPs and treated with placebo (Placebo) is illustrated in Table 5.

TABLE 5

Decrement in DSBP5_0 for Core SNPs

| SNP ID | p_value ANOVA | Illumina genotype | Relevant genotype | DSBP5_0 Therapy | DSBP5_0 Placebo | Delta DSBP5_0 |
|---|---|---|---|---|---|---|
| rs2345088 | 0.0002 | 1 | TT | −30.5 | 3.43 | 33.93, |
| rs16877182 | 0.0003 | 2 | C/T | −21.67 | −2.82 | 18.85, |
| rs16893522 | 0.0048 | 1 | AA | −22.43 | 4.60 | 27.03, |
| rs2461911 | 0.0022 | 1 | AA | −20.6 | 2.22 | 22.82, |
| rs5013093 | 0.0022 | 1 | TT | −20.49 | 1.60 | 22.09, |
| rs12513375 | 0.0024 | 3 | TT | −19.18 | −3.25 | 15.93, |

In particular, the data in Table 5 were obtained using a stepwise linear regression using DSBP5_0 as dependent variable and the SNPs as independent variables to select the SNPs significantly associated to the QT phenotype DSBP5_0.

Example 2

A Genetic Profile Comprising Core SNPs Affect Individual Response to Rostafuroxin Following the identification of the SNPs, Applicants investigated the predictive ability of genetic profiles comprising the core SNPs of Example 1 were considered. The rationale supporting construction of genetic profiles relies upon the well established notion that the phenotypic effect of a given SNP must also be evaluated within the context of the other SNPs harbored on genes coding for proteins that interact with the protein associated to the first SNPs (genetic network). In this sense, a network analysis also implies the concept of genetic epistasis [Ref 39]. In fact, alleles at two loci may not have any detectable effect when these alleles are analyzed separately but they may become phenotipically relevant when analyzed together, since they co-occur in the same subjects.

The Applicants evaluated if a genetic profile comprising core SNPs in the therapy group only, can discriminate the Responders from Not Responders to the treatment using as a predictive model a logistic regression in which the dependent variable is the dicotomic phenotype (R or NR) and the independent variable the specific profile. The applicants then evaluated the goodness of the model calculating the predictive parameters (Odds Ratio, PPV, NPV).

Exemplary data related to the genetic profile including all core SNPs of Example 1 are illustrated in FIG. 8. In particular, FIG. 8 illustrates data concerning Odd Ratio (OR) and predictive values (p-values) for profiles comprising the core SNPs, which are parameters considered informative of performance of pharmacogenomic test according to the FDA guidelines [Ref.38].

In particular, the OR value indicates the ratio of the odds in test positive patients (responders) to the odds in test negative patients (not responders) according to the defined genetic profile. In particular, the Odd ratio combines the Positive (PPV) and the Negative (NPV) Predictive Values as follows: PPV×NPV/[(100−PNV)×(100−NPV)]. In other word, OR is the probability of being a responders (PPV) or non responders (NPV) to the test. An Odds ratio of 1 indicates that the test is non-informative, thus the higher the Odds ratio the higher is the predictive power of the test. The p-values (either positive or negative) represent the proportion of patients with a positive or negative test result that have the clinical condition of interest (i.e. response to the drug with a defined genetic profile).

The p-value parameter is calculated based on the zscore and it indicates the significance of OR. The zscore parameter indicates: In (OR)/Standard Error (InOR). The zscore has a negative value if the OR is minor to 1 and then if the profile is not able to predict the response to drug. While the zscore has a positive value if the OR >1 and then the profile is able to predict the response to drug: if zscore is high the OR is more significant due to the smaller variance.

Among the above mentioned parameters, the Odds Ratio (OR) is considered clinically relevant for evaluating the degree of discrimination according to the different genetic profiles between patient responders to rostafuroxin instead of placebo [Ref.38].

The data related to a profile comprising all core SNPs (Profile 4) summarized in FIG. 8 were obtained considering data from patients including one or more SNPs of the core SNPs listed in the profile. The criteria is justified by the occurrence of the two factors that usually support inclusion of patients carrying at least one SNP in a single unique profile: i) the strong prediction power of the SNP and ii) by a common plausible biological mechanism that link the SNPs at issue. In particular, the prediction power of the SNPs may be evaluated from the OR and the correctly classified patients according to methods identifiable by a skilled person. The corresponding parameter is a "correctly" value that for patients with profile 4 is of 79.8% (see FIG. 8). This value indicates that in 80 patients out of 100 the profile provides a correct classification of patients into responders and non responders.

In view of the above results, it is possible to conclude that the core SNPs affect the pharmacological activity of rostafuroxin with clinical relevance. In particular, the clinical relevance is due to the magnitude of the blood pressure drop difference between drug (rostafuroxin) and placebo, which ranges from 23 to 15 mmHg with rostafuroxin while, according to literature, this difference ranges between 4 and 6 mmHg with the ARBs.

Preliminary data in patients carrying the profile 4 obtained in two separate studies demonstrate that the drop in blood pressure obtained with rostafuroxin is more than 40% larger than that detected among the available antihypertensive agents (see FIG. 8, bottom portion). In particular, individuals carrying profile 4 show a modification in blood pressure of: −12.3±1.5 mmHg with HCTZ; −11.3±1.7 with Losartan and −18.74±1.8 mmHg with rostafuroxin; individuals with profile 8 show the a decrease in blood pressure of −11.3±1.2 with HCTZ; −11.6±1.3 with Losartan and −15.2±1.5 mmHg with rostafuroxin; individuals with profile 9 show the a decrease in blood pressure of −11.9±1.2 with HCTZ; −11.4±1.4 with Losartan and −15.2±1.5 mmHg with rostafuroxin.

Example 3

A Genetic Profile Including CORE SNPs Together with Relevant SNPs Affects Response to Rostafuroxin Interactions of the core SNPs with additional SNPs identified in the course of the above mentioned pharmacogenomic study were analyzed to verify the possible identification of additional genetic profiles suitable to discriminate R from the NR to the treatment using as a predictive model a logistic regression.

In particular the core SNPs profile of Example 2 (Profile 4) was combined with additional relevant SNPs identified in the course of the study.

Relevant SNPs, in the context of the present description indicate SNPs suitable to discriminate Responders from Non-Responders to rostafuroxin.

In particular, relevant SNPs were first investigated in the following three groups of genes: a) genes that are directly involved in the action mechanisms of rostafuroxin (such as Adducin and EO genes—see Example 4) herein also indicated as CAND 1; b) genes that may be involved in the development of hypertension and/or in an organ damage associated to hypertension (such as WNK—see Example 5) herein also indicated as CAND 2; and c) genes identified by performing a whole genome scanning (such as HLA-A, see Example 6) herein also indicated as GWS.

In particular, SNPs in those genes were first identified by genotyping the selected genes. Relevant SNPs were then selected by subjecting the detected SNPs to descriptive and inferential analysis as further illustrated in Examples 4 to 6.

The relevant SNPs so identified were then grouped in genetic profiles together with the core SNPs of profile 4 of Example 2.

The results show that genetic profiles comprising core SNPs and relevant SNPs are even more effective in discriminating rostafuroxin Responders from Non-Responders as illustrated in FIG. 8.

In particular, in the summary of FIG. 8 the OR and p-value and DSBP5_0 detected for additional profiles formed by the core SNPs (profile 4) and additional CAND 1, CAND 2 and/or GWS SNPs are also illustrated (see in particular profile 8 and profile 9 of FIG. 8). From the analysis of the data of FIG. 8 it appears that by including additional SNPs in the profiles, the OR values and "correctly" value are increased with respect to the ones of the profile 4 (see profile 8 and profile 9 in FIG. 8). Also the inclusion of those SNPS determines an increase in the size of the target population from the 26% of total population of profile 4 to 44% of the total population of profile 9.

A possible explanation of the synergic effect between the core SNPs and the additional SNPs indicated in FIG. 8, herein provided for the purpose of guidance and not intended to be limiting, is the inclusion of the SNPs at issue in a same genetic network underlying complex diseases such as hypertension. The experimental evidence obtained by the Applicants supports the conclusion that these SNPs can either interfere with or modulate the other genes (such as CAND1 or CAND2 already associated with pathways affecting blood pressure—see Examples 4 and 5) in a genetic networking or affect other genes which may be unrelated to a priori selected list of candidates (see profile 4 in comparison with profiles 8 and 9).

Accordingly, a possible explanation of the data reported herein is that the discriminatory capacity of the core SNPs (profile 4) is increased by the CAND 1 and 2 because of inclusion in a same genetic network that combines/integrates the effects of GWS, Core SNPs, CAND 1, CAND 2 and additional unknown SNPs which are comprised in the network(s).

The increase of the discriminatory capacity and of the size of the selected patients included in the profile that has been achieved by moving from profile 4 to profile 9, supports the network concept.

Specific genotypes for the additional relevant genes included in profiles 8 and 9 of FIG. 8 are further described in Table 6 and Table 7 below.

TABLE 6

Profile 8 and Profile9 SNPs

| SNP name | SNP ID | chr | Major Allele | Minor Allele | position | GENE | Location | protein name |
|---|---|---|---|---|---|---|---|---|
| ADD1 | rs4961 | 4 | G | T | 2876505 | ADD1 | Exon (missense G460W) | adducin alpha subunit |
| ADD2 | rs4984 | 2 | C | T | 70753911 | ADD2 | Exon (silent) | adducin beta subunit |
| HSD18 | rs10923835 | 1 | A | T | 119811854 | HSD3B1 | Intergenic | 3-beta-hydroxysteroid dehydrogenase |
| HSD19 | rs947130 | 1 | G | A | 119818255 | HSD3B1 | Intergenic | 3-beta-hydroxysteroid dehydrogenase |
| LSS2 | rs914247 | 21 | G | A | 46434105 | LSS | 3' UTR | lanosterol synthase |
| MDR2 | rs1045642 | 7 | T | C | 86976591 | MDR1(ABCB1) | Exon (silent) | Multidrag resistance 1 (ATP-binding cassette, subfamily B, member1) |
| WNK1 | rs880054 | 12 | A | G | 858819 | WNK1 | Intron | WNK lysine deficient protein kinase1 |
| rs10502933 | rs10502933 | 18 | C | T | 47548901 | unknown | Intergenic | |
| rs2131127 | rs2131127 | 3 | C | T | 149906833 | AGTR1 | Intron | angiotensin II receptor type 1 |
| rs4309483 | rs4309483 | 18 | C | A | 54236897 | LOC100134069 | Unknown | Hypotetical protein LOC100134069 (3' flanking to NEDD4L) |
| rs4739037 | rs4739037 | 8 | G | A | 64065878 | NKAIN3 | 3' UTR | Na+/K+ transporting ATPase interacting 3 |

TABLE 7

Interactions between candidate and top SNPs in Profile 8 and Profile 9

| SNP1 | SNP1 ID | relevant SNP1 genotype | SNP1 allele | SNP 2 | SNP2 ID | relevant SNP2 genotype | SNP2 allele | DSB50 PLACEBO | DSBP50 ROSTAFUROXIN | Delta Rosta_placebo |
|---|---|---|---|---|---|---|---|---|---|---|
| MDR2 | rs1045642 | TT | T major | HSD18 | rs10923835 | AT + TT | T minor | .−0.10 | .−17.40 | 17.30 |
| LSS2 | rs914247 | GA + AA | A minor | MDR2 | rs1045642 | CC | C minor | .−3.95 | .−16.91 | 12.96 |
| LSS2 | rs914247 | AA | A minor | ADD1 | rs4961 | GT + TT | T minor | 5.17 | .−22.32 | 27.49 |
| HSD19 | rs947130 | GG | G major | NEDD4L | rs4309483 | AA | A minor | 10.3 | .−17.85 | 28.15 |
| MDR2 | rs1045642 | TT | T major | AGTR1 | rs2131127 | CC | C major | .−2.55 | .−16.9 | 14.34 |
| ADD2 | rs4984 | CC | C major | TOP | rs10502933 | CT | C major | 5.52 | .−19.21 | 24.73 |
| LSS2 | rs914247 | AA min | A minor | WNK1 | rs880054 | AG + GG min | G minor | 0.48 | .−16 | 16.48 |
| HSD19 | rs947130 | GG | G major | NKAIN3 | rs4739037 | GA | G major | .−2.46 | .−18.18 | 15.72 |

In view of the above results, it is possible to conclude that core SNPs comprised in a profile together with additional SNPs affect the pharmacological activity of rostafuroxin with clinical relevance which can be even higher than the activity of the core SNPs alone.

Example 4

Relevant SNPs Affecting Response to Rostafuroxin: CAND 1 Genes

Applicants investigated inclusion of additional relevant SNPs in genetic profiles also including the core SNPs of example 1 that identify responders to rostafuroxin.

In a first series of experiments, SNPs of genes involved directly in the mechanisms of action of rostafuroxin (herein also identified as CAND 1 genes) were investigated.

In particular, CAND 1 genes that were investigated included genes coding for adducin subunits (ADD1, ADD2, ADD3), and genes involved in the EO synthesis and metabolism (CYP11A1, HSD3B1, LSS, ABCB1/MDR1 and SLCO4C1). A summary of the features of the investigated genes is reported in Table 8.

TABLE 8

Selected Candidate Genes (CAND 1)

| N | Gene Symbol | Chr | Gene name |
|---|---|---|---|
| 2 | ADD1 | 4 | alpha adducing |
| 3 | ADD2 | 2 | beta adducing |
| 4 | ADD3 | 10 | gamma adducing |
| 5 | CYP11A1 | 15 | cytochrome P450, family 11, subfamily A, polypeptide 1 (cholesterol monooxygenase side-chain cleaving) |
| 6 | HSD3B1 | 1 | hydroxy-delta-5-steroid dehydrogenase, 3 beta- and steroid delta-isomerase 1 |
| 7 | LSS | 21 | lanosterol synthase (2.3-oxidosqualene-lanosterol cyclase) |
| 1 | ABCB1/MDR1 | 7 | ATP-binding cassette, sub-family B (MDR/TAP), member 1 |
| 8 | SLCO4C1 | 5 | solute carrier organic anion transporter family, member 4C1 |

In particular, Table 8 shows the selected CAND 1 genes and the related chromosome location, gene symbol and Gene name.

For each CAND1 gene of Table 8, SNPs were detected using SNPs: Single SNP analysis with Taqman Assay (assay on demand or custom MGB with probe and primer design from ABI).

The detected SNPs were subject to univariate analysis and relevant CAND1 SNPs were selected on the basis of the detected a variation of the QT phenotype DSBP5_0 selected for the study.

Exemplary relevant CAND 1 SNPs are reported in Table 9 and Table 10 together with the related GXT association results. A significant p_GXT indicates a significant DSBP5_0 different response to the treatment (rostafuroxin/placebo).

TABLE 9

CAND 1 SNPs

| SNP ID | GENE | CHR | Major Allele | Minor Allele | SNP position | Gene position | SNP location | p_value |
|---|---|---|---|---|---|---|---|---|
| rs4961 | ADD1 | 4 | G | T | 2876505 | | exon (missense G460W) | Ns |
| rs4984 | ADD2 | 2 | C | T | 70753911 | | exon (silent) | Ns |
| rs3731566 | ADD3 | 10 | A | G | 111876079 | | Intron | Ns |

TABLE 9-continued

CAND 1 SNPs

| SNP ID | GENE | CHR | Major Allele | Minor Allele | SNP position | Gene position | SNP location | p_value |
|---|---|---|---|---|---|---|---|---|
| rs914247 (LSS2) | LSS | 21 | G | A | 46434105 | | 3UTR | 0.0027 |
| rs1045642 (MDR2) | MDR1 | 7 | T | C | 86976591 | | exon (silent) | Ns |
| Various | HSD3B1 | 1 | | | | 119855276 | | Ns |
| various | CYP11A1 | 15 | | | | 72432145 | | Ns |
| various | SLCO4C1 | 5 | | | | 101628871 | | Ns |

TABLE 10

CAND 1 SNPs

| SNP ID | p_value ANOVA | Relevant genotype | DSBP5_0 Therapy | DSBP5_0 Placebo | Delta DSBP5_0 |
|---|---|---|---|---|---|
| rs914247 (LSS2) | 0.0002 | AA | −17 | −6, 16 | 10, 87, |

In particular, Table 9 shows the results of the univariate analysis of selected exemplary CAND 1 SNPs together with related gene symbol, chromosome location, position on chromosome, location on gene and p value.

The two relevant SNPs for HSD3B1 gene (HSD18 and HSD19) are described in detail in Table 6 and their relevance in Table 7.

In Table 10 the data for the relevant SNP rs 914247 are reported.

As explained in the detailed description genes and adducin the genes included in table 9 are those suggested to encode adducin and enzymes involved in EO synthesis and transport. Rostafuroxin at picomolar concentrations "in vitro" or at nanomoles doses in animals is able to selectively correct the effect of mutated adducin or ouabain on Na—K Pump and cSrc, without blocking the effect of wild adducin.

Example 5

Relevant SNPs Affecting Response to Rostafuroxin CAND 2 Genes

In a second series of experiments, SNPs of genes that may be involved in the development of hypertension and/or in an organ damage associated to hypertension (herein also identified as CAND 2 genes) were investigated.

In particular, a larger set of genes that are pathophysiologically relevant were selected as CAND 2 genes. The selection criteria mainly included genes coding for the RAA enzymes and receptors, various families of ionic channels and transporters regulating renal sodium reabsorption, adrenergic receptors, podocyte proteins and transcription factors. The resulting set of genes is summarized in the illustration of FIG. 9.

In particular, in FIG. 9 the Selected Candidate Genes "CAND2 together with the relevant chromosome location, gene symbol and Gene name are indicated.

Additional information concerning those genes is identifiable to a skilled person upon reading of the present disclosure.

For each CAND2 gene of the table of FIG. 9, SNPs were detected using Tag SNPs present all over the genome and in the Illumina chip that could provide the evaluation of the variation within candidate genes to evaluate the influence of these genes on the blood pressure response to rostafuroxin.

The detected SNPs were subject to univariate analysis and only SNPs with a p-value GXT ranging from 1.78*10E−4 (rs7117314) to 5*10E−2 (rs945403) were selected with the same methodology illustrated for the selection of Core SNPs. Dealing with candidate genes we only used as a threshold a p<0.05 instead of p<0.0001 in view of previous data supporting the choice of candidate genes.

In particular the relevant CAND2 SNPs were selected on the basis of the detected a variation of the QT phenotype DSBP5_0.

Exemplary CAND 2 SNPs are reported in Table 11, together with the related GXT association results. A significant p_GXE indicates a significant DSBP5_0 different response to the treatment (rostafuroxin/placebo).

TABLE 11

Univariate analysis of relevant CAND 2 SNPs

| N | Snp | gene_name | CHR | Position | P_GXE | Location |
|---|---|---|---|---|---|---|
| | rs242093 | ACTN1 | 14 | 68551096 | 0.007169 | flanking_5UTR |
| 2 | rs1996396 | ADRA1A | 8 | 26918290 | 0.002707 | flanking_5UTR |
| 3 | rs10503806 | ADRA1A | 8 | 26938920 | 0.00381 | flanking_5UTR |
| 4 | rs13251780 | ADRA1A | 8 | 26950888 | 0.004704 | flanking_5UTR |
| 5 | rs17430706 | ADRA1A | 8 | 26894087 | 0.007211 | flanking_5UTR |
| 6 | rs10102024 | ADRA1A | 8 | 26841288 | 0.009325 | flanking_5UTR |
| 7 | rs526302 | ADRA1A | 8 | 26746612 | 0.01782 | Intron |
| 8 | rs544104 | ADRA1A | 8 | 26767907 | 0.03642 | Intron |
| 9 | rs3102087 | ADRA1A | 8 | 26755854 | 0.04356 | Intron |
| 10 | rs5183 | AGTR1 | 3 | 149942574 | 0.02 | Coding |

TABLE 11-continued

Univariate analysis of relevant CAND 2 SNPs

| N | Snp | gene_name | CHR | Position | P_GXE | Location |
|---|---|---|---|---|---|---|
| 11 | rs3772627 | AGTR1 | 3 | 149912944 | 0.04049 | Intron |
| 12 | rs2276736 | AGTR1 | 3 | 149908563 | 0.04824 | Intron |
| 13 | rs2131127 | AGTR1 | 3 | 149906833 | 0.04983 | Intron |
| 14 | rs3741559 | AQP2 | 12 | 48631243 | 0.03534 | Intron |
| 15 | rs2217342 | ATP1A3 | 19 | 47181356 | 0.008238 | Coding |
| 16 | rs10927888 | CLCNKA | 1 | 16226098 | 0.04384 | Intron |
| 17 | rs6604909 | CLCNKB | 1 | 16244519 | 0.03099 | Intron |
| 18 | rs945403 | CLCNKB | 1 | 16246917 | 0.04996 | Intron |
| 19 | rs7117314 | FXYD2 | 11 | 117203972 | 0.0001782 | 5UTR |
| 20 | rs10790212 | FXYD2 | 11 | 117207900 | 0.001169 | flanking_5UTR |
| 21 | rs11216598 | FXYD6 | 11 | 117253662 | 0.00677 | flanking_5UTR |
| 22 | rs910682 | FYN | 6 | 112282428 | 0.0004279 | flanking_5UTR |
| 23 | rs13218316 | FYN | 6 | 112189727 | 0.00389 | Intron |
| 24 | rs4309483 | NEDD4L | 18 | 54236897 | 0.006163 | flanking_3UTR |
| 25 | rs13280307 | NKAIN3 | 8 | 63586548 | 0.001652 | Intron |
| 26 | rs4739037 | NKAIN3 | 8 | 64065878 | 0.002954 | UTR |
| 27 | rs17596774 | PKD1 | 16 | 2086474 | 0.04037 | Intron |
| 28 | rs2728108 | PKD2 | 4 | 89180760 | 0.006608 | Intron |
| 29 | rs17786456 | PKD2 | 4 | 89176586 | 0.03221 | Intron |
| 30 | rs7696304 | PKD2 | 4 | 89179022 | 0.03269 | Intron |
| 31 | rs2725222 | PKD2 | 4 | 89177516 | 0.03857 | Intron |
| 32 | rs17199565 | SCNN1B | 16 | 23181205 | 0.004757 | flanking_5UTR |
| 33 | rs2758152 | SGK1 | 6 | 134530606 | 0.008541 | flanking_3UTR |
| 34 | rs1057293 | SGK1 | 6 | 134535090 | 0.04496 | Coding |
| 35 | rs16960712 | SLC12A1 | 15 | 46329907 | 0.01024 | Intron |
| 36 | rs759359 | SLC8A1 | 2 | 40182609 | 0.007413 | flanking_3UTR |
| 37 | rs404214 | SLC8A1 | 2 | 40307852 | 0.02053 | Intron |
| 38 | rs1005213 | SLC8A1 | 2 | 40245293 | 0.0303 | Intron |
| 39 | rs17025453 | SLC8A1 | 2 | 40259918 | 0.03507 | Intron |
| 40 | rs2110923 | SLC8A1 | 2 | 40211501 | 0.04026 | Intron |
| 41 | rs1428571 | SLC8A1 | 2 | 40243974 | 0.04325 | Intron |
| 42 | rs435404 | SLC8A1 | 2 | 40293896 | 0.04652 | Intron |
| 43 | rs12908787 | TJP1 | 15 | 27878217 | 0.003622 | Intron |
| 44 | rs11647727 | UMOD | 16 | 20263666 | 0.0089 | Intron |
| 45 | rs880054 | WNK1 | 12 | 2594827 | 0.03876 | Intron |
| 46 | rs11064584 | WNK1 | 12 | 866932 | 0.04682 | Intron |

In particular, in Table 11 the GXT association results for placebo and therapy is illustrated. A significant p_GXT indicates a significant DSBP5_0 different response to the treatment (rostafuroxin/placebo).

Example 6

Relevant SNPs Affecting Response to Rostafuroxin: GWS Genes

In a third series of experiments, SNPs of genes detected with Whole Genome scanning (herein also identified as GWS genes) were also investigated.

Genomic SNPs were genotyped with the Human1M array from Illumina using Human1M Duo CHIP genotyping Bead Chip according to procedure described in [Ref. 10, 11, 12]. In particular, In total, 1111190 (92.66% of the total) SNPs were analyzed because the SNPs of chromosomes X and Y as well as the SNPs (XY) of pseudo-autosomal region of X were not considered.

The detected SNPs were subjected to univariate analysis in an approach to identify relevant SNPs according to methodologies described in the examples section.

The results of the univariate analysis (Quantitative trait Interaction—GxE) for GWS genes are illustrated in FIG. 4, which shows results for 848340 SNPs genotyped in a sample from 193 NPT Patients with the 107 SNPs having a p value lower than the established threshold of $p<10^{-4}$ are shown as dots.

A detailed annotation was then performed of the identified 107 SNPs aimed to clarify the role of the specific genomic region interested in association. The 107 top SNPs identified from this GWAS are actually denoted by these genomic positions: 7 in coding regions, 4 in 3'UTR, 30 in introns and 66 in intergenic regions. Among the last-mentioned group, some SNPs are proximal to gene region and could be localized into the relative promoter, while some others are so far from an annotated gene to be considered in desert regions.

Therefore, a more detailed annotation has been performed for top SNPs included in Profile 4 (single topSNPs) and for Profile 5 (interacting topSNPs) only, and we observed that the majority of them are intergenic variants with a minimum set of intronic SNPs. All these variants may belong to so-called "junk DNA" regions [Ref. 40], as already mentioned in Introduction—paragraph 1.3, thus representing a rich substrate for evolutionary innovations of sequences in eukaryotes.

The procedure followed for exhaustive annotation took in account for: i. SNPs showing MAF >5%; ii. a more recent mapping with help of different databases (NCBI Entrez Gene, HapMap, Ensembl); iii. selection from a group of SNPs in perfect or strong LD among them, with possible location in genic or functional regions; iv. PubMed analysis; v. annotation of published miRNA sequences and relative genomic targets.

For intragenic SNPs, Applicants noted no coding or splicing variants but we identified common intronic polymorphisms located in genes whose function is often unknown. Two topSNPs (rs3893464 and rs 5013093) were placed within the major histocompatibility complex class I region on chromosome 6, a peculiar region of extensive and high LD which contains several genes. In this case, an accurate gene annotation is more complex, and the expression and functional pattern investigation of included genes could help to define the right region. As SNPs can have different effects also on the miRNA target composition, especially for 3'UTRs, all topSNPs were virtually tested in different databases (www.patrocles.org, microrna.sanger.ac.uk, www.microrna.org), but any interesting results returned. Applicants also considered a searching against the intact precursor sequences or just the mature miRNAs. However, marker identification of drug response for the purposes of prediction, without further genetic localization of the source of the signal would be a sufficient endpoint for a GWA study.

Following the above characterization, the initial 107 GWS SNPs were further selected to identify the genotypes with the largest response to rostafuroxin compared to placebo by performing a Statistical ANOVA analysis using STATA software in placebo and rostafuroxin with DSBP5_0 as dependent variable and the 107 significant SNPs as independent variables. Additionally with this analysis the relevance of the genotype of above mentioned SNPs was also analyzed.

With this approach eventually only 35 SNPs (and their relative genotypes) were selected that have a DSBP5_0 decrement in the therapy and not in the placebo group to be considered as relevant GWS. A list of the relevant GWS gene is summarized in Table 12.

TABLE 12

Univariate analysis of relevant GWS SNPs

| SNPs | | | | THERAPY | | | PLACEBO | | | DELTA |
| --- | --- | --- | --- | --- | --- | --- | --- | --- | --- | --- |
| rs SNP | Gene | p_value ANOVA | geno-type | DSBP5_0 therapy | SD | number of patients | DSBP5_0 placebo | SD | No. of patients | delta_ Therapy_ placebo |
| rs12996186 | ARL5A | 0.0001 | 2 | −22.785714 | 16.342626 | 7 | −4.8222221 | 11.005428 | 9 | 17.9634919 |
| rs9893372 | ATP2A3 | 0.0002 | 3 | −10.910638 | 12.081035 | 47 | −6.4765957 | 10.579003 | 47 | 4.4340423 |
| rs7216331 | COX10 | 0.0023 | 2 | −15.808333 | 1.150387 | 12 | −1.8944444 | 9.5719856 | 18 | 13.9138886 |
| rs7521668 | DPH5 | 0.0004 | 1 | −25 | 0 | 1 | 3.95 | 6.5760933 | 2 | 28.95 |
|  |  |  | 2 | −13.044 | 12.951707 | 25 | −6.0227273 | 9.8237774 | 22 | 7.0212727 |
| rs188334 | FAIM3 | 0.0036 | 1 | −11.819048 | 10.627776 | 21 | −3.6727274 | 13.932941 | 22 | 8.1463206 |
| rs4998662 | FAM46A | 0.0001 | 2 | −15.805556 | 1.151048 | 18 | −2.2666667 | 7.1477936 | 15 | 13.5388893 |
| rs16893522 | FAM46A | 0.0048 | 1 | −22.433333 | 14.654805 | 3 | 4.6000002 | 5.6568545 | 2 | 27.0333332 |
|  |  |  | 2 | −1.138125 | 11.911463 | 16 | −4.0117647 | 12.26524 | 17 | 2.8736397 |
| rs6457110 | HCG9 | 0.0023 | 1 | −10.351613 | 12.372035 | 31 | −4.4896552 | 11.787019 | 29 | 5.8619578 |
| rs3893464 | HCG9 | 0.0086 | 1 | −10.989474 | 13.815245 | 19 | −1.9736842 | 8.6017337 | 19 | 9.0157898 |
| rs2517718 | HLA-A | 0.0006 | 1 | −11.825806 | 11.503274 | 31 | −5.6137931 | 10.594464 | 29 | 6.2120129 |
| rs1362126 | HLA-F | 0.0037 | 3 | −10.294118 | 10.867241 | 34 | −5.3636363 | 11.464342 | 33 | 4.9304817 |
| rs5013093 | HLA-G | 0.0022 | 1 | −20.485714 | 10.724182 | 7 | 1.5999999 | 2.8284271 | 2 | 22.0857139 |
| rs2345088 | KCNS3 | 0.0002 | 1 | −30.5 | 96.166511 | 2 | 3.4333334 | 11.033736 | 3 | 33.9333334 |
|  |  |  | 2 | −10.693103 | 11.909148 | 29 | −7.1814815 | 8.3223072 | 27 | 3.5116215 |
| rs6718282 | KCNS3 | 0.0028 | 1 | −41.299999 |  | 1 | / | / | 0 |  |
|  |  |  | 2 | −12.625 | 82.536465 | 8 | 1.2 | 12.445381 | 9 | 13.825 |
| rs721207 | LOC131691 | 0.0032 | 3 | −11.584375 | 13.303943 | 32 | −4.65 | 11.612437 | 24 | 6.934375 |
| rs2555500 | LOC389174 | 0.003 | 1 | −10.517391 | 1.221436 | 23 | −5.3172413 | 10.152799 | 29 | 5.2001497 |
| rs2461911 | LOC389970 | 0.0022 | 1 | −20.6 | 1.267024 | 5 | 2.2166667 | 10.168268 | 6 | 22.8166667 |
| rs8179654 | LOC642727 | 0.0032 | 3 | −10.953846 | 14.821472 | 13 | −2.5117647 | 10.327686 | 17 | 8.4420813 |
| rs1901139 | LOC644192 | 0.0036 | 3 | −12.107143 | 15.748087 | 14 | −1.59 | 8.9522746 | 10 | 10.517143 |
| rs2427832 | LOC649458 | 0.0014 | 2 | −10.384091 | 13.154536 | 44 | −3.5387096 | 9.5961685 | 31 | 6.8453814 |
| rs9361863 | LOC728360 | 0.0013 | 1 | −15 | 98.994949 | 2 | 4.6000002 | 5.6568545 | 2 | 19.6000002 |
|  |  |  | 2 | −13.477273 | 12.989.443 | 22 | −4.6444444 | 12.13712 | 18 | 8.8328286 |
| rs1998394 | LOC728316 | 0.0074 | 3 | −10.51282 | 1.334078 | 39 | −4.725 | 11.632855 | 44 | 5.78782 |
| ga001619 | PIGR | 0.0004 | 1 | −13.615 | 97.036224 | 20 | −4.363158 | 14.582418 | 19 | 9.251842 |
| rs2275531 | PIGR | 0.0024 | 3 | −12.18 | 1.063176 | 20 | −4.363158 | 14.582418 | 19 | 7.816842 |
| rs748140 | PIGR | 0.0034 | 1 | −11.279167 | 1.179624 | 24 | −4.7727273 | 13.75234 | 22 | 6.5064397 |
| rs4710592 | RCADH5 | 0.0033 | 3 | −23.825 | 12.273107 | 4 | −3.75 | 12.094548 | 14 | 20.075 |
| rs2743951 | RP3-377H14.5 | 0.0015 | 3 | −11.169697 | 10.505638 | 33 | −5.5499999 | 11.596885 | 32 | 5.6196971 |
| rs10159569 | SH3PXD2A | 0.0013 | 1 | −13.169231 | 13.134071 | 26 | −2.5413793 | 8.8390981 | 29 | 10.6278517 |
| rs3087816 | SLC30A7 | 0.0004 | 2 | −13.044 | 12.951707 | 25 | −6.0227273 | 9.8237774 | 22 | 7.0212727 |
| rs10493940 | SLC30A7 | 0.0003 | 2 | −12.132258 | 1.197376 | 31 | −6.1826087 | 9.6284924 | 23 | 5.9496493 |
|  |  |  | 3 | −25 | 0 | 1 | 3.9500002 | 6.5760933 | 2 | 28.9500002 |
| rs16877182 | THSD7A | 0.0003 | 2 | −21.671428 | 93.414332 | 7 | −2.81875 | 13.817295 | 16 | 18.852678 |
| rs2326912 | TMEM200A | 0.0008 | 1 | −11.7 | 0 | 1 | / | / | 0 |  |
| rs1110446 | TRIM31 | 0.003 | 1 | −16.366667 | 77.860986 | 3 | 4.2249999 | 3.4451657 | 4 | 20.5916669 |
|  |  |  | 2 | −10.134211 | 14.101299 | 38 | −6.6103448 | 12.376024 | 29 | 3.54 |
| rs12513375 | TTC29 | 0.0024 | 3 | −19.177778 | 13.342392 | 9 | −3.25 | 4.8086232 | 8 | 15.927778 |
| rs17414954 | VCAM1 | 0.0003 | 2 | −13.030769 | 1.203637 | 26 | −5.8727273 | 9.7369782 | 2 | 7.1580417 |

Example 7

Genetic Variations in Linkage Disequilibrium with Core SNPs

Even if the DNA variations included in profile 4, 8 and 9 have a strong genetic power in predict the Responder patients, they do not exhaust all the genetic variability having the best discriminatory capacity. According to Linkage Disequilibrium concept, a DNA variation (tag SNP) can be generally represented by a variable number of proxy SNPs able to type the variation equally or similarly compare to the tag SNP. Therefore, several additional genetic variations are included in the scope of the methods and systems herein described. Exemplary genetic variations in linkage disequilibrium with SNPs affecting the biological activity of rostafuroxin are listed in Table 13.

TABLE 13

Proxy SNPs relative to Core SNPs, Profile 8 and Profile9 SNPs, according to CEU HapMap data Rel 24

| SNP name | SNP ID | chr | proxy SNPs (r2 0.9-1) | Tag window |
|---|---|---|---|---|
| rs16877182 | rs16877182 | 7 | rs7341453, rs10499404, rs10499406, rs6957230, rs17165141, rs16877173, rs16877184, rs10499401, rs17165148, rs17165136 | 1 Mb |
| rs5013093 | rs5013093 | 6 | rs2517861, rs2734981, rs2734984, rs9258606, rs2508051, rs2517870, rs9258610, rs1632882, rs3128910, rs2734985, rs5013088, rs35332866, rs2734980, rs5013087,, rs2517860, rs2517850, rs1317834, rs2523760, rs5013091, rs1613062, rs7451408, rs9258690, rs2247719 | 750 kb |
| rs2461911 | rs2461911 | 10 | rs2461899 | 750 kb |
| rs12513375 | rs12513375 | 4 | rs6844319, rs11735165, rs11722430, rs4543091 | 750 kb |
| rs16893522 | rs16893522 | 6 | rs9449367, rs17730252, rs17662598, rs10081038, rs9449368 | 750 kb |
| rs2345088 | rs2345088 | 2 | no proxies in CEU HapMap | 750 kb |
| ADD1 | rs4961 | 4 | rs1263345, rs2239728, rs1263347, rs4690001, rs4690000, rs4964, rs16843523, rs2285084, rs2237004 | 750 kb |
| ADD2 | rs4984 | 2 | rs740389, rs740388, rs7559120, rs740391, rs740387, rs1048747, rs11894520, rs6750771, rs740390, rs7559225 | 750 kb |
| HSD18 | rs10923835 | 1 | no proxies in CEU HapMap | 750 kb |
| HSD19 | rs947130 | 1 | no proxies in CEU HapMap | 750 kb |
| LSS2 | rs914247 | 21 | rs7282841, rs2839141, rs6518278, rs4819216, rs2839157, rs2280955, rs2839146, rs2254524, rs9717, rs999691, rs2839175, rs4818828, rs4819214, rs2330408 | 750 kb |
| MDR2 | rs1045642* | 7 | rs4437575, rs2235048 | 750 kb |
| WNK1 | rs880054* | 12 | no proxies in our population, no info in CEU HapMap | 750 kb |
| rs10502933 | rs10502933 | 18 | rs12605208, rs3851123, rs10502932, rs17752711, rs12604658, rs1552090, rs2045748, rs8097074, rs17752681, rs1531686, rs12605843, rs12606532, rs17752449, rs17752602, rs17752743 | 1 Mb |
| rs2131127 | rs2131127 | 3 | rs10935724, rs12695877 | 750 kb |
| rs4309483 | rs4309483 | 18 | rs9319930, rs11152071, rs3744868, rs4384676, rs4383234, rs7226817, rs8099014, rs7230036, rs4940711, rs4464160, rs4940393, rs6566970, rs9319929, rs11152077, rs4940697, rs17064977, rs4245268, rs4640266, rs7234602, rs4331413, rs4559989, rs4940701, rs4245271, rs6566972, rs11152073, rs4940698, rs1806761, rs8092072 | 750 kb |
| rs4739037 | rs4739037 | 8 | rs12542042, rs4739011, rs12541993, rs10957266, rs10464903, rs12549172, rs12681795, rs12543961, rs10464905, rs930840, rs12546361, rs4739047, rs4737629, rs3758147, rs12542282, rs12541047, rs10957270, rs10957269, rs4739046, rs12545230, rs9969662, rs10957272, rs4737627, rs10464904, rs10957261, rs12548172, rs12547772, rs10957268, rs12678214, rs1480115, rs16929963, rs12676348, rs10957248, rs10957265, rs16929988, rs10957260, rs4739028, rs7818582, rs4737616 | 750 kb |

*LD pattern is calculated in European population

The genetic variations listed in Table 13 are the correspondent proxy SNP for each core or candidate SNP mentioned above derived from an exemplary genetic map concerning genetic data of the European population. The information derived by HapMap Project give us the best coverage of proxy SNPs in European population. Additional sources of information for genetic variation in linkage disequilibrium for European population and/or other populations can be retrieved through sources identifiable by a skilled person, which include for example Illumina BeadChip 1 Million genotype data on our population. When referring to sources such as HapMap a continuous updating with respect of the source release is needed to ensure complete listing of all the relevant genetic variation in the sense of the present disclosure.

Example 8

Sequence Information Concerning Core SNPs and Additional SNPs Affecting Response to Rostafuroxin In some embodiments of the present disclosure therapy can be evaluated based on detection of sequence information for several genetic variations affecting the individual response to rostafuroxin. Sequence information concerning the core SNPs and related selected genotypes are reported in Tables 14 and 15.

TABLE 14 sequence information core SNPs

| rsID | Sequence | Nucleotide variation | SEQ ID NO | Selected nucleotide variation | SEQ ID NO |
|---|---|---|---|---|---|
| rs16877182 | TTTGAGAATACCAAAATACAGAAAAA TTCAATCAAATTTTAAAGTTGGTANTA ATTATACTTGTTATTGGAATGTAATTT AGTTTTCTTAATTTAGTTTCT | N = A, C, G, T | 1 | N = C or T | 2 |
| rs5013093 | GGAAAAACCCAGTGCCCTCCCCTCC TCTCAAGCCTGGCCAGCTCTGACAG N GGGAGGACTCCCCAAAGAGA GGCTCTGGCCCTGGCTCCATGTCCT TCCAG | N = A, C, G, T | 3 | N = C or T | 4 |
| rs2461911 | GTCCAAATGTAATGTTCTAACTTAGTA CATTTGGAAAATTCTTTCCTAACNCCT CTGGGAAAACACAAAATATTACTTAC AAAAATAAATGCATAAAAATG | N = A, C, G, T | 5 | N = G or A | 6 |
| rs12513375 | GCTCGCCTTGGTCCACTGTGACACA CAGGCTGCTTTGCTGGGAAAGTTCTN CCTGACTCACTGGGGCTGCATGAAG CCTGGGGAGGCAAGCTTCTGGCGTG | N = A, C, G, T | 7 | N = G or T | 8 |
| rs16893522 | TGACACATGTGGCAGTCTGAAAAGTT CTTATTGAGCCAGACTGTAGAGTTCT TGGAAATCNCATACCATCTTCATGGG AATTATGATTCTACTCAGGCTGGGAG GAGTACATTAACTGAAG | N = A, C, G, T | 9 | N = A or G | 10 |
| rs2345088 | CAACATTTGGATTATGGCATTTGGGA TTCTGATTTTCAGAATTATGATTGGCA ATTTTAANTAATTCTGGCTCGGTATAT TAATAATGCAATGCTTTTTTCAAGCTA TTTGTAAGTGATTC | N = A, C, G, T | 11 | N = C or T | 12 |

TABLE 15 sequence information selected genotypes core SNPs

| rsID | Sequence | Selected nucleotide variation major allele | SEQ ID NO | Selected nucleotide variation minor allele | SEQ ID NO |
|---|---|---|---|---|---|
| rs16877182 | TTTGAGAATACCAAAATACAGAAAAA TTCAATCAAATTTTAAAGTTGGTANTA ATTATACTTGTTATTGGAATGTAATTT AGTTTTCTTAATTTAGTTTCT | N = C | 13 | N = T | 14 |
| rs5013093 | GGAAAAACCCAGTGCCCTCCCCTCC TCTCAAGCCTGGCCAGCTCTGACAG NGGGAGGACTCCCCAAAGAGAGGCT CTGGCCCTGGCTCCATGTCCTTCCA G | N = T | 15 | N = T | 16 |

TABLE 15-continued sequence information selected genotypes core SNPs

| rsID | Sequence | Selected nucleotide variation major allele | SEQ ID NO | Selected nucleotide variation minor allele | SEQ ID NO |
|---|---|---|---|---|---|
| rs2461911 | GTCCAAATGTAATGTTCTAACTTAGTA CATTTGGAAAATTCTTTCCTAACNCCT CTGGGAAAACACAAAATATTACTTAC AAAAATAAATGCATAAAAATG | N = A | 17 | N = A | 18 |
| rs12513375 | GCTCGCCTTGGTCCACTGTGACACA CAGGCTGCTTTGCTGGGAAAGTTCTN CCTGACTCACTGGGGCTGCATGAAG CCTGGGGAGGCAAGCTTCTGGCGTG | N = T | 19 | N = T | 20 |
| rs16893522 | TGACACATGTGGCAGTCTGAAAAGTT CTTATTGAGCCAGACTGTAGAGTTCT TGGAAATCNCATACCATCTTCATGGG AATTATGATTCTACTCAGGCTGGGAG GAGTACATTAACTGAAG | N = A | 21 | N = A | 22 |
| rs2345088 | CAACATTTGGATTATGGCATTTGGGA TTCTGATTTTCAGAATTATGATTGGCA ATTTTAANTAATTCTGGCTCGGTATAT TAATAATGCAATGCTTTTTTCAAGCTA TTTGTAAGTGATTC | N = T | 23 | N = T | 24 |

Sequence information for exemplary additional SNPs affecting the response to rostafuroxin, and related selected genotypes is reported in Table 16 and 17.

TABLE 16 sequence information of additional SNPs affecting response

| rsID | Sequence | Nucleotide variation | SEQ ID NO | Selective nucleotide variation | SEQ ID NO |
|---|---|---|---|---|---|
| Rs 4961 | AGAAGACAAGATGGCTGAACTCT GGCCGGGGCGACGAAGCTTCCG AGGAANGGCAGAATGGAAGCAGT CCCAAGTCGAAGACTAAGGTGTG GACGAACATT | N = A, C, G, T | 25 | N = G or T | 26 |
| Rs 4984 | CTTCATCAAAACACACCTAC CAATATGTTACTCCAGATGT GGAGGGCAACNCTGAAGAACTC GCACACGGCCGGACCAGAGCCT GGCTCTCGTTCCTGTCC | N = A, C, G, T | 27 | N = G or A | 28 |
| Rs 10923835 | CTACAAGTCTTTTATGCTCTGAAG CTTTTTGTCTTGGCAATTGCTTTA CANCATTCACAAAGGACAGCATT TACCTGGAGACCTCACCAGTGGG TCCCTGC | N = A, C, G, T | 29 | N = A or T | 30 |
| Rs 947130 | TCTGAACAATTTGGGATCTCTTTT AACTTGAGGGTCTCTTTCGACTA CTANAGCTCCATTTCCCCTCTTAA ATGAGAAGGG ATTTCTTTTCTTTTAAATCT | N = A, C, G, T | 31 | N = C or T | 32 |
| Rs 914247 | GCCAGGGACTGCTACCTGCCCA GAAGGCGGCAGGGAGGGGAAGA GCAGATNAGGAGGTATAGGGTGT GCCCTGGGCAAGGCAGCAGGGG TAACGAAGCTCT | N = A, C, G, T | 33 | N = A or G | 34 |
| Rs 1045642 | GAGAACATTGCCTATGGAGACAA CAGCCGGGTGGTGTCACAGGAA GAGATNGTGAGGGCAGCAAAGG AGGCCAACATACATGCCTTCATC GAGTCACTGCC | N = A, C, G, T | 35 | N = C or T | 36 |

TABLE 16-continued sequence information of additional SNPs affecting response

| rsID | Sequence | Nucleotide variation | SEQ ID NO | Selective nucleotide variation | SEQ ID NO |
| --- | --- | --- | --- | --- | --- |
| Rs 880054 | ACAGTAATAGTCTATTTAGCCTCT TTCTCTCCTGCTCTCCTTTCCATA TTNTTATGTGGCATATTAACTTAA CACTAATGT ATGCAGGGTTTTGTTGGTTT | N = A, C, G, T | 37 | N = C or T | 38 |
| Rs 10502933 | AATGTGATTTTTGATATAATTCTC ATGTTTTAGCTTTTCTAGTTTAAAA ANCTGCATACTGGAAAATAAGGA AAAAATTCTAGAGGTTGTATGAGA AGGA | N = A, C, G, T | 39 | N = C or T | 40 |
| Rs 2131127 | AACCAACTTTAGCATACCAAGTTT AGCATTTAGGCATACCAACTTTAG CANTGTTATACAGAATAATGTTAG CATTGGAAGGATCTATTAACAAAA GAAAG | N = A, C, G, T | 41 | N = C or T | 42 |
| Rs 4309483 | CCTCATGCAAAGCACTTGCTCAC ACACTGTCTCATTTCAACATCACC GCCNCTTAAGGAGATGCTATGAT CAACCCCACTTTGCAGATGAGGA AACTTCAG | N = A, C, G, T | 43 | N = C or A | 44 |
| Rs 4739037 | CTGGAGCTCGCCTTACACCAAAC AGACACAATCGATCCATTCGAAG TGTCNTAATTACACATTGAGGGA CCAACTAGACCTTTTCTCATTGTA AACTTGGA | N = A, C, G, T | 45 | N = G or A | 46 |

TABLE 17 sequence information of selected genotypes of additional SNPs affecting response

| rsID | Sequence | Selected nucleotide variation major allele | SEQ ID NO | Selected nucleotide variation minor allele | SEQ ID NO |
| --- | --- | --- | --- | --- | --- |
| Rs 4961 | AGAAGACAAGATGGCTGAACTCT GGCCGGGGCGACGAAGCTTCCG AGGAANGGCAGAATGGAAGCAGT CCCAAGTCGAAGACTAAGGTGTG GACGAACATT | N = G or T | 47 | N = T | 48 |
| Rs 4984 | CTTCATCAAAACACACCTAC CAATATGTTACTCCAGATGT GGAGGGCAACNCTGAAGAACTC GCACACGGCCGGACCAGAGCCT GGCTCTCGTTCCTGTCC | N = C | 49 | N = C | 50 |
| Rs 10923835 | CTACAAGTCTTTTATGCTCTGAAG CTTTTTGTCTTGGCAATTGCTTTA CANCATTCACAAAGGACAGCATT TACCTGGAGACCTCACCAGTGGG TCCCTGC | N = A or T | 51 | N = T | 52 |
| Rs 947130 | TCTGAACAATTTGGGATCTCTTTT AACTTGAGGGTCTCTTTCGACTA CTANAGCTCCATTTCCCCTCTTAA ATGAGAAGGG ATTTCTTTTCTTTTAAATCT | N = G | 53 | N = G | 54 |
| Rs 914247 | GCCAGGGACTGCTACCTGCCCA GAAGGCGGCAGGGAGGGGAAGA GCAGATNAGGAGGTATAGGGTGT GCCCTGGGCAAGGCAGCAGGGG TAACGAAGCTCT | N = A | 55 | N = A | 56 |

TABLE 17-continued sequence information of selected genotypes of additional SNPs affecting response

| rsID | Sequence | Selected nucleotide variation major allele | SEQ ID NO | Selected nucleotide variation minor allele | SEQ ID NO |
|---|---|---|---|---|---|
| Rs 1045642 | GAGAACATTGCCTATGGAGACAA CAGCCGGGTGGTGTCACAGGAA GAGATNGTGAGGGCAGCAAAGG AGGCCAACATACATGCCTTCATC GAGTCACTGCC | N = T | 57 | N = T | 58 |
| Rs 880054 | ACAGTAATAGTCTATTTAGCCTCT TTCTCTCCTGCTCTCCTTTCCATA TTNTTATGTGGCATATTAACTTAA CACTAATGT ATGCAGGGTTTTGTTGGTTT | N = A or G | 59 | N = G | 60 |
| Rs 10502933 | AATGTGATTTTTGATATAATTCTC ATGTTTTAGCTTTTCTAGTTTAAAA ANCTGCATACTGGAAAATAAGGA AAAAATTCTAGAGGTTGTATGAGA AGGA | N = C | 61 | N = T | 62 |
| Rs 2131127 | AACCAACTTTAGCATACCAAGTTT AGCATTTAGGCATACCAACTTTAG CANTGTTATACAGAATAATGTTAG CATTGGAAGGATCTATTAACAAAA GAAAG | N = C | 63 | N = C | 64 |
| Rs 4309483 | CCTCATGCAAAGCACTTGCTCAC ACACTGTCTCATTTCAACATCACC GCCNCTTAAGGAGATGCTATGAT CAACCCCACTTTGCAGATGAGGA AACTTCAG | N = A | 65 | N = A | 66 |
| Rs 4739037 | CTGGAGCTCGCCTTACACCAAAC AGACACAATCGATCCATTCGAAG TGTCNTAATTACACATTGAGGGA CCAACTAGACCTTTTCTCATTGTA AACTTGGA | N = G | 67 | N = A | 68 |

Exemplary probes suitable to be used to detect sequence information in methods and systems herein described are listed in Table 18.

TABLE 18 exemplary probes for core SNPs

| rsID | Primer forward | SEQ ID NO | Primer reverse | SEQ ID NO |
|---|---|---|---|---|
| rs16877182 | TTTGAGAATACCAAAATACAGAAAA ATTCAATCAAATTTTAAAGTTGGTA | 69 | ATTAATATGAACAATAAC CTTATCATTAAATCAAAA GAATTAAATCAAAGA | 70 |
|  | TAATTATACTTGTTATTGGAATGTA ATTTAGTTTTCTTAATTTAGTTTCT | 71 | AAACTCTTATGGTTTTAT GACTCTTTTATTGTTAGT TTAAAATTTCAACCAT | 72 |
| rs5013093 | GGAAAAACCCAGTGCCCTCCCCTC CTCTCAAGCCTGGCCAGCTCTGAC AG | 73 | CCCTCCTGAGGGGTTTT CTCTCCGAGACCGGGA CCGAGGTACAGGAAGG TC | 74 |
|  | GGGAGGACTCCCCAAAGAGA GGCTCTGGCCCTGGCTCCATGTC CTTCCAG | 75 | CCTTTTTGGGTCACGGG AGGGGAGGAGAGTTCG GACCGGTCGAGACTGTC | 76 |
| rs2461911 | GTCCAAATGTAATGTTCTAACTTAG TACATTTGGAAAATTCTTTCCTAAC | 77 | GGAGACCCTTTTGTGTT TTATAATGAATGTTTTTA TTTACGTATTTTTAC | 78 |

TABLE 18-continued exemplary probes for core SNPs

| rsID | Primer forward | SEQ ID NO | Primer reverse | SEQ ID NO |
|---|---|---|---|---|
| | CCTCTGGGAAAACACAAAATATTACTTACAAAAATAAATGCATAAAAATG | 79 | CAGGTTTACATTACAAGATTGAATCATGTAAACCTTTTAAGAAAGGATTG | 80 |
| rs12513375 | GCTCGCCTTGGTCCACTGTGACACACAGGCTGCTTTGCTGGGAAAGTTCT | 81 | GGACTGAGTGACCCCGACGTACTTCGGACCCCTCCGTTCGAAGACCGCAC | 82 |
| | CCTGACTCACTGGGGCTGCATGAAGCCTGGGGAGGCAAGCTTCTGGCGTG | 83 | CGAGCGGAACCAGGTGACACTGTGTGTCCGACGAAACGACCCTTTCAAGA | 84 |
| rs16893522 | TGACACATGTGGCAGTCTGAAAAGTTCTTATTGAGCCAGACTGTAGAGTTCTTGGAAATC | 85 | GTATGGTAAAGTACCCTTAATACTAAGATGAGTCCGACCCTCCTCATGTAATTGTCTTC | 86 |
| | CATACCATCTTCATGGGAATTATGATTCTACTCAGGCTGGGAGGAGTACATTAACTGAAG | 87 | ACTGTGTACACCGTCAGACTTTTCAAGAATAACTCGGTCTGACATCTCAAGAACCTTTAG | 88 |
| rs2345088 | CAACATTTGGATTATGGCATTTGGGATTCTGATTTTCAGAATTATGATTGGCAATTTTAA | 89 | ATTAAGACCGAGCCATATAATTATTACGTTACGAAAAAAGTTCGATAAACATTCACTAAG | 90 |
| | TAATTCTGGCTCGGTATATTAATAATGCAATGCTTTTTTCAAGCTATTTGTAAGTGATTC | 91 | GTTGTAAACCTAATACCGTAAACCCTAAGACTAAAAGTCTTAATACTAACCGTTAAAATT | 92 |

Some of the methods and systems herein exemplified can overcome certain limitations of a non pharmacogenomic therapeutic use of rostafuroxin by proposing: the selection of a subset of patients according to their genetic characteristics (SNPs). In particular, the SNPs at issue appears to underlay the blood pressure response to rostafuroxin (Core SNPs) alone and in combination with other SNPs (CAND 1, CAND 2) that are involved in mechanisms leading to hypertension and organ complications and that are also hit by rostafuroxin.

In particular, both the core SNPs and CAND 1 or CAND 2 SNPs contribute to the two phenotypes of interest: a) response to the selective drug b) development of hypertension and its organ complications. Moreover, from the practical view point both groups of SNPs contribute to discriminate, between responders and not responders.

This finding can have two important implications in the quest to find the right drug for the right patient and to open a new line of research aimed at applying the network concept of a disease (so far studied in animal model) to human patients.

The results of studies on polygenic-multifactorial diseases in animal models suggest that the current paradigm: "one genetic molecular alteration (or one gene variant or SNP) "one pathophysiological mechanism", and "one clinical symptom or disease", should be abandoned in favor of a more broad concept of genetic environmental network of mechanisms. Disease may arise from a perturbation of this network. This perturbation may then be the target for a novel "causal" therapy. This new concept under development in animal models is not readily applicable to humans because the unavailability or the specific tissues or organs whose abnormalities may trigger the disease of interest.

Methods herein described apply, for the first time, this strategy to humans. In fact, the combination of the genetic perturbation (defined by the two groups of SNPs) with the functional perturbation (measured as the blood pressure response to the very potent and selective antihypertensive agent, rostafuroxin) realizes a new approach to the identification of a peculiar genetic network underlying hypertension with its organ complications in a clinically relevant subset of patients (about 25%), that is 20 million people in Europe only.

In several embodiments, methods and systems herein described deal with the genetic heterogeneity of the individual patient in a profile and with epistasis of a gene of interest. Genetic heterogeneity and epistasis are the two major problems to overcome for demonstrating causality of a given genetic mechanism in polygenic multifactorial diseases. The term genetic heterogeneity indicates that the same phenotype (biochemical, physiological or symptoms) may be produced by different genetic mechanisms. The term epistasis indicates that the effect of the same gene variant may be modulated (either blunted or magnified) by another variant arising from gene far away from the gene of interest.

These two well accepted genetic phenomenons are hampering all the attempts to apply genetics to study the mechanisms underlying the human diseases or the response to therapy.

For instance, if one postulates that a given hormone (in the specific ouabain) or protein (in the specific adducin) are involved in causing a disease (in the specific hypertension) one has to admit that the genetic pathways involved in the synthesis, transport or excretion of the hormone are also involved in determining its critical tissue level and its biological effect.

Analogously, all the genes coding for the proteins involved in modulating the cellular function of that particular protein should be considered. Of course, each of these biochemical pathways may be differently affected by the genetic background of the individual patient.

In several embodiments, in methods and systems herein described the common findings linking the various SNPs of the profile are: a) the SNPs capacity to be associated to the blood pressure response to rostafuroxin that (core SNPs); and b) the SNPs ability affect the activity of rostafuroxin in preclinical studies and to be associated to biochemical pathways underlying hypertension and its organ complications (CAND 1 and CAND 2 SNPs). Practical advantages of several embodiments of methods and systems herein described over the current antihypertensive therapy include a faster achievement of blood pressure control (through the reduction of trial and error period) in 25% of patients, 85% probability to classify responders and non responders against 30-40% of the current strategy and a good tolerability and quality of life in the treated individual as demonstrated by trial results for rostafuroxin and, most importantly, by the much wider interval of rostafuroxin doses between the active doses and the NOAEL (non adverse events levels) doses in animals (at least 100.000 time with rostafuroxin but only 20-50 time with the available drug). Additionally, in several embodiments of methods and systems herein described can be associated with a foreseeable efficient prevention of organ complication since the identity between the mechanisms affected by rostafuroxin and that underlying organ damage in the subset of patients selected by some methods and systems herein described.

This foreseeable increased efficiency has 3 clear implications over the current strategy: a) provide stronger rational (or arguments) to convince patients to follow the treatment for hypertension that is just a risk factor, but not a disease causing disturbing clinical symptoms, b) reduce the burden for patients experiencing a cardiovascular complication that contrarily, to hypertension per se, can produce a high degree of disability. c) Reduce health care costs because antihypertensive therapy may be focused on the subset of patients at greater risk to develop cardiovascular and renal complications, which are the most important source of health costs.

Finally in the subset of patients selected with the profile 4 the magnitude of the blood pressure drop obtained with rostafuroxin is about 40% larger then that obtained with the HCTZ or Losartan. This difference is much larger than that so far detected among the various antihypertensive drugs.

In general, the methods and systems herein described allow, in several embodiments, an improvement in therapy of cardiovascular condition such as hypertension. At present, only 30-40% of never treated hypertensive patients respond to the therapy with a clinically manfully fall in blood pressure. This generates frustration in the physicians, requires multiple changes of the therapy, and reduces the patients' compliance. As consequence, most patients are not adequately treated and this limits the prevention of the organ complications associated to high blood pressure. The methods and systems herein described allow to correctly classifying as responders to the rostafuroxin therapy up to 85% of the patients, thus reducing the burden of finding an active treatment. A first improvement of several embodiments, concerns safety: the effective dose of rostafuroxin in the selected patients is very low and it may range from 50 to 500 µg/day. The effective doses in relevant animal models are from 0.1 to 100 µg/kg while the maximal tolerated dose that does not produce any effects in animals (NOAEL) is of 100 mg/kg. This means that the interval between the active and the maximal tolerated dose of rostafuroxin in animals is higher than 100.000 times as compared with the available antihypertensive therapies for which this interval ranges from 20 to 50 times. Some data concerning the efficacy and safety of new antihypertensive therapies and in particular of traditional therapeutic approaches compared with pharmacogenomic approaches is reported in FIG. 10.

In summary, the methods and systems herein described (genotyping+rostafuroxin) combine a high safety with the more accurate prediction of the antihypertensive activity thus anticipating a high degree of prevention of the cardiovascular complications whose mechanisms are hinted by rostafuroxin.

Even though the precise mechanisms of the increased blood pressure drop after rostafuroxin in individuals carrying at least on of the selected core SNPs are not known, they are expected to be related to the mechanisms triggered by the molecular targets hit by rostafuroxin. As consequence, benefits beyond those related to the blood pressure drop induced by rostafuroxin are expected in individuals carrying the core SNPs genotypes included in the profiles.

The examples set forth above are provided to give those of ordinary skill in the art a complete disclosure and description of how to make and use the embodiments of the methods and systems of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Various methods and materials similar or equivalent to those described herein can be used in practice for testing the specific examples of appropriate materials and methods described herein and are identifiable by a skilled person.

A number of embodiments of the disclosure have been described. Nevertheless, it will be understood that various modifications may be made without departing from the spirit and scope of the present disclosure. Accordingly, other embodiments are within the scope of the following claims.

REFERENCES

[1] Ferrari P, Ferrandi M, Tripodi G, Torielli L, Padoani G, Minotti E. PST 2238: a new antihypertensive compound that modulates Na,K-ATPase in genetic hypertension, J. Pharmacol. Exp. Ther., 1999; 288:1074-1083.

[2] Ferrari P, Ferrandi M, Valentini G, Bianchi G. Rostafuroxin: an ouabain antagonist that corrects renal and vascular Na+-K+-ATPase alterations in ouabain and adducin-dependent hypertension. Am J. Physiol. Regul Integr Comp Physiol 2006; 290:529-535.

[3] Ferrari P, Ferrandi M, Torielli L, Tripodi G, Melloni P, Bianchi G. PST 2238: a new antihypertensive compound that modulates Na+,K+-ATPase and antagonizes the pressor effect of OLF. Cardiovasc Drug Rev 1999; 17:39-57.).

[4] Bianchi G. et al., Pharmacogenomics 2003 May; 4(3): 279-96.

[5] J. Med. Chem., 1997; 40(11); 1561-1564.

[6] Ferrari P et al. JPET 1998; 285: 83-94.

[7] 2003 European Society of Hypertension-European Society of Cardiology guidelines for the management of arterial hypertension. Guidelines Committee Journal of Hypertension. 21(6):1011-1053, June 2003.

[8] O'Brien, Eoin; Asmar, Roland; Beilin, Lawrie; Imai, Yutaka; Mallion, Jean-Michel; Mancia, Giuseppe; Mengden, Thomas; Myers, Martin; Padfield, Paul; Palatini, Paolo; Parati, Gianfranco; Pickering, Thomas; Redon, Josep; Staessen, Jan; Stergiou, George; Verdecchia, Paolo on behalf of the European Society of Hypertension Working Group on Blood Pressure Monitoring. European Society of Hypertension recommendations for conventional, ambulatory and home blood pressure measurement. Journal of Hypertension. 21(5):821-848, May 2003.

[9] Sambrook J, Russell D W. Molecular cloning, A laboratory manual. (Chapter 6). Cold Spring Harbor Laboratory Press 2001.

[10] Steemers F J, Gunderson K L. Illumina Inc. Pharmacogenomics 2005; 6:777-782.

[11] Phase I HapMap, 2005. The international HapMap Consortium. A Haplotype Map of The Human Genome 2005; 437:1299-1320.

[12] Phase II HapMap, 2007. The international HapMap Consortium, A second generation human haplotype map of over 3.1 million SNPs. Nature 2007; 449: 851-861.

[13] Report Valentini.

[14] Page I H, Dustan H P. Persistence of normal blood pressure after discontinuing treatment in hypertensive patients. Circulation 1962; 25:433-436.

[15] Fletcher A E, Franks P J, Bulpitt C J. The effect of withdrawing antihypertensive therapy: a review. J Hypertens 1988; 6:431-436.

[16] Veterans Administration Cooperative Study Group on Antihypertensive Agents. Return of elevated blood pressure after withdrawal of antihypertensive drugs. Circulation 1975; 51:1107-1113.

[17] Levinson P D, Khatri Im, Freis E D. Persistence of normal blood pressure after withdrawal of drug treatment in mild hypertension. Arch Int Med 1982; 142:2265-2268.

[18]. Nelson M R, Reid C M, Krum H, Ryan P, Wing L M H, McNeil J J. Short-term predictors of maintenance of normotension after withdrawal of antihypertensive drugs in the second Australian national blood pressure study/ANBP2). American Journal Hypertens 2003; 16:39-45.

[19] Takata Y, Yoshizumi T, Ito Y, Ueno M, Tsukashima A, Iwase M et al. Comparison of withdrawing antihypertensive therapy between diuretics and angiotensin converting enzyme inhibitors in essential hypertensives. American Heart Journal 1992; 124:1574-1580.

[20] Blaufox M D, Langford H G, Oberman A, Hawkins C M, Wassertheil-Smoller S, Cutter G R. Effect of dietary change on the return of hypertension after withdrawal of prolonged antihypertensive therapy (DISH). J Hypertens 1984; 2(suppl 3):179-181.

[21] Ho G Y F, Blaufox M D, Wassertheil-Smoller S, Oberman A, Langford H G. Plasma renin predicts success of antihypertensive drug withdrawal. American Journal Hypertens 1994; 7:679-684.

[22] Swart S, Bing R F, Swales J D, Thurston H. Plasma renin in long-term diuretic treatment of hypertension: effect of discontinuation and restarting therapy. Clin Sci 1982; 63:121-125.

[23] Fagerberg B, Wikstrand J, Berglund G, Hartford M, Ljungman S, Wendelhag I. Withdrawal of antihypertensive drug treatment: time-course for redevelopment of hypertension and effects upon left ventricular mass. J Hypertens 1992; 10:587-593.

[24] Zanchetti A, Mancia G. The dilemma of placebo controlled studies: scientific evidence, guidelines, ethics and regulatory recommendations. J Hypertens 2009; 27:1-2.

[25] Farquharson C A J, Struthers A D. Gradual reactivation over time of vascular tissue angiotensin I to angiotensin II conversion during chronic lisinopril therapy in chronic heart failure. J Am Coll Cardiol 2002; 39:767-775.

[26] Chevillard C, Brown N L, Jouquey S, Mathieu M N, Laliberté F, Hamon G. Cardiovascular actions and tissue-converting enzyme inhibitory effects of chronic enalapril and trandolapril treatment of spontaneously hypertensive rats. J Cardiovasc Pharmcol 1989; 14:297-301.

[27] Unger T, Ganten D, Lang R E, Sohölkens A. Persistent tissue converting enzyme inhibition following chronic treatment with Hoe498 and MK421 in spontaneously hypertensive rats. J Cardiovasc Pharmacol 1985; 7:36-41.

[28] Paull J R A, Widdop R E. Persistent cardiovascular effects of chronic renin-angiotensin system inhibition following withdrawal in adult spontaneously hypertensive rats. J Hypertens 2001; 19:1393-1402.

[29] Guerrero E I, Ardanaz N, Sevilla M A, Arèvalo M A, Montero M J. Cardiovascular effects of nebivolol in spontaneously hypertensive rats persist after treatment withdrawal. J Hypertens 2006; 24:151-158.

[30] Dukacz S A W, Adams M A, Kline R L. The persistent effect of long-term enalapril on pressure natriuresis in spontaneously hypertensive rats. Am J Physiol Renal Physiol 1997; 273 o 42:F104-F112.

[31] Wigginton J E, Cutler D J, Abecasis G R. A note on exact tests of Hardy-Weinberg equilibrium. Am J Hum Genet. 2005; 76:887-893.

[32] Devlin B, Bacanu B, Roeder K: Genomic Control in the Extreme. Nature Genetics 2004; 36:1129-1130.

[33] Purcell S, Neale B, Todd-Brown K, Thomas L, Ferreira M A, Bender D. A Tool Set for Whole-Genome Association and Population-Based Linkage Analyses. Am. J. Hum Gen 2007; 81:559-575.

[34] The Wellcome Trust Case Control Consortium. Genome-wide association study of 14,000 cases of seven common diseases and 3,000 shared controls. Nature 2007; 447:661-678.

[35] Potkin S, Turner J, Guffanti G, Lakatos A, Torn F, Keator D B, Macciardi F. Genome-wide Strategies for Discovering Genetic Influences on Cognition and Cognitive Disorders Methodological Consideration. Submitted to Cognitive Psychiatry Cogn Neuropsychiatry. 2009; 14(4-5):391-418

[36] Agresti A. 1984. Analysis of Ordinal Categorical Data—New York: John Wiley & Sons, Inc.

[37] Ressom H W, Varghese R S, Zhang Z, Xuan J, Clarke R. Classification algorithms for phenotype prediction in genomics and proteomics. Front Biosci. 2008; 1; 13:691-708.

[38] Guidance for Industry: Pharmacogenomics data submission; FDA report, 5 Mar. 2005; available at the FDA website fda.gov/cder/guidance/index.htm.

[39] Phillips P C. Epistasis the essential role of gene interactions in the structure and evolution of genetic systems. Nar Rev Genet 2008; 9:855-867.

[40] Pheasant M, Mattick J S. Raising the estimate of functional human sequences. Genome Res. 2007 September; 17(9):1245-53.

The invention claimed is:

1. A method comprising:
administering Rostafuroxin once a day in an amount of 0.005 mg to 5.0 mg/day to treat or prevent a cardiovascular condition in an individual genotyped as having at least one genotype selected from the group consisting of genotype TT for rs2345088, genotype C/T for rs16877182, genotype AA for rs16893522, genotype AA for rs2461911, genotype TT for rs5013093, and genotype TT for rs12513375.

2. The method of claim 1, wherein the individual has been further genotyped for at least one polymorphism selected from the group consisting of rs4961, rs4984, rs3731566, rs914247, rs1045642, rs242093, rs1996396, rs10503806, rs13251780, rs17430706, rs10102024, rs526302, rs544104, rs3102087, rs5183, rs3772627, rs2276736, rs2131127, rs3741559, rs2217342, rs10927888, rs6604909, rs945403, rs7117314, rs10790212, rs11216598, rs910682, rs13218316, rs4309483, rs13280307, rs4739037, rs17596774, rs2728108, rs17786456, rs7696304, rs2725222, rs17199565, rs2758152, rs1057293, rs16960712, rs759359, rs404214, rs1005213, rs17025453, rs2110923, rs1428571, rs435404, rs12908787, rs11647727, rs880054, rs11064584, rs12996186, rs9893372, rs7216331, rs7521668, rs188334, rs4998662, rs16893522, rs6457110, rs3893464, rs2517718, rs1362126, rs5013093, rs2345088, rs6718282, rs721207, rs2555500, rs2461911, rs8179654, rs1901139, rs2427832, rs9361863, rs1998394, ga001619, rs2275531, rs748140, rs4710592, rs2743951, rs10159569, rs3087816, rs10493940, rs16877182, rs2326912, rs1110446, rs12513375, and rs17414954.

3. The method of claim 1, wherein the individual has been further genotyped for at least one single nucleotide polymorphisms selected from the group consisting of rs4961, rs4984, rs3731566, rs914247, and rs1045642.

4. The method of claim 1, wherein the individual has been further genotyped for of at least one genotype selected from the group consisting of GT for rs4961, CT for rs4984, AG for rs3731566, GA for rs914247, and TC for rs1045642.

5. The method of claim 1, wherein the individual has been genotyped for a genotype AA for rs914247.

6. The method of claim 1, wherein the individual has been further genotyped for at least one single nucleotide polymorphism selected from the group consisting of rs242093, rs1996396, rs10503806, rs13251780, rs17430706, rs10102024, rs526302, rs544104, rs3102087, rs5183, rs3772627, rs2276736, rs2131127, rs3741559, rs2217342, rs10927888, rs6604909, rs945403, rs7117314, rs10790212, rs11216598, rs910682, rs13218316, rs4309483, rs13280307, rs4739037, rs17596774, rs2728108, rs17786456, rs7696304, rs2725222, rs17199565, rs2758152, rs1057293, rs16960712, rs759359, rs404214, rs1005213, rs17025453, rs2110923, rs1428571, rs435404, rs12908787, rs11647727, rs880054, and rs11064584.

7. The method of claim 1, wherein the individual has been further genotyped for at least one additional single nucleotide polymorphism selected from the group consisting of rs12996186, rs9893372, rs7216331, rs7521668, rs188334, rs4998662, rs16893522, rs6457110, rs3893464, rs2517718, rs1362126, rs5013093, rs2345088, rs6718282, rs721207, rs2555500, rs2461911, rs8179654, rs1901139, rs2427832, rs9361863, rs1998394, ga001619, rs2275531, rs748140, rs4710592, rs2743951, rs10159569, rs3087816, rs10493940, rs16877182, rs2326912, rs1110446, rs12513375, and rs17414954.

8. The method of claim 1, wherein the individual has been genotyped for at least one single nucleotide polymorphism selected from the group consisting of rs4961, rs4984, rs10923835, rs947130, rs914247, rs1045642, rs880054, rs10502933, rs2131127, rs4309483, and rs4739037.

9. The method of claim 1, wherein the individual has been further genotyped for at least one single nucleotide polymorphism selected from the group consisting of rs1045642, rs10923835, rs914247, rs4961, rs947130, rs4309483, rs2131127, rs10502933, and rs880054.

10. The method of claim 1, wherein the individual has been further genotyped for at least one single nucleotide polymorphism elected from the group consisting of rs1045642, rs10923835, rs914247, rs947130, rs4739037, rs43909483, rs4984, rs10502933 and rs880054.

11. The method of claim 1, where the cardiovascular condition is hypertension and/or a condition associated thereto.

12. The method of claim 11, wherein the cardiovascular condition associated thereto is at least one of cardiac hypertrophy, cardiac insufficiency, cardiac failure, cardiac ischemia, increased vascular resistances, increased vascular reactivity, vascular stiffness, increased vascular thickness, renal hypertrophy, renal failure, glomerulosclerosis, proteinuria, polycistic renal disease, retinal damage, cerebrovascular disorders, cerebrovascular damage, stroke, Meniere syndrome, cognitive disorders, and bipolar disorders.

13. The method according to claim 1, wherein the administering is performed by administering 0.05 mg to 0.15 mg/day of Rostafuroxin.

14. The method according to claim 1, wherein the administering is performed by administering 0.01 mg to 1.5 mg/day of Rostafuroxin.

15. The method according to claim 1, wherein the administering is performed by administering 0.05 mg to 0.5 mg/day of Rostafuroxin.

16. A method comprising:
administering Rostafuroxin in a dosage of from 0.005 mg/day to 5 mg/day, to an individual genotyped as having a genotype comprising at least one of genotype TT for rs2345088, genotype C/T for rs16877182, genotype AA for rs16893522, genotype AA for rs2461911, genotype TT for rs5013093, and genotype TT for rs12513375.

17. The method of claim 16, wherein treatment with Rostafuroxin is directed to at least one biological activity selected from the group consisting of elective inhibition of the ouabain hypertensive effect, normalization of alterations in the Na—K pump and Src caused by ouabain, normalization in forms of hypertension sustained by the concomitant increase of endogenous ouabain levels and alterations in the Na—K pump and Src.

18. The method of claim 16, wherein treatment with Rostafuroxin is directed to elicit at least one biological activity selected from the group consisting of selective antagonism of the hypertensive effect associated to the genetic variations of genes coding for adducin or other enzymes involved in synthesis and transport of endogenous ouabain, normalization of alterations in the Na—K pump and Src caused by adducin genetic variations, and normalization in forms of hypertension sustained by the concomitant effects of adducin genetic variations and alterations in the Na—K pump and Src.

19. The method of claim 16, wherein the dosage is from 0.05 mg/day to 0.15 mg/day.

20. The method of claim 16, wherein the dosage is from 1.5 mg/day to 5.0 mg/day.

21. The method of claim 16, wherein the dosage is from 0.05 mg/day to 1.5 mg/day.

22. The method of claim 16, wherein the individual has been further genotyped for at least one polymorphism selected from the group consisting of rs4961, rs4984, rs3731566, rs914247, rs1045642, rs242093, rs1996396, rs10503806, rs13251780, rs17430706, rs10102024, rs526302, rs544104, rs3102087, rs5183, rs3772627, rs2276736, rs2131127, rs3741559, rs2217342, rs10927888, rs6604909, rs945403, rs7117314, rs10790212, rs11216598, rs910682, rs13218316, rs4309483, rs13280307, rs4739037, rs17596774, rs2728108, rs17786456, rs7696304, rs2725222, rs17199565, rs2758152, rs1057293, rs16960712, rs759359, rs404214, rs1005213, rs17025453, rs2110923, rs1428571, rs435404, rs12908787, rs11647727, rs880054, rs11064584, rs12996186, rs9893372, rs7216331, rs7521668, rs188334, rs4998662, rs16893522, rs6457110, rs3893464, rs2517718, rs1362126, rs5013093, rs2345088, rs6718282, rs721207, rs2555500, rs2461911, rs8179654, rs1901139, rs2427832, rs9361863, rs1998394, ga001619, rs2275531, rs748140, rs4710592, rs2743951, rs10159569, rs3087816, rs10493940, rs16877182, rs2326912, rs1110446, rs12513375, and rs17414954.

23. The method of claim 22, wherein the administering is performed through an administration route selected from the group consisting of oral, intravenous, intramuscular, intraarterial, intramedullary, intrathecal, intraventricular, transdermal or transcutaneous applications, subcutaneous, intraperitoneal, intranasal, enteral, topical, sublingual, rectal means or locally on the diseased tissue after surgical operation.

24. A method comprising:
assaying an individual using nucleic acid probes for at least one genotype selected from the group consisting of genotype TT for rs2345088, genotype C/T for rs16877182, genotype AA for rs16893522, genotype AA for rs2461911, genotype TT for rs5013093, and genotype TT for rs12513375;

detecting the presence of said at least one genotype; and administering Rostafuroxin to the individual to treat or prevent a cardiovascular condition.

25. A method comprising:

assaying an individual using nucleic acid probes for at least one genotype selected from the group consisting of genotype TT for rs2345088, genotype C/T for rs16877182, genotype AA for rs16893522, genotype AA for rs2461911, genotype TT for rs5013093, and genotype TT for rs12513375;

detecting the presence of said at least one genotype; and administering Rostafuroxin once a day in an amount of 0.005 mg to 5.0 mg/day to the individual to treat or prevent the cardiovascular condition.

* * * * *

```
                              SEQUENCE LISTING

<160> NUMBER OF SEQ ID NOS: 92

<210> SEQ ID NO 1
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 1
tttgagaata ccaaaataca gaaaaattca atcaaatttt aaagttggta ntaattatac      60
ttgttattgg aatgtaattt agttttctta atttagtttc t                        101

<210> SEQ ID NO 2
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= C or T

<400> SEQUENCE: 2
tttgagaata ccaaaataca gaaaaattca atcaaatttt aaagttggta ntaattatac      60
ttgttattgg aatgtaattt agttttctta atttagtttc t                        101

<210> SEQ ID NO 3
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 3
ggaaaaaccc agtgccctcc cctcctctca agcctggcca gctctgacag ngggaggact      60
ccccaaagag aggctctggc cctggctcca tgtccttcca g                        101

<210> SEQ ID NO 4
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= C or T

<400> SEQUENCE: 4
ggaaaaaccc agtgccctcc cctcctctca agcctggcca gctctgacag ngggaggact      60
ccccaaagag aggctctggc cctggctcca tgtccttcca g                        101

<210> SEQ ID NO 5
<211> LENGTH: 101
<212> TYPE: DNA
```

```
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 5
gtccaaatgt aatgttctaa cttagtacat ttggaaaatt ctttcctaac ncctctggga      60
aaacacaaaa tattacttac aaaaataaat gcataaaaat g                         101

<210> SEQ ID NO 6
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= G or A

<400> SEQUENCE: 6
gtccaaatgt aatgttctaa cttagtacat ttggaaaatt ctttcctaac ncctctggga      60
aaacacaaaa tattacttac aaaaataaat gcataaaaat g                         101

<210> SEQ ID NO 7
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 7
gctcgccttg gtccactgtg acacacaggc tgctttgctg ggaaagttct ncctgactca      60
ctggggctgc atgaagcctg gggaggcaag cttctggcgt g                         101

<210> SEQ ID NO 8
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= G or T

<400> SEQUENCE: 8
gctcgccttg gtccactgtg acacacaggc tgctttgctg ggaaagttct ncctgactca      60
ctggggctgc atgaagcctg gggaggcaag cttctggcgt g                         101

<210> SEQ ID NO 9
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: N= A, C, G or T

<400> SEQUENCE: 9
tgacacatgt ggcagtctga aaagttctta ttgagccaga ctgtagagtt cttggaaatc      60
ncataccatc ttcatgggaa ttatgattct actcaggctg ggaggagtac attaactgaa     120
g                                                                    121
```

```
<210> SEQ ID NO 10
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: N= A or G

<400> SEQUENCE: 10
tgacacatgt ggcagtctga aaagttctta ttgagccaga ctgtagagtt cttggaaatc      60
ncataccatc ttcatgggaa ttatgattct actcaggctg ggaggagtac attaactgaa     120
g                                                                    121

<210> SEQ ID NO 11
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: N= A, C, G or T

<400> SEQUENCE: 11
caacatttgg attatggcat ttgggattct gattttcaga attatgattg gcaattttaa      60
ntaattctgg ctcggtatat taataatgca atgcttttttt caagctattt gtaagtgatt   120
c                                                                    121

<210> SEQ ID NO 12
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: N= C or T

<400> SEQUENCE: 12
caacatttgg attatggcat ttgggattct gattttcaga attatgattg gcaattttaa      60
ntaattctgg ctcggtatat taataatgca atgcttttttt caagctattt gtaagtgatt   120
c                                                                    121

<210> SEQ ID NO 13
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=C

<400> SEQUENCE: 13
tttgagaata ccaaaataca gaaaaattca atcaaatttt aaagttggta ntaattatac      60
ttgttattgg aatgtaattt agtttctta atttagtttc t                         101

<210> SEQ ID NO 14
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=T
```

<400> SEQUENCE: 14
tttgagaata ccaaaataca gaaaaattca atcaaatttt aaagttggta ntaattatac    60
ttgttattgg aatgtaattt agttttctta atttagtttc t                       101

<210> SEQ ID NO 15
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=T

<400> SEQUENCE: 15
ggaaaaaccc agtgccctcc cctcctctca agcctggcca gctctgacag ngggaggact    60
ccccaaagag aggctctggc cctggctcca tgtccttcca g                       101

<210> SEQ ID NO 16
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=T

<400> SEQUENCE: 16
ggaaaaaccc agtgccctcc cctcctctca agcctggcca gctctgacag ngggaggact    60
ccccaaagag aggctctggc cctggctcca tgtccttcca g                       101

<210> SEQ ID NO 17
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A

<400> SEQUENCE: 17
gtccaaatgt aatgttctaa cttagtacat ttggaaaatt ctttcctaac ncctctggga    60
aaacacaaaa tattacttac aaaaataaat gcataaaaat g                       101

<210> SEQ ID NO 18
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A

<400> SEQUENCE: 18
gtccaaatgt aatgttctaa cttagtacat ttggaaaatt ctttcctaac ncctctggga    60
aaacacaaaa tattacttac aaaaataaat gcataaaaat g                       101

<210> SEQ ID NO 19
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= T

<400> SEQUENCE: 19
gctcgccttg gtccactgtg acacacaggc tgctttgctg ggaaagttct ncctgactca     60
ctggggctgc atgaagcctg gggaggcaag cttctggcgt g                        101

<210> SEQ ID NO 20
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= T

<400> SEQUENCE: 20
gctcgccttg gtccactgtg acacacaggc tgctttgctg ggaaagttct ncctgactca     60
ctggggctgc atgaagcctg gggaggcaag cttctggcgt g                        101

<210> SEQ ID NO 21
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: N= A

<400> SEQUENCE: 21
tgacacatgt ggcagtctga aaagttctta ttgagccaga ctgtagagtt cttggaaatc     60
ncataccatc ttcatgggaa ttatgattct actcaggctg ggaggagtac attaactgaa    120
g                                                                    121

<210> SEQ ID NO 22
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: N= A

<400> SEQUENCE: 22
tgacacatgt ggcagtctga aaagttctta ttgagccaga ctgtagagtt cttggaaatc     60
ncataccatc ttcatgggaa ttatgattct actcaggctg ggaggagtac attaactgaa    120
g                                                                    121

<210> SEQ ID NO 23
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: N= T

<400> SEQUENCE: 23
caacatttgg attatggcat ttgggattct gattttcaga attatgattg caattttaa     60 ntaattctgg ctcggtatat taataatgca atgcttttt caagctattt gtaagtgatt    120
c                                                                    121

<210> SEQ ID NO 24

```
<211> LENGTH: 121
<212> TYPE: DNA
<213> ORGANISM: Homo sapiens
<220> FEATURE:
<221> NAME/KEY: misc_feature
<222> LOCATION: (61)..(61)
<223> OTHER INFORMATION: N= T

<400> SEQUENCE: 24
caacatttgg attatggcat ttgggattct gattttcaga attatgattg gcaattttaa      60
ntaattctgg ctcggtatat taataatgca atgcttttt caagctattt gtaagtgatt     120
c                                                                    121

<210> SEQ ID NO 25
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 25
agaagacaag atggctgaac tctggccggg gcgacgaagc ttccgaggaa nggcagaatg      60
gaagcagtcc caagtcgaag actaaggtgt ggacgaacat t                        101

<210> SEQ ID NO 26
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=G or T

<400> SEQUENCE: 26
agaagacaag atggctgaac tctggccggg gcgacgaagc ttccgaggaa nggcagaatg      60
gaagcagtcc caagtcgaag actaaggtgt ggacgaacat t                        101

<210> SEQ ID NO 27
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 27
cttcatcaaa acacacctac caatatgtta ctccagatgt ggagggcaac nctgaagaac      60
tcgcacacgg ccggaccaga gcctggctct cgttcctgtc c                        101

<210> SEQ ID NO 28
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= G or A

<400> SEQUENCE: 28
cttcatcaaa acacacctac caatatgtta ctccagatgt ggagggcaac nctgaagaac      60
tcgcacacgg ccggaccaga gcctggctct cgttcctgtc c                        101
```

```
<210> SEQ ID NO 29
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 29
ctacaagtct tttatgctct gaagcttttt gtcttggcaa ttgctttaca ncattcacaa      60
aggacagcat ttacctggag acctcaccag tgggtccctg c                        101

<210> SEQ ID NO 30
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A or T

<400> SEQUENCE: 30
ctacaagtct tttatgctct gaagcttttt gtcttggcaa ttgctttaca ncattcacaa      60
aggacagcat ttacctggag acctcaccag tgggtccctg c                        101

<210> SEQ ID NO 31
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 31
tctgaacaat ttgggatctc ttttaacttg agggtctctt tcgactacta nagctccatt      60
tcccctctta aatgagaagg gatttctttt cttttaaatc t                        101

<210> SEQ ID NO 32
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= C or T

<400> SEQUENCE: 32
tctgaacaat ttgggatctc ttttaacttg agggtctctt tcgactacta nagctccatt      60
tcccctctta aatgagaagg gatttctttt cttttaaatc t                        101

<210> SEQ ID NO 33
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 33
gccagggact gctacctgcc cagaaggcgg cagggagggg aagagcagat naggaggtat      60
```
agggtgtgcc ctgggcaagg cagcagggdt aacgaagctc t        101

<210> SEQ ID NO 34
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A or G

<400> SEQUENCE: 34
gccagggact gctacctgcc cagaaggcgg cagggagggg aagagcagat naggaggtat        60
agggtgtgcc ctgggcaagg cagcagggdt aacgaagctc t        101

<210> SEQ ID NO 35
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 35
gagaacattg cctatggaga caacagccgg gtggtgtcac aggaagagat ngtgagggca        60
gcaaaggagg ccaacataca tgccttcatc gagtcactgc c        101

<210> SEQ ID NO 36
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= C or T

<400> SEQUENCE: 36
gagaacattg cctatggaga caacagccgg gtggtgtcac aggaagagat ngtgagggca        60
gcaaaggagg ccaacataca tgccttcatc gagtcactgc c        101

<210> SEQ ID NO 37
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 37
acagtaatag tctatttagc ctctttctct cctgctctcc tttccatatt nttatgtggc        60
atattaactt aacactaatg tatgcagggt tttgttggtt t        101

<210> SEQ ID NO 38
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= C or T

<400> SEQUENCE: 38
acagtaatag tctatttagc ctctttctct cctgctctcc tttccatatt nttatgtggc        60

```
atattaactt aacactaatg tatgcagggt tttgttggtt t                        101
```

<210> SEQ ID NO 39
<211> LENGTH: 100
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 39

```
aatgtgattt ttgatataat tctcatgttt tagcttttct agtttaaaaa nctgcatact     60
ggaaaataag gaaaaaattc tagaggttgt atgagaagga                          100
```

<210> SEQ ID NO 40
<211> LENGTH: 100
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= C or T

<400> SEQUENCE: 40

```
aatgtgattt ttgatataat tctcatgttt tagcttttct agtttaaaaa nctgcatact     60
ggaaaataag gaaaaaattc tagaggttgt atgagaagga                          100
```

<210> SEQ ID NO 41
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 41

```
aaccaacttt agcataccaa gtttagcatt taggcatacc aactttagca ntgttataca     60
gaataatgtt agcattggaa ggatctatta acaaaagaaa g                        101
```

<210> SEQ ID NO 42
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= C or T

<400> SEQUENCE: 42

```
aaccaacttt agcataccaa gtttagcatt taggcatacc aactttagca ntgttataca     60
gaataatgtt agcattggaa ggatctatta acaaaagaaa g                        101
```

<210> SEQ ID NO 43
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 43

```
cctcatgcaa agcacttgct cacacactgt ctcatttcaa catcaccgcc ncttaaggag    60
atgctatgat caaccccact ttgcagatga ggaaacttca g                      101
```

<210> SEQ ID NO 44
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= C or A

<400> SEQUENCE: 44

```
cctcatgcaa agcacttgct cacacactgt ctcatttcaa catcaccgcc ncttaaggag    60
atgctatgat caaccccact ttgcagatga ggaaacttca g                      101
```

<210> SEQ ID NO 45
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A, C, G or T

<400> SEQUENCE: 45

```
ctggagctcg ccttacacca aacagacaca atcgatccat tcgaagtgtc ntaattacac    60
attgagggac caactagacc ttttctcatt gtaaacttgg a                      101
```

<210> SEQ ID NO 46
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= G or A

<400> SEQUENCE: 46

```
ctggagctcg ccttacacca aacagacaca atcgatccat tcgaagtgtc ntaattacac    60
attgagggac caactagacc ttttctcatt gtaaacttgg a                      101
```

<210> SEQ ID NO 47
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= G or T

<400> SEQUENCE: 47

```
agaagacaag atggctgaac tctggccggg gcgacgaagc ttccgaggaa nggcagaatg    60
gaagcagtcc caagtcgaag actaaggtgt ggacgaacat t                      101
```

<210> SEQ ID NO 48
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=T

<400> SEQUENCE: 48

-continued agaagacaag atggctgaac tctggccggg gcgacgaagc ttccgaggaa nggcagaatg   60
gaagcagtcc caagtcgaag actaaggtgt ggacgaacat t                       101

<210> SEQ ID NO 49
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=C

<400> SEQUENCE: 49
cttcatcaaa acacacctac caatatgtta ctccagatgt ggagggcaac nctgaagaac   60
tcgcacacgg ccggaccaga gcctggctct cgttcctgtc c                       101

<210> SEQ ID NO 50
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=C

<400> SEQUENCE: 50
cttcatcaaa acacacctac caatatgtta ctccagatgt ggagggcaac nctgaagaac   60
tcgcacacgg ccggaccaga gcctggctct cgttcctgtc c                       101

<210> SEQ ID NO 51
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=A or T

<400> SEQUENCE: 51
ctacaagtct tttatgctct gaagcttttt gtcttggcaa ttgctttaca ncattcacaa   60
aggacagcat ttacctggag acctcaccag tgggtccctg c                       101

<210> SEQ ID NO 52
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=T

<400> SEQUENCE: 52
ctacaagtct tttatgctct gaagcttttt gtcttggcaa ttgctttaca ncattcacaa   60
aggacagcat ttacctggag acctcaccag tgggtccctg c                       101

<210> SEQ ID NO 53
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=G

```
<400> SEQUENCE: 53
tctgaacaat tgggatctc ttttaacttg agggtctctt tcgactacta nagctccatt    60
tcccctctta aatgagaagg gatttctttt cttttaaatc t                      101

<210> SEQ ID NO 54
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=G

<400> SEQUENCE: 54
tctgaacaat tgggatctc ttttaacttg agggtctctt tcgactacta nagctccatt    60
tcccctctta aatgagaagg gatttctttt cttttaaatc t                      101

<210> SEQ ID NO 55
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=A

<400> SEQUENCE: 55
gccagggact gctacctgcc cagaaggcgg cagggagggg aagagcagat naggaggtat    60
agggtgtgcc ctgggcaagg cagcaggggt aacgaagctc t                      101

<210> SEQ ID NO 56
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=A

<400> SEQUENCE: 56
gccagggact gctacctgcc cagaaggcgg cagggagggg aagagcagat naggaggtat    60
agggtgtgcc ctgggcaagg cagcaggggt aacgaagctc t                      101

<210> SEQ ID NO 57
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=T

<400> SEQUENCE: 57
gagaacattg cctatggaga caacagccgg gtggtgtcac aggaagagat ngtgagggca    60
gcaaaggagg ccaacataca tgccttcatc gagtcactgc c                      101

<210> SEQ ID NO 58
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=T
```

<400> SEQUENCE: 58
gagaacattg cctatggaga caacagccgg gtggtgtcac aggaagagat ngtgagggca      60
gcaaaggagg ccaacataca tgccttcatc gagtcactgc c                         101

<210> SEQ ID NO 59
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N= A or G

<400> SEQUENCE: 59
acagtaatag tctatttagc ctctttctct cctgctctcc tttccatatt nttatgtggc      60
atattaactt aacactaatg tatgcagggt tttgttggtt t                         101

<210> SEQ ID NO 60
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=G

<400> SEQUENCE: 60
acagtaatag tctatttagc ctctttctct cctgctctcc tttccatatt nttatgtggc      60
atattaactt aacactaatg tatgcagggt tttgttggtt t                         101

<210> SEQ ID NO 61
<211> LENGTH: 100
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=C

<400> SEQUENCE: 61
aatgtgattt ttgatataat tctcatgttt tagcttttct agtttaaaaa nctgcatact      60
ggaaaataag gaaaaaattc tagaggttgt atgagaagga                           100

<210> SEQ ID NO 62
<211> LENGTH: 100
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=T

<400> SEQUENCE: 62
aatgtgattt ttgatataat tctcatgttt tagcttttct agtttaaaaa nctgcatact      60
ggaaaataag gaaaaaattc tagaggttgt atgagaagga                           100

<210> SEQ ID NO 63
<211> LENGTH: 101
<212> TYPE: DNA
<213> ORGANISM: Homo sapiens
<220> FEATURE:
<221> NAME/KEY: misc_feature
<222> LOCATION: (51)..(51)

<223> OTHER INFORMATION: N=C

<400> SEQUENCE: 63 aaccaactttt agcataccaa gtttagcatt taggcatacc aactttagca ntgttataca      60
gaataatgtt agcattggaa ggatctatta acaaaagaaa g      101

<210> SEQ ID NO 64
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=C

<400> SEQUENCE: 64 aaccaactttt agcataccaa gtttagcatt taggcatacc aactttagca ntgttataca      60
gaataatgtt agcattggaa ggatctatta acaaaagaaa g      101

<210> SEQ ID NO 65
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=A

<400> SEQUENCE: 65
cctcatgcaa agcacttgct cacacactgt ctcatttcaa catcaccgcc ncttaaggag      60
atgctatgat caacccccact ttgcagatga ggaaacttca g      101

<210> SEQ ID NO 66
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=A

<400> SEQUENCE: 66
cctcatgcaa agcacttgct cacacactgt ctcatttcaa catcaccgcc ncttaaggag      60
atgctatgat caacccccact ttgcagatga ggaaacttca g      101

<210> SEQ ID NO 67
<211> LENGTH: 101
<212> TYPE: DNA
<213> ORGANISM: Homo sapiens
<220> FEATURE:
<221> NAME/KEY: misc_feature
<222> LOCATION: (51)..(51)
<223> OTHER INFORMATION: N=G

<400> SEQUENCE: 67
ctggagctcg ccttacacca aacagacaca atcgatccat tcgaagtgtc ntaattacac      60
attgagggac caactagacc ttttctcatt gtaaacttgg a      101

<210> SEQ ID NO 68
<211> LENGTH: 101
<212> TYPE: DNA
<213> ORGANISM: Homo sapiens
<220> FEATURE:
<221> NAME/KEY: misc_feature

<222> LOCATION: (51)..(51)
<223> OTHER INFORMATION: N=A

<400> SEQUENCE: 68
ctggagctcg ccttacacca aacagacaca atcgatccat tcgaagtgtc ntaattacac    60
attgagggac caactagacc ttttctcatt gtaaacttgg a                        101

<210> SEQ ID NO 69
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 69
tttgagaata ccaaaataca gaaaaattca atcaaatttt aaagttggta               50

<210> SEQ ID NO 70
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 70
attaatatga acaataacct tatcattaaa tcaaagaat taaatcaaag a               51

<210> SEQ ID NO 71
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 71
taattatact tgttattgga atgtaattta gttttcttaa tttagtttct                50

<210> SEQ ID NO 72
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 72
aaactcttat ggttttatga ctcttttatt gttagtttaa aatttcaacc at             52

<210> SEQ ID NO 73
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 73
ggaaaaaccc agtgccctcc cctcctctca agcctggcca gctctgacag                50

<210> SEQ ID NO 74
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 74

```
ccctcctgag gggttttctc tccgagaccg ggaccgaggt acaggaaggt c        51
```

<210> SEQ ID NO 75
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 75

```
gggaggactc cccaaagaga ggctctggcc ctggctccat gtccttccag         50
```

<210> SEQ ID NO 76
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 76

```
cctttttggg tcacgggagg ggaggagagt tcggaccggt cgagactgtc         50
```

<210> SEQ ID NO 77
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 77

```
gtccaaatgt aatgttctaa cttagtacat ttggaaaatt ctttcctaac         50
```

<210> SEQ ID NO 78
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 78

```
ggagacccct ttgtgtttta taatgaatgt ttttatttac gtattttttac        50
```

<210> SEQ ID NO 79
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 79

```
cctctgggaa aacacaaaat attacttaca aaataaatg cataaaaatg          50
```

<210> SEQ ID NO 80
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 80

```
caggtttaca ttacaagatt gaatcatgta aaccttttaa gaaaggattg         50
```

<210> SEQ ID NO 81
<211> LENGTH: 50
<212> TYPE: DNA
<213> ORGANISM: Artificial Sequence

```
<220> FEATURE:
<223> OTHER INFORMATION: Synthetic Polynucleotide

<400> SEQUENCE: 81
gctcgccttg gtccactgtg acacacaggc tgctttgctg ggaaagttct                50

<210> SEQ ID NO 82
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 82
ggactgagtg accccgacgt acttcggacc cctccgttcg aagaccgcac                50

<210> SEQ ID NO 83
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 83
cctgactcac tggggctgca tgaagcctgg ggaggcaagc ttctggcgtg                50

<210> SEQ ID NO 84
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 84
cgagcggaac caggtgacac tgtgtgtccg acgaaacgac cctttcaaga                50

<210> SEQ ID NO 85
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 85
tgacacatgt ggcagtctga aaagttctta ttgagccaga ctgtagagtt cttggaaatc     60

<210> SEQ ID NO 86
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 86
gtatggtaaa gtacccttaa tactaagatg agtccgaccc tcctcatgta attgtcttc      59

<210> SEQ ID NO 87
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 87
cataccatct tcatgggaat tatgattcta ctcaggctgg gaggagtaca ttaactgaag     60
```

<210> SEQ ID NO 88
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 88
actgtgtaca ccgtcagact tttcaagaat aactcggtct gacatctcaa gaaccttag    60

<210> SEQ ID NO 89
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 89
caacatttgg attatggcat ttgggattct gattttcaga attatgattg gcaatttaa    60

<210> SEQ ID NO 90
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 90
attaagaccg agccatataa ttattacgtt acgaaaaaag ttcgataaac attcactaag    60

<210> SEQ ID NO 91
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 91
taattctggc tcggtatatt aataatgcaa tgcttttttc aagctatttg taagtgattc    60

<210> SEQ ID NO 92
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 92
gttgtaaacc taataccgta aaccctaaga ctaaagtct taatactaac cgttaaaatt    60